(12) United States Patent
Zhu et al.

(10) Patent No.: US 8,198,364 B2
(45) Date of Patent: Jun. 12, 2012

(54) POLY (VINYL ALCOHOL) POLYMERS, USES AND PREPARATION THEREOF

(75) Inventors: Julian Xiao-Xia Zhu, Dollard-des-Ormeaux (CA); Pardin Christophe, Montréal (CA); Juntao Luo, Sacramento, CA (US); William A. Lubell, Montréal (CA); Tarek Kassem, Montréal (CA)

(73) Assignee: Valorisation-Recherche, Limited Partnership, Montreal (CA)

( * ) Notice: Subject to any disclaimer, the term of this patent is extended or adjusted under 35 U.S.C. 154(b) by 633 days.

(21) Appl. No.: 12/308,223

(22) PCT Filed: Jun. 14, 2007

(86) PCT No.: PCT/CA2007/001063
§ 371 (c)(1),
(2), (4) Date: May 18, 2009

(87) PCT Pub. No.: WO2007/143484
PCT Pub. Date: Dec. 21, 2007

(65) Prior Publication Data
US 2010/0038297 A1    Feb. 18, 2010

Related U.S. Application Data

(60) Provisional application No. 60/804,664, filed on Jun. 14, 2006.

(51) Int. Cl.
C08F 16/06 (2006.01)
C08F 290/04 (2006.01)
C08G 63/48 (2006.01)
C08F 8/00 (2006.01)

(52) U.S. Cl. ....... 525/56; 210/198.2; 424/486; 424/492; 428/195.1; 524/504; 525/54.1; 525/58; 525/59

(58) Field of Classification Search .................. None
See application file for complete search history.

(56) References Cited

U.S. PATENT DOCUMENTS
2005/0065292 A1    3/2005    Park et al.
2005/0271727 A1    12/2005    Yao

FOREIGN PATENT DOCUMENTS
EP    1440995 A1    7/2004

OTHER PUBLICATIONS

Gordon et al., "Combinatorial Chemistry and Molecular Diversity in Drug Discovery", Wiley-Liss, 1998. 516 pp.
Merrifield, R.B., "Solid Phase Peptide Synthesis. I. The Synthesis of a Tetrapeptide", J. Am. Chem. Soc., 1963, vol. 85, pp. 2149-2154.

(Continued)

Primary Examiner — Krishnan S Menon
Assistant Examiner — Dirk Bass

(57) ABSTRACT

There are provided poly(vinyl alcohol) polymers and copolymers containing vinyl alcohol or vinyl acetate and derivatives thereof such as poly(ethylene glycol)-grafted poly(vinyl alcohol) polymers or polyether-grafted poly(vinyl alcohol) polymers. These polymers can contain various functional groups. Such polymers can be use as polymer matrix or solid support for various chemical substrates such as organic substrates and reagents. Cross-linked poly(vinyl alcohol) polymers and copolymers are also provided. Methods for preparing such polymers as well as several of their uses are also included.

18 Claims, 7 Drawing Sheets

OTHER PUBLICATIONS

Grotli et al., "Physical Properties of Poly(ethylene glycol) (PEG)-Based Resins for Combinatorial Solid Phase Organic Chemistry: A Comparison of PEG-Cross-Linked and PEG-Grafted Resins", J. Comb. Chem., 2000, vol. 2, No. 2, pp. 108-119.
In Combinatorial Peptide and Nonpeptide Libraries: A Handbook; Jung, G., Ed., John Wileys & sons: New York, 1998, pp. 425-464.
Renil et al., "PEGA Supports for Combinatorial Peptide Synthesis and Solid-phase Enzymatic Library Assays", J. Pept. Sci. 1998, vol. 4, pp. 195-210.
Renil et al., "POEPOP and POEPS: Inert Polyethylene Glycol Crosslinked Polymeric Supports for Solid Synthesis", Tetrahedron Letters, 1996, vol. 37, No. 34, pp. 6185-6188.
Moss et al., "Solid phase peptide synthesis on JandaJel™ resin", Tetrahedron Letters, 2002, vol. 43, pp. 37-40.
Kempe et al., "Clear: A Novel Family of Highly Cross-Linked Polymeric Supports for Solid-Phase Peptide Synthesis", J. Am. Chem. Soc., 1996, vol. 118, No. 30, pp. 7083-7093.
Miranda et al., "SPOCC-194, a New High Functional Group Density PEG-Based Resin for Solid-Phase Organic Synthesis", J. Comb. Chem. 2002, vol. 4, No. 5, pp. 523-529.
Lam et al., "A new type of synthetic peptide library for identifying ligand biding activity", Nature, 1991, vol. 354, pp. 82-84.
Van Heerbeek et al., "Dendrimers as Support for Recoverable Catalysts and Reagents", Chem. Rev., 2002, vol. 102, No. 10, pp. 3717-3756.
Lebreton, et al., "Solid-Phase Dendrimer Chemistry: Synthesis and Applications", Aldrichimica Acta 2001, vol. 34, No. 3, pp. 75-83.
Arkin et al., "Synthesis of Poly(2-methyl-3-hydroxyoctanoate) via Anionic Polymerization of α-Methyl-β-pentyl-β-propiolactone", Biomacromolecules, 2001; vol. 2, No. 3, pp. 623-627.
Becht et al., "Enantioselective Syntheses of (−)-(R)-Rolipram, (−)-(R)-Baclofen and Other GABA Analogues via Rhodium-Catalyzed Conjugate Addition of Arylboronic Acids", Synthesis, 2003, No. 18, pp. 2805-2810.
Dettwiler et al., "Diversity-oriented synthesis of enantiopure N-protected, β,β-dialkylserines", Can. J. Chem., 2004, vol. 82, No. 2, pp. 318-324.
Gosselin et al., "An Olefination Entry for the Synthesis of Enantiopure α,w-Diaminodicarboxylates and Azabicyclo[X.Y.0]alkane Amino Acids", J. Org. Chem., 1998, vol. 63, No. 21, pp. 7463-7471.
Tomori et al., "Lipase-Catalysed Practical Synthesis of (R)-1-Benzyl-3-hydroxy-2,5-pyrrolidinedione and Its Related Compounds", Bull. Chem. Soc. Jpn., 1996, vol. 69, No. 1, pp. 207-215.
Rensen et al., "Design and Synthesis of Novel N-Acetylgalactosamine-Terminated Glycolipids for Targeting of Lipoproteins to the Hepatic Asialoglycoprotein Receptor", J. Med. Chem., 2004, vol. 47, No. 23, pp. 5798-5808.
Wan et al., "Preparation and characterisation of high loading porous crosslinked poly(vinyl alcohol) resins", Polymer, 2004, vol. 45, pp. 71-77.
Wang et al., "Functionalized Cross-Linked Poly(vinyl alcohol) Resins as Reaction Scavengers and as Supports for Solid-Phase Organic Synthesis", J. Comb. Chem., 2004, vol. 6, No. 6, pp. 961-966.
.Yan et al., "Rapid Fluorescence Determination of the Absolute Amount of Aldehyde and Ketone Groups on Resin Supports", J. Org. Chem., 1997, vol. 62, No. 26, pp. 9354-9357.
Okaniwa et al., "One-Pot Synthesis of Dendritic Poly(amide-urea)s via Curtius Rearrangement. 1. Monomer Syntheses and Model Reactions for the Dendritic Poly(amide-urea)s Synthesis", Macromolecules, 2002, vol. 35, No.16, pp. 6224-6231.
Kaiser et al., "Color Test for Detection of Free Terminal Amino Groups in the Solid-Phase Synthesis of Peptides", Anal. Biochem, 1970, vol. 34, pp. 595-598.
Moritani et al., "13C- and 1H-NMR Investigations of Sequence Distribution in Vinyl Alcohol-Vinyl Acetate Copolymers", Macromolecules, 1977, vol. 10, No. 3, pp. 532-535.
Budhlall et al., "Characterization of Partially Hydrolyzed Poly(vinyl alcohol). Effect of Poly(vinyl alcohol) Molecular Architecture on Aqueous Phase Conformation", Macromolecules, 2003, vol. 36, No. 25, pp. 9477-9484.
Keifer, Paul A., "High-resolution NMR techniques for solid-phase synthesis and combinatorial chemistry", Drug Discovery Today, 1997, vol. 2, No. 11, pp. 468-478.
Rostovtsev et al., "A Stepwise Huisgen Cycloaddition Process: Copper(I)-Catalyzed Regioselective "Ligation" of Azides and Terminal Alkynes", Angew. Chem. Int. Ed., 2002, vol. 41, No. 14, pp. 2596-2599.
Sharpless et al., "Click Chemistry: Diverse Chemical Function from a Few Good Reactions", Angew. Chem. Int. Ed., 2001, vol. 40, pp. 2004-2021.
Gillet et al., "Expression and rapid purification of highly active hexahistidine-tagged guinea pig liver transglutaminase", Protein Expression & Purification, 2004, vol. 33, pp. 256-264.
Adam et al., "Synthetic Applications of Nonmetal Catalysts for Homogeneous Oxidations", Chem. Rev. 2001, vol. 101, No. 11, pp. 3499-3548.
Biel et al., "Synthesis and Evaluation of Acyl Protein Thioesterase 1 (APT1) Inhibitors", Chem. Eur. J., 2006, vol. 12, pp. 4121-4143.
Suprenant et al., "9-(4-Bromophenyl)-9-fluorenyl as a Safety-Catch Nitrogen Protecting Group", J. Org. Chem, 2006, vol. 71, No. 2, pp. 848-851.
Font et al., "Polystyrene-Supported Hydroxyproline: An Insoluble, Recyclable Organocatalyst for the Asymmetric Aldol Reaction in Water", Organic Letters, 2006, vol. 8, No. 20, pp. 4653-4655.
Siggia, S., "Instrumental Methods of Organic Functional Group Analysis", Wiley, 1972.
Atherton et al., "Solid phase peptide synthesis: a practical approach" IRL Press, Oxford, 1989.
Burger et al., "Enzymatic, Polymer-Supported Formation of an Analog of the Trypsin Inhibitor A90720A: A Screening Strategy for Macrocyclic Peptidase Inhibitors", J. Am. Chem. Soc., 1997, vol. 119, No. 51, pp. 12697-12698.
Lam et al. The "One-Bead-One-Compound" Combinatorial Library Method, Chem. Rev., 1997, vol. 97, No. 2, pp. 411-448.
Chen et al. "Strategies Toward Biocompatible Artificial Implants: Grafting of Functionalized Poly(ethylene glycol)s to Poly(ethylene terephtahalte) Surfaces", Journal of Polymer Science: Part A: Polymer Chemistry, vol. 42, pp. 5389-5400.
Sefton et al. "Platelet Consumption by Polyvinyl Alcohol (PVA) Hydrogels and Modified PVA Surfaces", Polymeric Materials Science and Engineering, vol. 62, pp. 741-745.
Jiang et al. "Comparative Studies on the Structures and Transition Characteristics of Poly(vinyl alcohol) (PVA) Modified with Polyethylene Glycol (PEG) by Chemical Bonding and Physical Blending Methods", Polymer Reprints, vol. 45, No. 1, pp. 919-920.
Zhu et al., "Poly(vinyl alcohol)-graft-poly(ethylene glycol) resins and their use in solid-phase synthesis and supported TEMPO catalysis", Chem. Comm., 2007, pp. 2136-2138.
International Search Report, International Application No. PCT/CA2007/001063, dated Sep. 26, 2007; completed Aug. 28, 2007.

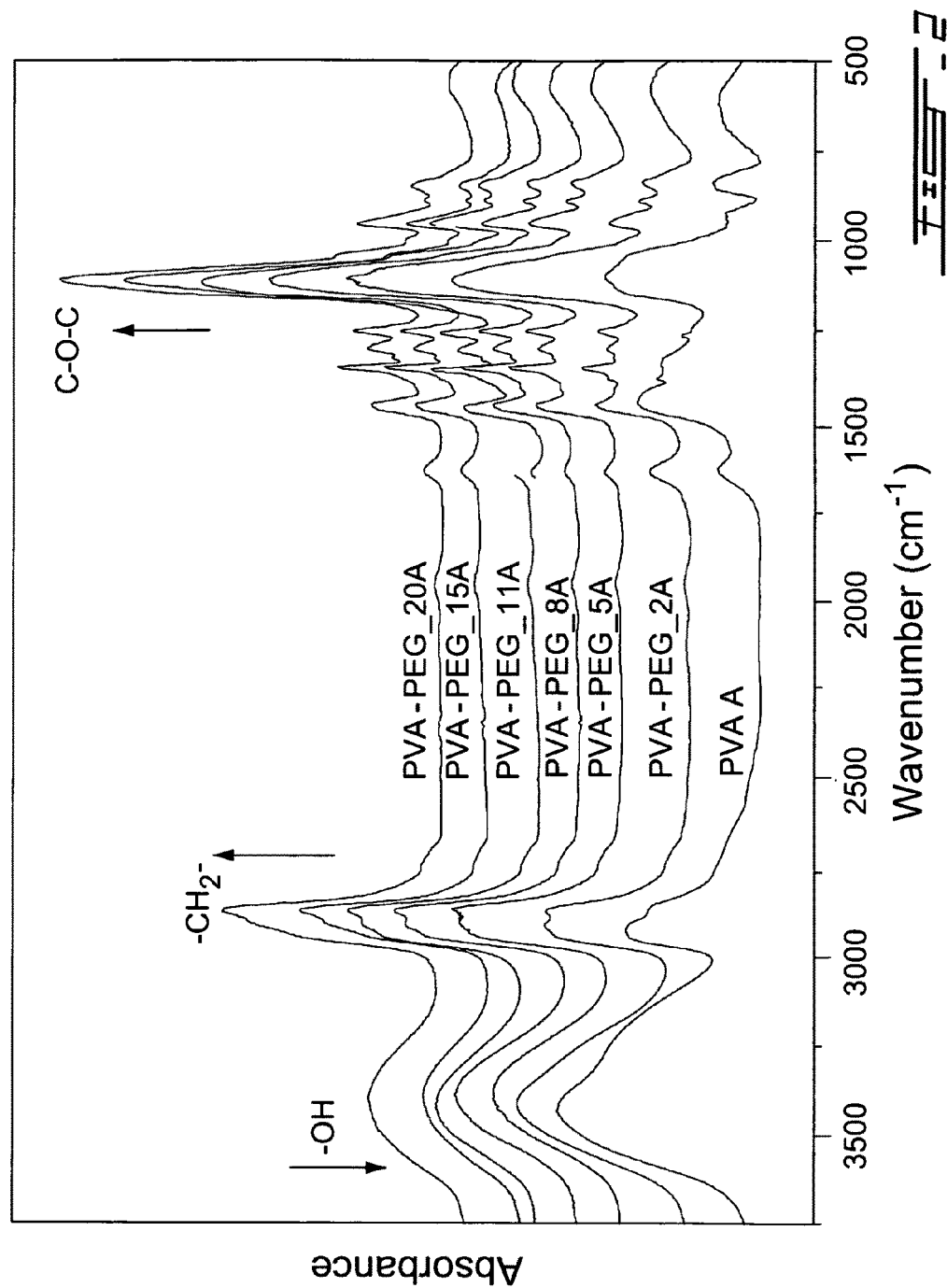

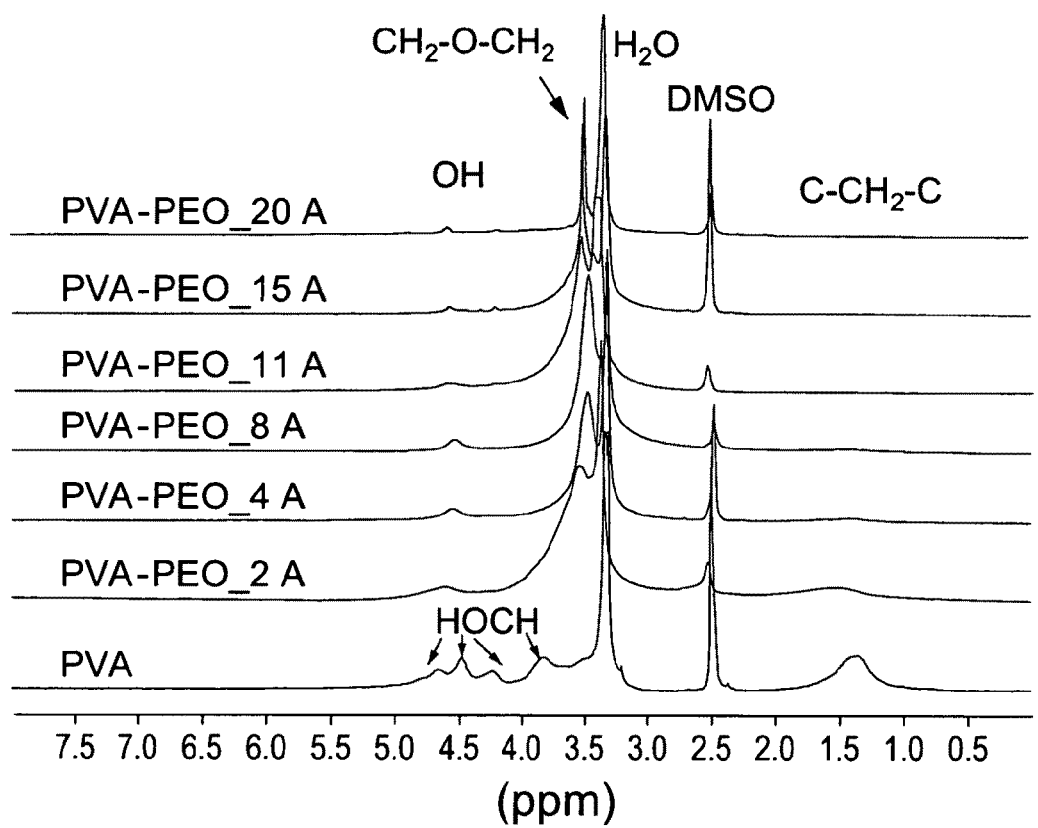

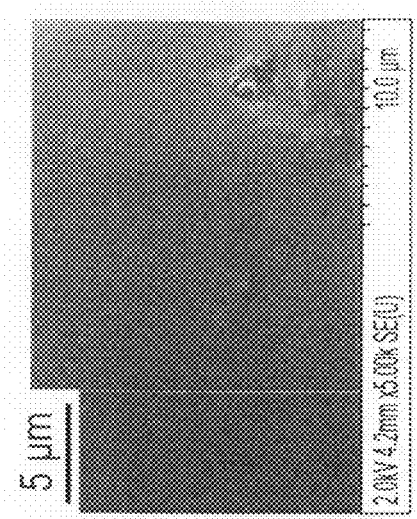 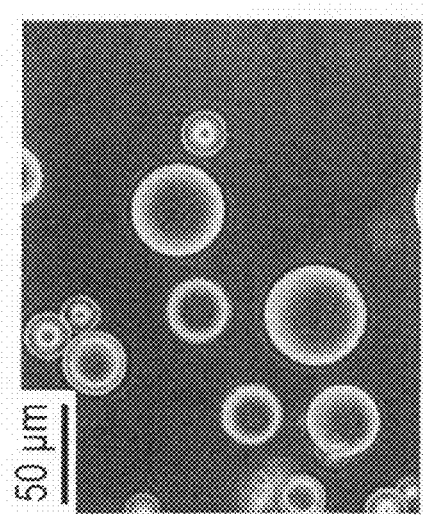
 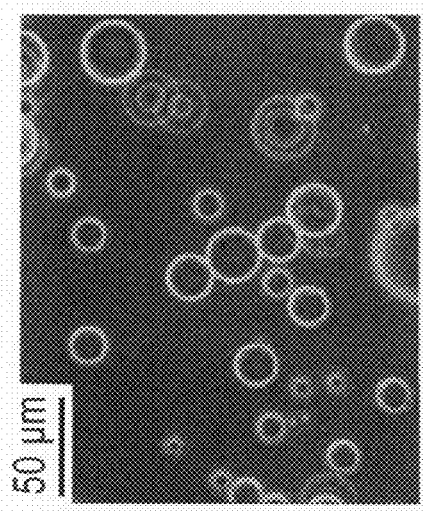
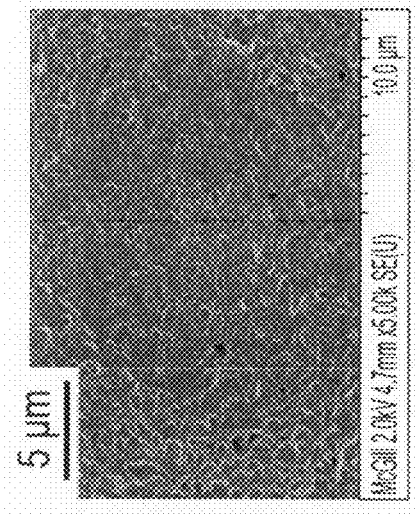 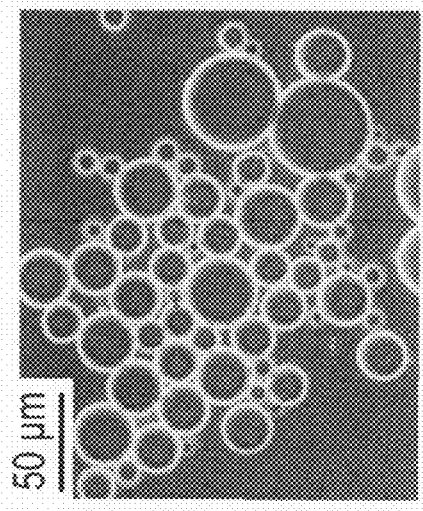
FIG. 5

POLY (VINYL ALCOHOL) POLYMERS, USES AND PREPARATION THEREOF

CROSS-REFERENCE TO RELATED APPLICATION

This application claims the benefit of U.S. provisional application No. 60/804,664 filed on Jun. 14, 2006 which is hereby incorporated by reference in its entirety.

FIELD OF THE INVENTION

The present invention relates to the field of organic chemistry. In particular, it relates to polymers such as poly(vinyl alcohol) polymers and copolymers containing vinyl alcohol or vinyl acetate and derivatives thereof, such as poly(ethylene glycol)-grafted poly(vinyl alcohol) polymers or polyether-grafted poly(vinyl alcohol) polymers and copolymers, that can be useful for various purposes in organic synthesis such as polymer support or resin.

BACKGROUND OF THE INVENTION

The interest of the pharmaceutical industry in combinatorial chemistry has driven increased research activity in solid-phase synthesis (Combinatorial Chemistry and Molecular Diversity in Drug Discovery Edited by Eric M. Gordon and James F. Kerwin, Jr. Wiley-Liss: New York. 1998. 516 pp. ISBN 0-47-15518-7.) to accomplish a wider range of chemistry. Similarly, new supported reagents and catalysts have emerged to facilitate the solution-phase synthesis and purification of compound library members. Crosslinked polystyrene-divinylbenzene (PS-DVB) matrices (Merrifield, R. B. *J. Am. Chem. Soc.* 1963, 85, 2149-2154) have been proven effective in solid-phase chemistry to produce peptides and small molecules, because of their relatively high functional group loading, reasonable swelling in selected solvents and mechanical stability. The hydrophobic polystyrene backbone has, however, poor compatibility with aqueous and polar solvents, potential reactivity under electrophilic chemical conditions, and is generally unsuitable for on-bead magic angle spinning (MAS) NMR analysis (Grotli, M.; Gotfredsen, C. H.; Rademann, J.; Buchardt, J.; Clark, A. J.; Duus, J. O.; Meldal, M. *J. Comb. Chem.* 2000, 2, 108-119). Several aqueous compatible resins have been prepared to overcome the shortcomings of the PS-DVB resins, including PEG-grafted crosslinked polystyrene resins, such as Tenta Gel (Rapp, W. In *Combinatorial Peptide and Nonpeptide Libraries: A Handbook*; Jung, G., Ed.; John Wiley & Sons: New York, 1998; pp 425-464) and ArgoGel (Labadie, J. W.; Deegan, T. L.; Gooding, O. W.; Heisler, K.; Newcomb, W. S.; Porco, J. A. Jr.; Tran, T. H.; Van Eikeren, P. Book of Abstracts, 212th ACS National Meeting, Orlando, Fla., Aug. 25-29 (1996)); as well as PEG cross-linked resins, such as PEGA (polyethylene glycol-dimethyacrylamide copolymer) (Renil, M.; Ferreras, M.; Delaisse, J. M.; Foged, N. T.; Meldal, M. *J. Pept. Sci.* 1998, 4, 195-210), POE-POP (polyoxyethylene-polyoxypropylene) (Renil, M.; Meldal, M. *Tetrahedron Lett.* 1996, 37, 6185-6188), Janda-Jel (Moss, J. A.; Dickerson, T. J.; Janda, K. D. *Tetrahedron Lett.* 2001, 43, 37-40), CLEAR (Cross-Linked Ethoxylate Acrylate Resins) (Kempe, M.; Barany, G. *J. Am. Chem. Soc.* 1996, 118, 7083-7093), and SPOCC (polyoxyethylene-polyoxetane) resins (Miranda, L. P.; Lubell, W. D.; Halkes, K. M.; Groth, T.; Grotli, M.; Rademann, J.; Gotfredsen, C. H.; Meldal, M. *J. Comb. Chem.* 2002, 4, 523-529). These resins typically possess poly(ethylene glycol) (PEG), which exhibits remarkable stability and good swelling in organic and aqueous media. Moreover, PEG-derived resins, such as Tenta Gel, PEGA, POE-POP, and SPOCC resins, all are generally suitable for MAS NMR analysis of resin-bound products (Grotli, M.; Goffredsen, C. H.; Rademann, J.; Buchardt, J.; Clark, A. J.; Duus, J. O.; Meldal, M. *J. Comb. Chem.* 2000, 2, 108-119).

The emergence of new strategies in combinatorial chemistry such as one-bead one-compound (Lam, K. S.; Salmon, S. E.; Hersh, E. M.; Hruby, V. J.; Kazmierski, W. M.; Knapp, R. J. *Nature* 1991, 354, 82-84) and on-bead screening of large compound libraries (Burger, M. T.; Bartlett, P. A. *J. Am. Chem. Soc.* 1977, 119, 12697-12698) requires new solid supports having high functional group loading and good swelling in a variety of solvents (Lam, K. S.; Lebl, M.; Krchnak, V. *Chem. Rev.* 1997, 97, 411-448). The functional group loading of most contemporary gel-type resins are normally between 0.2-0.4 mmol/g. Although dendrimer-based solid-phase supports have been prepared with higher functional group loading (Van Heerbeek, R.; Kamer, P. C. J.; Van Leeuwen, P. W. N. M.; Reek, J. N. H. *Chem. Rev.* 2002, 102(10), 3717-3756), their separation from the reaction media necessitates size exclusion chromatography. Moreover, the presence of amide and ester bonds within the dendrimer structure limits the chemistry, which can be performed on these supports (Lebreton, S.; Monaghan, S.; Bradley, M. *Aldrichimica Acta* 2001, 34, 75-83).

There was therefore a need for alternative resins that could have improved loading and swelling capacities as well as an enhanced stability.

SUMMARY OF THE INVENTION

In accordance with one aspect of the present invention there is provided a poly(vinyl alcohol)-graft-polyether polymer or a poly(vinyl alcohol)-graft-poly(ethylene glycol) polymer.

For example, the polymer can have a theoretical calculated hydroxyl group loading of at least 0.1 mmol/g, at least 2 mmol/g, at least 3 mmol/g, at least 5 mmol/g, at least 7 mmol/g, or at least 9 mmol/g. The polymer can also have a theoretical calculated hydroxyl group loading of about 0.1 mmol/g to about 20 mmol/g, about 1 mmol/g to about 10 mmol/g, or about 3 mmol/g to about 9 mmol/g. The polymer can have a titration calculated hydroxyl group loading of at least 0.1 mmol/g, at least 2 mmol/g, at least 3 mmol/g, at least 5 mmol/g, at least 7 mmol/g, or at least 9 mmol/g. The polymer can have a titration calculated hydroxyl group loading of about 0.1 mmol/g to about 15 mmol/g, about 2 mmol/g to about 10 mmol/g, or about 3 mmol/g to about 9 mmol/g. At least a portion of the hydroxyl groups of the poly(ethylene glycol) or polyether can be suitable for forming a covalent or non-covalent link with a substrate. The polymer can also be adapted for chemically bonding to a substrate by means of its hydroxyl groups so as to act as a solid support for the substrate. For example, at least a portion of the hydroxyl groups of the polyether or the poly(ethylene glycol) can be adapted to form a linkage with the substrate, the linkage being covalent or non-covalent.

In accordance with another aspect of the present invention there is provided a process for preparing a poly(vinyl alcohol)-graft-poly(ethylene glycol) polymer or a poly(vinyl alcohol)-graft-polyether polymer comprising grafting poly(ethylene glycol) or polyether chains on a poly(vinyl alcohol) polymer or a copolymer containing vinyl alcohol and/or vinyl acetate. For example, preformed poly(ethylene glycol) or polyether chains can be grafted on the poly(vinyl alcohol) polymer or a copolymer containing vinyl alcohol and/or vinyl acetate. The process can be carried out by reacting together a linear poly(ethylene glycol) polymer or a polyether polymer, a base (for example NaH), and a poly(vinyl alcohol) polymer or a copolymer containing vinyl alcohol and/or vinyl acetate in which at least a portion of the hydroxyl groups have been activated by a leaving group (for example a substituted sulfonyl such as p-toluenesulfonyl or methanesulfonyl). The process can also be carried out by reacting together a poly(vinyl alcohol) polymer or a copolymer containing vinyl alcohol and/or vinyl acetate, a base (for example NaOH) and a poly(ethylene glycol) polymer or a polyether polymer in which at least one of the hydroxyl groups has been replaced with a leaving group (for example Cl). The poly(ethylene glycol) or polyether chains can be made via a polymerization.

In accordance with another aspect of the present invention there is provided a process for preparing a poly(vinyl alcohol)-graft-poly(ethylene glycol) polymer or a poly(vinyl alcohol)-graft-polyether polymer comprising reacting together a poly(vinyl alcohol) polymer or a copolymer containing vinyl alcohol and/or vinyl acetate, a base and an ether (such as ethylene oxide or oxetane or propylene oxide or a derivative thereof) or a diol. The reaction can be carried out in a pressure reactor. The temperature can be of at least 50° C. or of at least 100° C. For example, the base can be NaOH or KOH.

In accordance with another aspect of the present invention there is provided a process for preparing a poly(vinyl alcohol)-graft-poly(ethylene glycol) polymer or a poly(vinyl alcohol)-graft-polyether polymer comprising reacting together a poly(vinyl alcohol) polymer or a copolymer containing vinyl alcohol and/or vinyl acetate, a polymerization initiator and an ether such as ethylene oxide or oxetane or propylene oxide or a diol. The reaction can be carried out in the presence of dimethylsulfoxide. The polymerization initiator can be chosen from potassium napthalene (potassium naphthenylide), potassium metal, sodium metal, an alkoxide such as but not limited to KOR, NaOR or LiOR where R is a linear or branched alkyl group of 1-10 carbons, a metal hydride, such as but not limited to KH, NaH LiH, an amide base such as but not limited to NaNH2, LiN(iPr)2, KN(Si(Me)3)2, supramolecular complexes of potassium methoxide and potassium hydroxide with 18-crown-6 (see Synthesis of Poly(2-methyl-3-hydroxyoctanoate) via Anionic Polymerization of -Methyl-pentyl-propiolactone Arkin, A. H.; Hazer, B.; Adamus, G.; Kowalczuk, M.; Jedlinski, Z.; Lenz, R. W. Biomacromolecules; (Communication); 2001; 2(3); 623-627), organometallic reagents such as sec-Butyllithium, tert-butyllithium and cumylpotassium. The initiator and the poly(vinyl alcohol) polymer or a copolymer containing vinyl alcohol and/or vinyl acetate can be reacted together so as to activate the polymer and then, the ether or diol can be reacted with the activated polymer. The initiator and the poly(vinyl alcohol) polymer or a copolymer containing vinyl alcohol and/or vinyl acetate can be reacted together thereby providing a mixture, and then, the ether or diol can be reacted with the mixture.

In accordance with another aspect of the present invention there is provided a poly(vinyl alcohol)-graft-poly(ethylene glycol) or polyether polymer obtained by reacting together a poly(vinyl alcohol) polymer or a copolymer containing vinyl alcohol and/or vinyl acetate, a polymerization initiator and an ether such as ethylene oxide or oxetane or propylene oxide, or a diol. The reaction can be carried out in the presence of dimethylsulfoxide. The polymerization initiator can be chosen from potassium naphthalide, potassium metal, sodium metal, an alkoxide such as but not limited to KOR, NaOR or LiOR where R is a linear or branched alkyl group of 1-10 carbons, a metal hydride, such as but not limited to KH, NaH LiH, an amide base such as but not limited to NaNH2, LiN(iPr)2, KN(Si(Me)3)2, supramolecular complexes of potassium methoxide and potassium hydroxide with 18-crown-6 (see Synthesis of Poly(2-methyl-3-hydroxyoctanoate) via Anionic Polymerization of -Methyl-pentyl-propiolactone Arkin, A. H.; Hazer, B.; Adamus, G.; Kowalczuk, M.; Jedlinski, Z.; Lenz, R. W. Biomacromolecules; (Communication); 2001; 2(3); 623-627), organometallic reagents such as sec-butyllithium, tert-butyllithium and cumylpotassium In accordance with another aspect of the present invention there is provided a compound of formula:

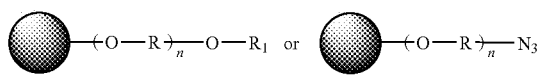

wherein

represents a poly(vinyl alcohol) polymer or a copolymer containing vinyl alcohol and/or vinyl acetate;

—(—O—R—)$_n$—O—R$_1$, represents a plurality of poly(ethylene glycol) or polyether chains that are attached to the poly(vinyl alcohol) polymer or a copolymer containing vinyl alcohol and/or vinyl acetate, each of the chains independently comprising n repeating units;

—(—O—R—)$_n$—N$_3$ represents a plurality of poly(ethylene glycol) or polyether chains that are attached to said poly(vinyl alcohol) polymer or a copolymer containing vinyl alcohol and/or vinyl acetate, each of said chains independently comprising n repeating units n having a value of about 1 to about 100;

R is an alkyl group and include, without limitation, $(CH_2)_m$, $(CH_2CHR_3)_m$, $(CHR_3—CHR_4)_m$, where m=1 to 12;

R$_1$ is H, —(C=O)—R$_2$, —(C=S)—R$_2$, —S(O$_2$)R$_3$, —CH$_2$COH, —CH$_2$CO$_2$H, —CH$_2$(C=O)SH, —CH$_2$(C=S)OH, —CH$_2$CONR$_4$R$_5$, —CH$_2$CSNR$_4$R$_5$, —CH$_2$CON$_3$, —CH$_2$CH$_2$OH, —CH$_2$CH$_2$N$_2$, a peptide or a derivative thereof, an oligonucleotide or a derivative thereof, a carbohydrate or a derivative thereof, a glycopeptide or a derivative thereof, a protecting group suitable for a hydroxyl group, a suitable leaving group derivative, a catalyst or a derivative thereof, a substrate for an enzyme, a ligand for a receptor, a derivative of a catalytic reagent such as TEMPO and as hydroxyproline, an analog of a trialkyl phosphine, $C_1$-$C_{20}$ alkyl linear or branched, $C_3$-$C_{12}$ cycloalkyl, $C_1$-$C_{12}$ heterocyclyl, $C_2$-$C_{20}$ alkylheterocyclyl, $C_2$-$C_{20}$ alkenyl, $C_2$-$C_{20}$ alkynyl, $C_6$-$C_{12}$ aryl, $C_6$-$C_{20}$ aralkyl, $C_6$-$C_{20}$ alkylaryl, $C_1$-$C_{12}$ heteroaryl, $C_2$-$C_{20}$ alkylheteroaryl,

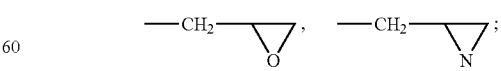

R$_2$ is H, OH, NR$_4$R$_5$, $C_1$-$C_{20}$ alkyl linear or branched, $C_3$-$C_{12}$ cycloalkyl, $C_1$-$C_{12}$ heterocyclyl, $C_2$-$C_{20}$ alkenyl, $C_2$-$C_{20}$ alkynyl, $C_6$-$C_{12}$ aryl, $C_6$-$C_{20}$ aralkyl, $C_6$-$C_{20}$ alkylaryl, $C_2$-$C_{20}$ alkylheterocyclyl, $C_1$-$C_{12}$ heteroaryl, or $C_2$-$C_{20}$ alkylheteroaryl;

$R_3$ is OH, $NR_4R_5$, $C_1$-$C_{20}$ alkyl linear or branched, $C_3$-$C_{12}$ cycloalkyl, $C_1$-$C_{12}$ heterocyclyl, $C_2$-$C_{20}$ alkenyl, $C_2$-$C_{20}$ alkynyl, $C_6$-$C_{12}$ aryl, $C_6$-$C_{20}$ aralkyl, $C_6$-$C_{20}$ alkylaryl, $C_2$-$C_{20}$ alkylheterocyclyl, $C_1$-$C_{12}$ heteroaryl, or $C_2$-$C_{20}$ alkylheteroaryl; —$CH_3$, or -p-$C_6H_5CH_3$;

$R_4$ is a hydrogen atom, a $C_1$-$C_{20}$ alkyl linear or branched, $C_3$-$C_{12}$ cycloalkyl, $C_1$-$C_{12}$ heterocyclyl, $C_2$-$C_{20}$ alkenyl, $C_2$-$C_{20}$ alkynyl, $C_6$-$C_{12}$ aryl, $C_6$-$C_{20}$ aralkyl, $C_6$-$C_{20}$ alkylaryl, $C_1$-$C_{12}$ heteroaryl, $C_2$-$C_{20}$ alkylheterocyclyl, $C_2$-$C_{20}$ alkylheteroaryl, or a suitable protecting group for an amino group; and $R_5$ is a hydrogen atom, a $C_1$-$C_{20}$ alkyl linear or branched, $C_3$-$C_{12}$ cycloalkyl, $C_1$-$C_{12}$ heterocyclyl, $C_2$-$C_{20}$ alkenyl, $C_2$-$C_{20}$ alkynyl, $C_6$-$C_{12}$ aryl, $C_6$-$C_{20}$ aralkyl, $C_6$-$C_{20}$ alkylaryl, $C_1$-$C_{12}$ heteroaryl, $C_2$-$C_{20}$ alkylheterocyclyl, $C_2$-$C_{20}$ alkylheteroaryl, or a suitable protecting group for an amino group;

the alkyl, cycloalkyl, heterocyclyl, alkenyl, alkynyl, aryl, aralkyl, alkylaryl, heteroaryl, alkylheterocyclyl, and alkylheteroaryl are unsubstituted or substituted with at least one substituent, each of the substituent(s) being chosen from F, Cl, Br, I, OH, SH, $NH_2$, $NO_2$, CN, $CF_3$, —SH, —$OCH_2Ph$, —OPh, —$SCH_3$, —SPh, —$SCH_2Ph$, —COOH, —$COOR_2$, $C_1$-$C_{12}$ alkyl linear or branched, $C_6$-$C_{12}$ aryl, $C_2$-$C_{20}$ alkenyl, $C_1$-$C_{20}$ alkoxy, $C_1$-$C_{20}$ alkyl, $C_2$-$C_{20}$ alkynyl, $C_6$-$C_{20}$ aralkyl, $C_6$-$C_{12}$ aryl, $C_3$-$C_8$ cycloalkyl, $C_1$-$C_{20}$ aminoalkyl, $C_6$-$C_{12}$ aminoaryl, $C_1$-$C_{12}$ aminoheteroaryl, $C_1$-$C_{20}$ hydroxyalkyl, $C_6$-$C_{12}$ hydroxyaryl, $C_1$-$C_{12}$ hydroxyheteroaryl, $C_1$-$C_{12}$ heterocyclyl, $C_1$-$C_{12}$ heteroaryl, $C_2$-$C_{20}$ alkylheterocyclyl, or $C_2$-$C_{20}$ alkylheteroaryl.

For example, $R_1$ can be a catalyst chosen from TEMPO or a derivative thereof, a suitably modified transition metal catalyst such as a Rh- or Ru-phosphine analog, an analog of an organic catalyst such as a secondary amine, a thiazolium or imidazolium salt, or a proline analog, or an analog of cyclo[(S)-phenylalaninyl-(S)-histidinyl], or an analog of a cinchona alkaloid, or a derivative of poly(L-leucine), or a derivative thereof which comprises a linking moiety disposed between the compound and the catalyst.

For example, the leaving group derivative can be chosen from F, Cl, Br, I, —$CH_3$, —$SO_2CH_3$, —$COCH_3$, or —$SO_2$-p-$C_6H_5CH_3$.

For example, the protecting group for a hydroxyl group can be chosen from trimethylsilyl, triethylsilyl, t-butyldimethylsilyl, tetrahydropyran, benzyl, allyl, $C_1$-$C_6$ alkyne, substituted benzyl, acyl i.e. acetyl, benzoyl, Boc, Fmoc.

$R_1$ can also be of formula -L-T, wherein L is a bond or a linker and T is an amino acid or a derivative thereof.

In accordance with another aspect of the present invention there is provided a compound of formula:

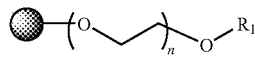

wherein

represents a poly(vinyl alcohol) polymer or a copolymer containing vinyl alcohol and/or vinyl acetate;

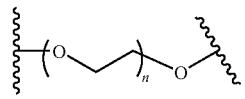

represents a plurality of poly(ethylene glycol) or polyether chains that are attached to the poly(vinyl alcohol) polymer or a copolymer containing vinyl alcohol and/or vinyl acetate, each of the chains independently comprising n repeating units;

n having a value of about 1 to about 100;

$R_1$ is H, —(C=O)—$R_2$, —(C=S)—$R_2$, —$S(O_2)R_3$, —$CH_2COH$, —$CH_2CO_2H$, —$CH_2(C=O)SH$, —$CH_2(C=S)OH$, —$CH_2CONR_4R_5$, —$CH_2CSNR_4R_5$, —$CH_2CON_3$, —$CH_2CH_2OH$, —$CH_2CH_2N_2$, a peptide or a derivative thereof, an oligonucleotide or a derivative thereof, a carbohydrate or a derivative thereof, a glycopeptide or a derivative thereof, a protecting group suitable for a hydroxyl group, a suitable leaving group derivative, a catalyst or a derivative thereof, a substrate for an enzyme, a ligand for a receptor, a derivative of a catalytic reagent such as TEMPO, an analog of a trialkyl phosphine, $C_1$-$C_{20}$ alkyl linear or branched, $C_3$-$C_{12}$ cycloalkyl, $C_1$-$C_{12}$ heterocyclyl, $C_2$-$C_{20}$ alkylheterocyclyl, $C_2$-$C_{20}$ alkenyl, $C_2$-$C_{20}$ alkynyl, $C_6$-$C_{12}$ aryl, $C_6$-$C_{20}$ aralkyl, $C_6$-$C_{20}$ alkylaryl, $C_1$-$C_{12}$ heteroaryl, $C_2$-$C_{20}$ alkylheteroaryl,

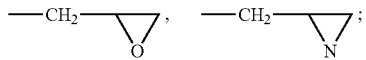

$R_2$ is H, OH, $NR_4R_5$, $C_1$-$C_{20}$ alkyl linear or branched, $C_3$-$C_{12}$ cycloalkyl, $C_1$-$C_{12}$ heterocyclyl, $C_2$-$C_{20}$ alkenyl, $C_2$-$C_{20}$ alkynyl, $C_6$-$C_{12}$ aryl, $C_6$-$C_{20}$ aralkyl, $C_6$-$C_{20}$ alkylaryl, $C_2$-$C_{20}$ alkylheterocyclyl, $C_1$-$C_{12}$ heteroaryl, or $C_2$-$C_{20}$ alkylheteroaryl;

$R_3$ is OH, $NR_4R_5$, $C_1$-$C_{20}$ alkyl linear or branched, $C_3$-$C_{12}$ cycloalkyl, $C_1$-$C_{12}$ heterocyclyl, $C_2$-$C_{20}$ alkenyl, $C_2$-$C_{20}$ alkynyl, $C_6$-$C_{12}$ aryl, $C_6$-$C_{20}$ aralkyl, $C_6$-$C_{20}$ alkylaryl, $C_2$-$C_{20}$ alkylheterocyclyl, $C_1$-$C_{12}$ heteroaryl, or $C_2$-$C_{20}$ alkylheteroaryl; —$CH_3$, or -p-$C_6H_5CH_3$;

$R_4$ is a hydrogen atom, a $C_1$-$C_{20}$ alkyl linear or branched, $C_3$-$C_{12}$ cycloalkyl, $C_1$-$C_{12}$ heterocyclyl, $C_2$-$C_{20}$ alkenyl, $C_2$-$C_{20}$ alkynyl, $C_6$-$C_{12}$ aryl, $C_6$-$C_{20}$ aralkyl, $C_6$-$C_{20}$ alkylaryl, $C_1$-$C_{12}$ heteroaryl, $C_2$-$C_{20}$ alkylheterocyclyl, $C_2$-$C_{20}$ alkylheteroaryl, or a suitable protecting group for an amino group; and $R_5$ is a hydrogen atom, a $C_1$-$C_{20}$ alkyl linear or branched, $C_3$-$C_{12}$ cycloalkyl, $C_1$-$C_{12}$ heterocyclyl, $C_2$-$C_{20}$ alkenyl, $C_2$-$C_{20}$ alkynyl, $C_6$-$C_{12}$ aryl, $C_6$-$C_{20}$ aralkyl, $C_6$-$C_{20}$ alkylaryl, $C_1$-$C_{12}$ heteroaryl, $C_2$-$C_{20}$ alkylheterocyclyl, $C_2$-$C_{20}$ alkylheteroaryl, or a suitable protecting group for an amino group;

the alkyl, cycloalkyl, heterocyclyl, alkenyl, alkynyl, aryl, aralkyl, alkylaryl, heteroaryl, alkylheterocyclyl, and alkylheteroaryl are unsubstituted or substituted with at least one substituent, each of the substituent(s) being chosen from F, Cl, Br, I, OH, SH, $NH_2$, $NO_2$, CN, $CF_3$, —SH, —$OCH_2Ph$, —OPh, —$SCH_3$, —SPh, —$SCH_2Ph$, —COOH, —$COOR_2$, $C_1$-$C_{12}$ alkyl linear or branched, $C_6$-$C_{12}$ aryl, $C_2$-$C_{20}$ alkenyl, $C_1$-$C_{20}$ alkoxy, $C_1$-$C_{20}$ alkyl, $C_2$-$C_{20}$ alkynyl, $C_6$-$C_{20}$ aralkyl, $C_6$-$C_{12}$ aryl, $C_3$-$C_8$ cycloalkyl, $C_1$-$C_{20}$ aminoalkyl, $C_6$-$C_{12}$ aminoaryl, $C_1$-$C_{12}$ aminoheteroaryl, $C_1$-$C_{20}$ hydroxyalkyl, $C_6$-$C_{12}$ hydroxyaryl, $C_1$-$C_{12}$ hydroxyheteroaryl, $C_1$-$C_{12}$ heterocyclyl, $C_1$-$C_{12}$ heteroaryl, $C_2$-$C_{20}$ alkylheterocyclyl, or $C_2$-$C_{20}$ alkylheteroaryl.

For example, $R_1$ can be a catalyst chosen from TEMPO or a derivative thereof, a suitably modified transition metal catalyst such as a Rh- or Ru-phosphine analog, an analog of an organic catalyst such as a secondary amine, a thiazolium or imidazolium salt, or a proline analog, or an analog of cyclo[(S)-phenylalaninyl-(S)-histidinyl], or an analog of a cinchona alkaloid, or a derivative of poly(L-leucine), or a derivative thereof which comprises a linking moiety disposed between the compound and the catalyst.

For example, the leaving group derivative can be chosen from F, Cl, Br, I, —CH$_3$, —SO$_2$CH$_3$, —COCH$_3$, or —SO$_2$-p-C$_6$H$_5$CH$_3$.

For example, the protecting group for a hydroxyl group can be chosen from trimethylsilyl, triethylsilyl, t-butyldimethylsilyl, tetrahydropyran, benzyl, allyl, C$_1$-C$_6$ alkyne, substituted benzyl, acyl, i.e. acetyl, benzoyl, Boc, Fmoc.

R$_1$, can also be of formula -L-T, wherein L is a bond or a linker and T is an amino acid or a derivative thereof.

In accordance with another aspect of the present invention there is provided a compound of formula:

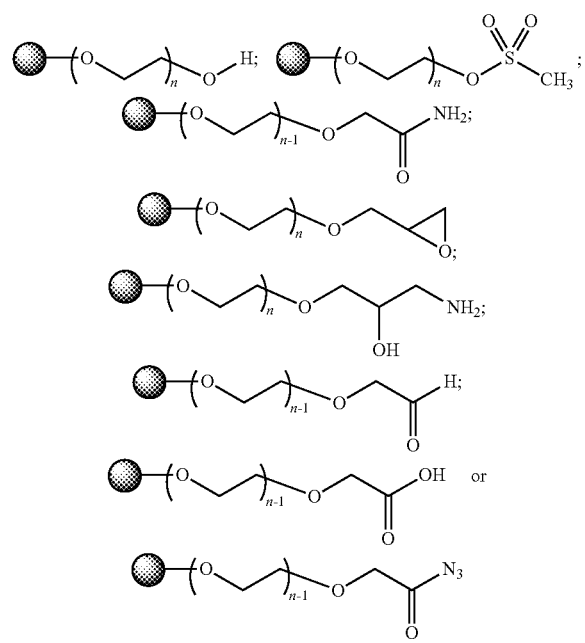

wherein

represents a poly(vinyl alcohol) polymer or a copolymer containing vinyl alcohol and/or vinyl acetate;

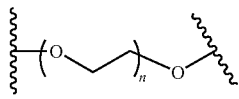

represents a plurality of unsubstituted or substituted poly(ethylene glycol) or polyether chains that are attached to the poly(vinyl alcohol) polymer or a copolymer containing vinyl alcohol and/or vinyl acetate, each of the chains independently comprising n repeating units;

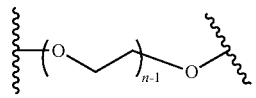

represents a plurality of substituted poly(ethylene glycol) or polyether chains that are attached to the poly(vinyl alcohol) polymer or a copolymer containing vinyl alcohol and/or vinyl acetate, each of the chains independently comprising n−1 repeating units;

n having a value of about 2 to about 50.

In accordance with another aspect of the present invention there is provided a compound of formula:

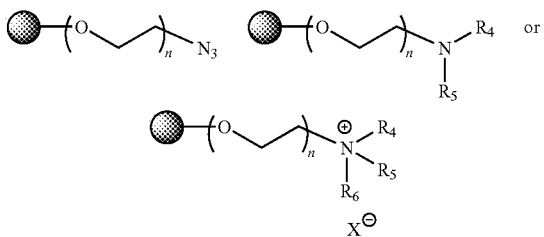

wherein

represents a poly(vinyl alcohol) polymer or a copolymer containing vinyl alcohol and/or vinyl acetate;

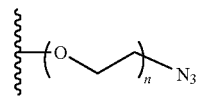

represents a plurality of modified poly(ethylene glycol) or polyether chains, these modified poly(ethylene glycol) or polyether chains are attached to the poly(vinyl alcohol) polymer or a copolymer containing vinyl alcohol and/or vinyl acetate, each of the chains independently comprising n repeating units;

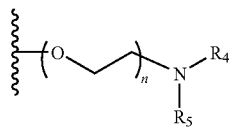

represents a plurality of modified poly(ethylene glycol) or polyether chains, these modified poly(ethylene glycol) or polyether chains are attached to the poly(vinyl alcohol) polymer or a copolymer containing vinyl alcohol and/or vinyl acetate, each of the chains independently comprising n repeating units;

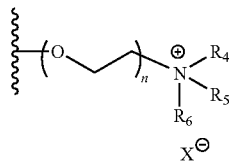

represents a plurality of modified poly(ethylene glycol) or polyether chains, these modified poly(ethylene glycol) or polyether chains are attached to the poly(vinyl alcohol) polymer or a copolymer containing vinyl alcohol and/or vinyl acetate, each of the chains independently comprising n repeating units;

n having a value of about 2 to about 50;

R$_4$ is a hydrogen atom, a C$_1$-C$_{20}$ alkyl linear or branched, C$_3$-C$_{12}$ cycloalkyl, C$_1$-C$_{12}$ heterocyclyl, C$_2$-C$_{20}$ alkenyl, C$_2$-C$_{20}$ alkynyl, C$_6$-C$_{12}$ aryl, C$_6$-C$_{20}$ aralkyl, C$_6$-C$_{20}$ alkylaryl, C$_1$-C$_{12}$ heteroaryl, C$_2$-C$_{20}$ alkylheterocyclyl, C$_2$-C$_{20}$ alkylheteroaryl, or a suitable protecting group for an amino group, a peptide or derivative thereof such as a peptidomimetic, an acyl group i.e. acetyl, benzoyl or phenylacetyl, a carbohydrate or derivative thereof, a nucleotide or derivative thereof, a linker for peptide synthesis such as a Wang or Knorr linker;

$R_5$ is a hydrogen atom, a $C_1$-$C_{20}$ alkyl linear or branched, $C_3$-$C_{12}$ cycloalkyl, $C_1$-$C_{12}$ heterocyclyl, $C_2$-$C_{20}$ alkenyl, $C_2$-$C_{20}$ alkynyl, $C_6$-$C_{12}$ aryl, $C_6$-$C_{20}$ aralkyl, $C_6$-$C_{20}$ alkylaryl, $C_1$-$C_{12}$ heteroaryl, $C_2$-$C_{20}$ alkylheterocyclyl, $C_2$-$C_{20}$ alkylheteroaryl, or a suitable protecting group for an amino group, a peptide or derivative thereof such as a peptidomimetic, an acyl group i.e. acetyl, benzoyl or phenylacetyl, a carbohydrate or derivative thereof, a nucleotide or derivative thereof, a linker for peptide synthesis such as a Wang or Knorr linker;

or $R_4$ and $R_5$ are joined together to form a $C_1$-$C_{12}$ heterocycyl or a $C_1$-$C_{12}$ heteroaryl;

$R_6$ is a hydrogen atom, a $C_1$-$C_{20}$ alkyl linear or branched, $C_3$-$C_{12}$ cycloalkyl, $C_1$-$C_{12}$ heterocyclyl, $C_2$-$C_{20}$ alkenyl, $C_2$-$C_{20}$ alkynyl, $C_6$-$C_{12}$ aryl, $C_6$-$C_{20}$ aralkyl, $C_6$-$C_{20}$ alkylaryl, $C_1$-$C_{12}$ heteroaryl, $C_2$-$C_{20}$ alkylheterocyclyl, $C_2$-$C_{20}$ alkylheteroaryl, or a suitable protecting group for an amino group, a peptide or derivative thereof such as a peptidomimetic, an acyl group i.e. acetyl, benzoyl or phenylacetyl, a carbohydrate or derivative thereof, a nucleotide or derivative thereof, a linker for peptide synthesis such as a Wang or Knorr linker;

$X^-$ can be any type of anion. It can be an organic anion or an inorganic anion. $X^-$ can be chosen from $F^-$, $Cl^-$, $Br^-$, $I^-$, $OH^-$, $ClO_4^-$, $PF_6^-$, $N_3^-$, $BF_4^-$, $SbF_6^-$, $BH_4^-$, $(FSO_2)_2N^-$, $(CF_3SO_2)_2N^-$, $(C_2F_5SO_2)_2N^-$, $(CF_3SO_2)_3C^-$, $CF_3SO_3^-$, $CF_3COO^-$, $AsF_6^-$, $CH_3COO^-$, $(CN)_2N^-$, $NO_3^-$, phosphates, sulfates, nitrates, carbonates, carboxylates, periodates, carboxylic acids (for example $C_1$-$C_{20}$ carboxylic acids), sulfonic acids (for example $C_1$-$C_{20}$ sulfonic acids), amino acids protected or not and derivatives thereof, when possible the previously mentioned anions can optionally be chiral.

the alkyl, cycloalkyl, heterocyclyl, alkenyl, alkynyl, aryl, aralkyl, alkylaryl, heteroaryl, alkylheterocyclyl, and alkylheteroaryl are unsubstituted or substituted with at least one substituent, each of the substituent(s) being chosen from F, Cl, Br, I, OH, SH, $NH_2$, $NO_2$, CN, $CF_3$, —SH, —$OCH_2Ph$, —OPh, —$SCH_3$, —SPh, —$SCH_2Ph$, —COOH, —$COOR_2$, $C_1$-$C_{12}$ alkyl linear or branched, $C_6$-$C_{12}$ aryl, $C_2$-$C_{20}$ alkenyl, $C_1$-$C_{20}$ alkoxy, $C_1$-$C_{20}$ alkyl, $C_2$-$C_{20}$ alkynyl, $C_6$-$C_{20}$ aralkyl, $C_6$-$C_{12}$ aryl, $C_3$-$C_8$ cycloalkyl, $C_1$-$C_{20}$ aminoalkyl, $C_6$-$C_{12}$ aminoaryl, $C_1$-$C_{12}$ aminoheteroaryl, $C_1$-$C_{20}$ hydroxyalkyl, $C_6$-$C_{12}$ hydroxyaryl, $C_1$-$C_{12}$ hydroxyheteroaryl, $C_1$-$C_{12}$ heterocyclyl, $C_1$-$C_{12}$ heteroaryl, $C_2$-$C_{20}$ alkylheterocyclyl, or $C_2$-$C_{20}$ alkylheteroaryl, an amino acid or a derivative thereof, a peptide or a derivative thereof, a protein or a derivative thereof, a carbohydrate or a derivative thereof, a nucleotide or a derivative thereof, an oligonucleotide or a derivative thereof, and an enzyme or a derivative thereof.

The leaving group derivative can be chosen from F, Cl, Br, I, —$CH_3$, —$SO_2CH_3$, —$COCH_3$, —$SO_2$-p-$C_6H_5$ and —$SO_2$-p-$C_6H_4CH_3$.

For example, the compound can be:

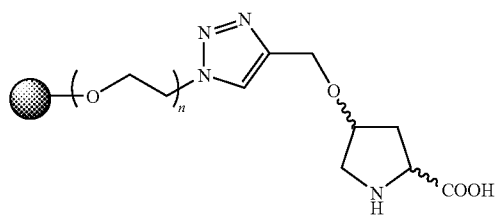

or any stereoisomer thereof.

According to another embodiment, the compound can also be:

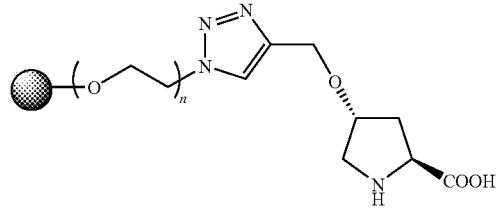

In accordance with another aspect of the present invention there is provided a compound of formula:

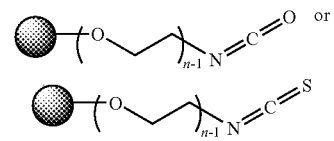

wherein

represents a poly(vinyl alcohol) polymer or a copolymer containing vinyl alcohol and/or vinyl acetate;

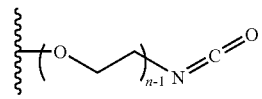

represents a plurality of modified poly(ethylene glycol) or polyether chains, these modified poly(ethylene glycol) or polyether chains are attached to the poly(vinyl alcohol) polymer or a copolymer containing vinyl alcohol and/or vinyl acetate, each of the chains independently comprising n repeating units;

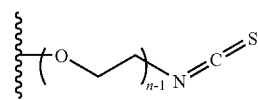

represents a plurality of modified poly(ethylene glycol) or polyether chains, these modified poly(ethylene glycol) or polyether chains are attached to the poly(vinyl alcohol) polymer or a copolymer containing vinyl alcohol and/or vinyl acetate, each of the chains independently comprising n repeating units; and n having a value of about 2 to about 49;

the alkyl, cycloalkyl, heterocyclyl, alkenyl, alkynyl, aryl, aralkyl, alkylaryl, heteroaryl, alkylheterocyclyl, and alkylheteroaryl are unsubstituted or substituted with at least one substituent, each of the substituent(s) being chosen from F, Cl, Br, I, OH, SH, $NH_2$, $NO_2$, CN, $CF_3$, —SH, —$OCH_2Ph$, —OPh, —$SCH_3$, —SPh, —$SCH_2Ph$, —COOH, —$COOR_2$, $C_1$-$C_{12}$ alkyl linear or branched, $C_6$-$C_{12}$ aryl, $C_2$-$C_{20}$ alkenyl, $C_1$-$C_{20}$ alkoxy, $C_1$-$C_{20}$ alkyl, $C_2$-$C_{20}$ alkynyl, $C_6$-$C_{20}$ aralkyl, $C_6$-$C_{12}$ aryl, $C_3$-$C_8$ cycloalkyl, $C_1$-$C_{20}$ aminoalkyl, $C_6$-$C_{12}$ aminoaryl, $C_1$-$C_{12}$ aminoheteroaryl, $C_1$-$C_{20}$ hydroxyalkyl, $C_6$-$C_{12}$ hydroxyaryl, $C_1$-$C_{12}$ hydroxyheteroaryl, $C_1$-$C_{12}$ heterocyclyl, $C_1$-$C_{12}$ heteroaryl, $C_2$-$C_{20}$ alkylheterocyclyl, or $C_2$-$C_{20}$ alkylheteroaryl.

In accordance with another aspect of the present invention there is provided a compound of formula

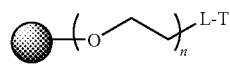

wherein

represents a poly(vinyl alcohol) polymer or a copolymer containing vinyl alcohol and/or vinyl acetate;

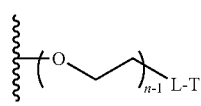

represents a plurality of modified poly(ethylene glycol) or polyether chains, these modified poly(ethylene glycol) or polyether chains are attached to the poly(vinyl alcohol) polymer or a copolymer containing vinyl alcohol and/or vinyl acetate, each of the chains independently comprising n repeating units;

n has a value of about 2 to about 50;

L is a bond or a linker; and

T is an amino acid or a derivative thereof.

In the compounds of the present invention, L can be various types of linkers chosen from heterocycle linkers, Wang esters, Wang amides Knorr linker, photocleavable linkers, silyl linkers, and derivative thereof.

For example, such linkers can be

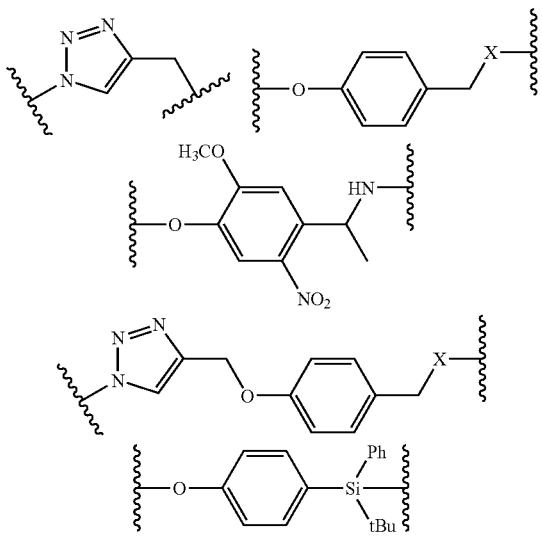

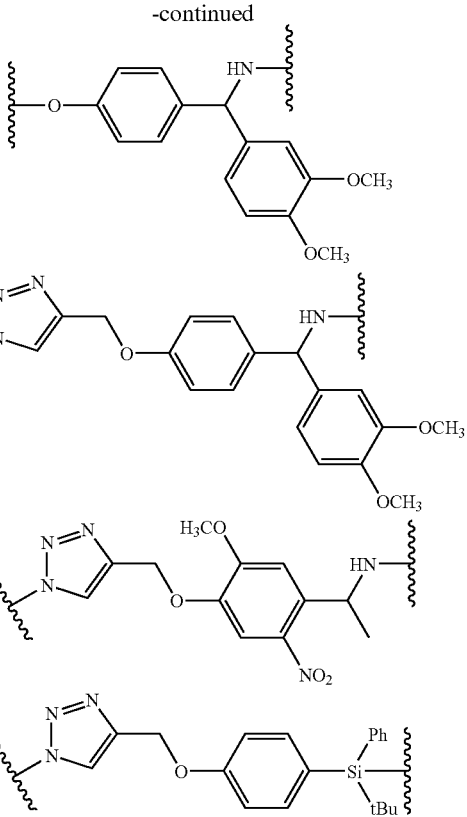

X = O or NH

L can also be a $C_1$-$C_{20}$ alkylene for example $(CH_2)_m$, $(CH_2CHR_3)_m$, $(CHR_3—CHR_4)_m$, where m=1 to 12, $C_2$-$C_{20}$ alkenylene, or $C_2$-$C_{20}$ alkynylene.

T can be various types of amino acids and derivatives thereof. For example, T can be chosen from proline, 4-hydroxyproline, serine, histidine, aspartate, glutamate, ornithine, lysine, alanine, leucine, tyrosine, arginine, 4-hydroxyprolinamide, 4-hydroxyproline esters, prolylpeptides, 4-hydroxyproline tetrazole, hydroxyaminoacids, stereoisomers thereof, and salts thereof. Derivatives of amino acids include various possibilities of substitutions including addition of a linker to the amino acid.

In accordance with another aspect of the present invention, there is provided a method for using a polymer as previously defined or a compound as previously defined. The method comprises attaching a substrate to the polymer or compound, then modifying the substrate. The method can further comprise removing the modified substrate from the polymer or compound. The substrate can have a reactive portion adapted for attaching to the polymer or compound, and a protected portion. The substrate can be attached to the polymer or compound via the reactive portion. The protected portion of the substrate attached to the polymer or compound can be deprotected before the substrate is treated, so as to be modified. The method can further comprise recycling the polymer or compound.

In accordance with another aspect of the present invention, there is provided a method for using a polymer as previously defined or a compound as previously defined. The method comprises attaching, to the polymer or compound, a substrate, for example, a catalyst or a derivative thereof, or a ligand or a derivative thereof. The method can also comprise using the so obtained compound in an organic synthesis.

In accordance with another aspect of the present invention, there is provided a method for using a polymer as previously defined or a compound as previously defined, the method comprising:

a) attaching a substrate to the polymer or compound, the substrate having a reactive portion adapted to be attached to the polymer or compound, and a protected portion, the substrate being attached to the polymer or compound via its reactive portion;

b) deprotecting the protected portion; and c) attaching another substrate to the deprotected portion, the another substrate having a reactive portion adapted to be attached to the deprotected portion, and a protected portion, the another substrate being attached to the deprotected portion via its reactive portion.

The method can further comprise repeating steps (b) and (c) a predetermined number of times. It can also comprise deprotecting the protected portion of another substrate. The method can further comprise cleaving the chemical bond between the substrate and the polymer or compound, and then recovering a desired product. It can also comprise recycling the polymer or substrate. The substrate and another substrate can be chosen from various possibilities presented in the present documents such as various organic compounds.

In accordance with another aspect of the present invention there is provided a process for preparing cross-linked poly (vinyl alcohol) beads, the process comprising reacting together poly(vinyl alcohol) and a base in the presence of water and dimethylsulfoxide so as to obtain a mixture;

reacting epichlorohydrin or another reagent with the mixture so as to obtain another mixture; and contacting the another mixture with an oil and an emulsifier.

For example, the base can be chosen from NaOH, potassium metal, sodium metal, an alkoxide such as but not limited to KOR, NaOR or LiOR where R is a linear or branched alkyl group of 1-10 carbons, a metal hydride, such as but not limited to KH, NaH LiH, an amide base such as but not limited to $NaNH_2$, $LiN(iPr)_2$, $KN(Si(Me)_3)_2$, supramolecular complexes of potassium methoxide and potassium hydroxide with 18-crown-6 (see Synthesis of Poly(2-methyl-3-hydroxyoctanoate) via Anionic Polymerization of -Methyl-pentyl-propiolactone (Arkin, A. H.; Hazer, B.; Adamus, G.; Kowalczuk, M.; Jedlinski, Z.; Lenz, R. W. Biomacromolecules; (Communication); 2001; 2(3); 623-627), organometallic reagents such as sec-butyllithium, tert-butyllithium and cumylpotassium. The poly(vinyl alcohol) and the base can be reacted together in a solution of water and dimethylsulfoxide. The solution can be a solution having a content of water comprised between 0 and 100%, and a content of dimethylsulfoxide comprised between 100% and 0%. For example, the solution can be a solution of about 1:1 water and dimethylsulfoxide.

For example, the poly(vinyl alcohol) and the base can be reacted together in a solution of water and dimethylsulfoxide and then filtered. For example, the poly(vinyl alcohol) and the base can be reacted together in a solution of water and dimethylsulfoxide under stirring. Epichlorohydrin can be added to the mixture under stirring (for example at a temperature of about 50° C. and above). The oil can be paraffin oil (high density or low density), toluene, o-xylene, hexane, or cyclohexane. The oil can be added to the mixture under stirring.

For example, the emulsifier can be Span 80 or Tween 80. The process can further comprise solidifying the obtained beads. The process can also comprise rinsing and extracting the beads in at least one organic solvent and/or water. The process can also comprise lyophilizing the beads. In accordance with another aspect of the present invention there are provided cross-linked poly(vinyl alcohol) beads obtained by a process as defined in the present document.

In accordance with another aspect of the present invention there is provided the use of poly(vinyl alcohol) beads for preparing poly(ethylene glycol)-grafted-poly(vinyl alcohol) beads or polyether-grafted poly(vinyl alcohol) beads.

The term "alkyl" as used herein refers to linear or branched radicals. Examples of such radicals include, but are not limited to, methyl, ethyl, n-propyl, isopropyl, n-butyl, isobutyl, sec-butyl, tert-butyl, pentyl, iso-amyl, hexyl and the like.

The term "aryl" has used herein refers to a cyclic or polycyclic aromatic ring. The aryl group can be, as example, phenyl or napthyl.

The term "heteroaryl" has used herein refers to an aromatic cyclic or fused polycyclic ring system having at least one heteroatom selected from the group consisting of N, O, and S. Examples of heteroaryl groups include, but are not limited to, furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, and quinazolinyl.

The term "heterocyclyl" includes non-aromatic rings or ring systems that contain at least one ring having at least one hetero atom (such as nitrogen, oxygen or sulfur). This term can, as example, include all of the fully saturated and partially unsaturated derivatives of the above mentioned heteroaryl groups. Examples of heterocyclic groups include, without limitation, pyrrolidinyl, tetrahydrofuranyl, morpholinyl, thiomorpholinyl, piperidinyl, piperazinyl, thiazolidinyl, isothiazolidinyl, and imidazolidinyl.

The polymer or compound can be adapted to act as a solid support for a substrate. The polymer can also be suitable for attaching a substrate thereto (for example an organic substrate, a catalyst or a derivative thereof, or a ligand or a derivative thereof. The polymer can be in the form of a resin.

The poly(vinyl alcohol) used can be a cross-linked poly (vinyl alcohol). For example, the cross-linked poly(vinyl alcohol) can have a degree of cross-linking comprised between 0% and 30%. It can also have a degree of cross-linking of about 1% to about 25%, about 2% to about 15%, or about 3% to about 10%. The polymer can also be inn the form of beads such as crosslinked poly(vinyl alcohol) beads having poly(ethylene glycol) or polyether chains grafted thereto. The poly(ethylene glycol) or polyether chains can be grafted to the beads in a pseudo spherical symmetrical manner.

The polymer can comprise a plurality of poly(ethylene glycol) or polyether chains grafted on poly(vinyl alcohol) beads, the chains independently comprising n ethylene glycol or ether unit(s) and n can have a value of 1 to about 500, about 2 to about 50, or about 2 to about 20.

For example, the polymer can be in the form of beads having a swelling capacity in water of at least 1 mL/g, at least 4.5 mL/g, at least 6 mL/g, at least 10 mL/g, at least 14 mL/g, or of about 4 mL/g to about 16 mL/g.

For example, the polymer can be in the form of beads having a swelling capacity in dimethylformamide of at least 1 mL/g, at least 4.5 mL/g, at least 6 mL/g, at least 10 mL/g, at least 14 mL/g, or of about 4 mL/g to about 18 mL/g.

For example, the polymer can be in the form of beads having a swelling capacity in tetrahydrofuran of at least 1 mL/g, at least 3 mL/g, at least 4 mL/g, at least 5 mL/g, at least 6 mL/g, or of about 3 mL/g to about 8 mL/g.

For example, the polymer can be in the form of beads having a swelling capacity in dichloromethane of at least 1 mL/g, at least 2 mL/g, at least 5 mL/g, at least 8 mL/g, at least 10 mL/g, or about 2 mL/g to about 13 mL/g.

For example, the polymer can be in the form of beads having a swelling capacity in acetonitrile of at least 1 mL/g, at least 2 mL/g, at least 4 mL/g, at least 6 mL/g, at least 8 mL/g, or of about 2 mL/g to about 9 mL/g.

For example, the polymer can be in the form of beads having a swelling capacity in toluene of at least 0.2 mL/g, at least 1.5 mL/g, at least 2.0 mL/g, at least 2.5 mL/g, at least 3 mL/g, or about 1.5 mL/g to about 4.0 mL/g.

For example, the polymer can be stable in 6 N HCl for a period of at least 2 hours, or at least 24 hours. The polymer can also be stable in 6 N NaOH for a period of at least 2 hours or at least 24 hours.

According to one embodiment, the poly(vinyl alcohol) can be linear. According to another embodiment, the polymer can be a brush-type polymer or a dendrimer-type polymer. According to another embodiment, the polymer can comprise a poly(vinyl alcohol) core having poly(ethylene glycol) or polyether chains grafted thereto.

According to another embodiment, the polymer can be a dendrimer-type polymer comprising a poly(vinyl alcohol) core having a plurality of poly(ethylene glycol) or polyether chains grafted thereto. The chains can independently comprise n ethylene glycol or ether unit(s), and n can have a value of about 1 to about 100.

According to another embodiment, the polymer can be a brush-type polymer comprising a poly(vinyl alcohol) core having a plurality of poly(ethylene glycol) or polyether chains grafted thereto. The chains can independently comprise n ethylene glycol or ether unit(s), and n can have a value of about 1 to about 100.

The polymers or compounds of the present invention can be used as a support in organic synthesis, as a polymer matrix for the synthesis of peptides, as a support in solid-phase chemistry, as a support for a catalyst, as a support for a scavenger, as a support for a therapeutic agent, as a support in a drug delivery system, or as a packing material in a column.

The substrate can be a peptide, a precursor, or a derivative thereof, an amino acid, a precursor or a derivative thereof, an oligonucleotide, a precursor or a derivative thereof, a carbohydrate, a precursor or a derivative thereof, a glycopeptide, a precursor or a derivative thereof, a catalyst, a precursor or a derivative thereof, a substrate for an enzyme, a ligand for a receptor, a ligand, a precursor or a derivative thereof, a derivative of a catalytic C1-C20 alkyl linear or branched, C3-C12 cycloalkyl, C1-C12 heterocyclyl, C2-C20 alkylheterocyclyl, C2-C20 alkenyl, C2-C20 alkynyl, C6-C12 aryl, C6-C20 aralkyl, C6-C20 alkylaryl, C1-C12 heteroaryl, C2-C20 alkylheteroaryl,

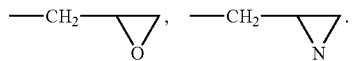

The PVA used for the resin preparation is not limited to the molecular weight and the degree of hydrolysis mentioned in the examples. The crosslinking reagent of PVA is not limited to the use of epichlorohydrin as mentioned in the examples.

The linkers grafted onto the PVA resins include polyethers of varying lengths and are not limited to poly(ethylene glycol) and the examples of the reactants include, without limitation, ethylene oxide, propylene oxide, tetrahydrofuran and other monomers.

The grafting of PEG and other polyethers onto the PVA beads is not limited to the methods as mentioned in the examples.

BRIEF DESCRIPTION OF DRAWINGS

In the following drawings, which represent by way of examples only particular embodiments of the present invention.

FIG. 2 shows a FTIR spectra of examples of PVA-PEG polymers according to particular embodiments of the present invention, wherein the polymers have different PEG lengths;

FIG. 3 shows a 1H NMR spectra of examples of PVA-PEG polymers according to particular embodiments of the present invention, wherein the polymers have different PEG lengths;

FIG. 5 shows scanning electron micrographs (top) and optical micrographs (bottom), of examples of PVA beads according to a particular embodiment of the present invention and of examples of PVA-PEG polymers beads according to particular embodiments of the present invention, wherein the polymers have different PEG lengths;

DETAILED DESCRIPTION OF PREFERRED EMBODIMENTS OF THE INVENTION

Figure 1:
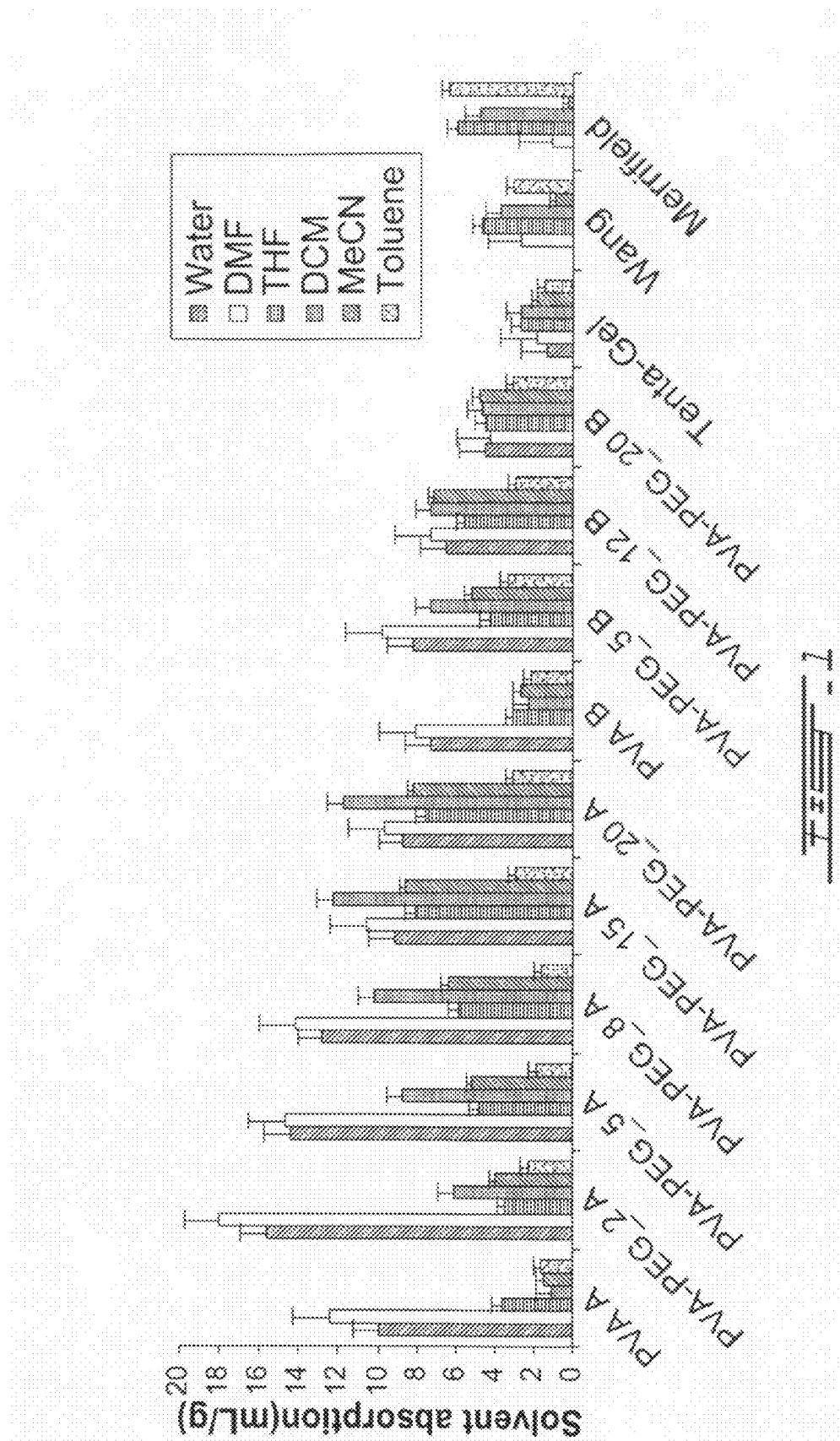
FIG. 1 shows a comparison between Tenta-Gel, Wang and Merrifield resins and some examples of resins according to particular embodiments of the present invention.
Figure 4:
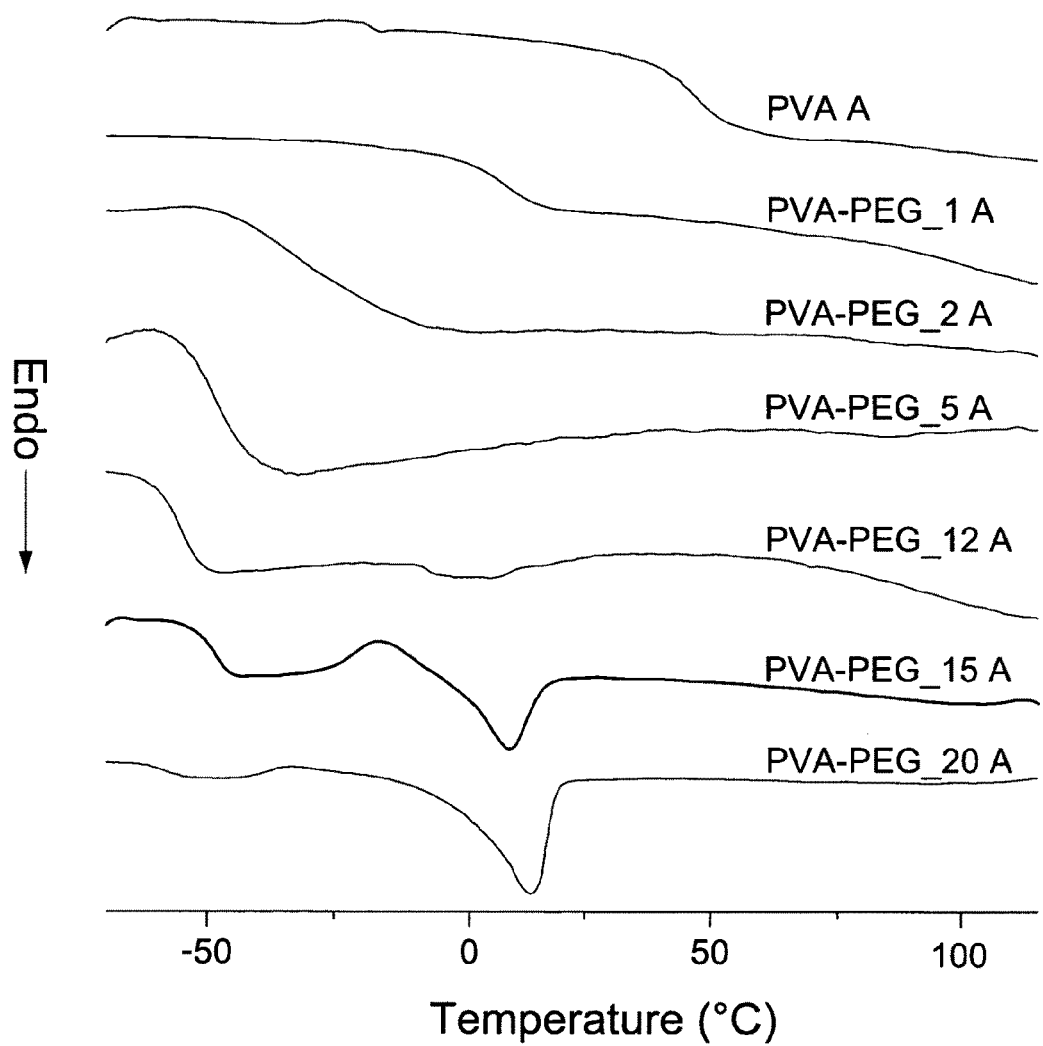
FIG. 4 shows DSC thermograms, at the first heating, of examples of PVA-PEG polymers according to particular embodiments of the present invention, wherein the polymers have different PEG lengths.
Figure 6:
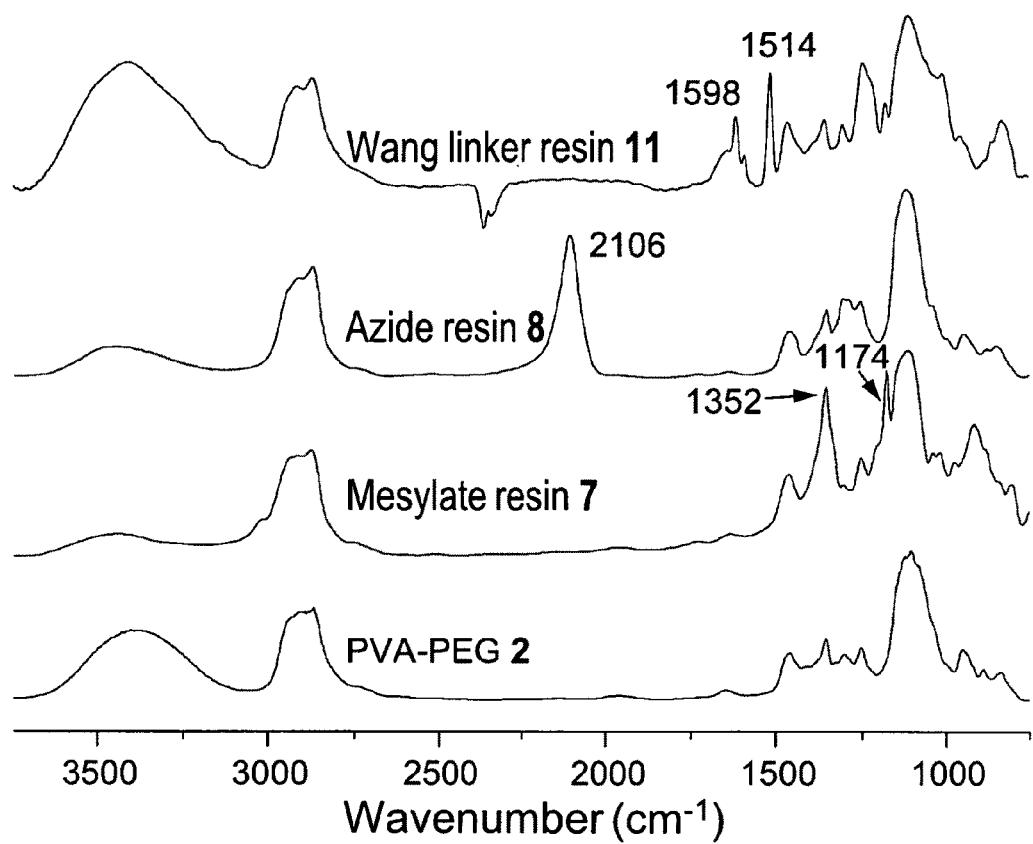
FIG. 6 shows a FTIR spectra of an example of PVA-PEG resin according to particular embodiments of the present invention and of intermediates during its preparation.

The following examples represent in a non-limitative manner, preferred embodiments of the present invention.

Experimental Section

Materials and Instruments

Linear PVA (98% hydrolyzed, $M_w$=13,000-23,000), epichlorohydrin (EP, 99%), sorbitan monoleate (Span 80), ethylene oxide, n-butyl lithium solution in hexane (1.6 mol/L), Z-Gln-OH, 1-hydroxybenzotriazole hydrate (HOBt), 1-3-diisopropylcarbodiimide (DIC), 4-dimethylaminopyridine (DMAP), ammonia (2.0 M solution in methanol), piperidine, triphenylphosphine, imidazole, benzyl alcohol, cyclohexanol, 1-octanol, 2-octanol, 1-dodecanol and pentan-1,5-diol, all were purchased from Sigma-Aldrich. Paraffin oil was purchased from American Chemicals; 1,8-diazabicyclo[5.4.0]undec-7-ene (DBU) from Acros Inc.; Fmoc-Gln-OH, Fmoc-Gly-OH, Fmoc-Pro-OH, Fmoc-Asn-OH, Fmoc-Leu-OH and Fmoc-Phe-OH from Novabiochem. The above-mentioned chemicals were used without further purification. Acetic anhydride (99% from Aldrich) was dried and distilled from sodium and stored tightly sealed. Pyridine was dried and distilled from sodium hydroxide. Dimethyl sulfoxide (DMSO) and benzene were dried and distilled from calcium hydride. Tetrahydrofuran (THF) was dried and distilled from sodium in the presence of benzophenone after the solution turned dark blue. Potassium naphthalene was prepared in dry THF from naphthalene and potassium at a concentration of 0.45 M (titrated with a standard hydrochloric acid solution using phenolphthalein as an indicator). Sodium hypochlorite (10-13% available chlorine, purchased from Aldrich) was diluted in a 0.4 M buffer with $KHCO_3$ at pH=9.1 (0.5 g $KHCO_3$ in 10 mL 0.4 M bleach solution). N-(Boc)aminoethanol and N-benzyl, N-(Boc)aminoethanol were prepared from aminoethanol (Fluka) and N-benzyl aminoethanol (Aldrich), respectively, using $(Boc)_2O$ (Aldrich) in THF (Becht, J. M. I.; Meyer, O.; Helmchen, G. *Synthesis* 2003, 18, 2805-2810). (2S)- and (2R)-2-[N-(Boc)amino]-3-methyl-butane-1,3-diol were prepared as reported. (Dettwiler, J. E.; Lubell, W. D. *Can. J. Chem.* 2004, 82(2), 318-324) N—(PhF) Homoserinetert-butyl ester was synthesized following the reported procedure. (Gosselin, F.; Lubell, W. D. *J. Org. Chem.* 1998, 63, 7463-7471) Treatment of pyrrolidin-3-ol with benzyl chloroformate (Cbz-Cl) and $Na_2CO_3$ in a biphasic mixture of ether-$H_2O$ gave the known N-Cbz pyrrolidin-3-ol in 98% yield. (Tomori, H.; Shibutani, K.; Ogura, K. *Bull. Chem. Soc. Jpn.* 1996, 69, 207) Dihydrocholesterol (Sigma) was used as received. Lithocholic acid methylester was prepared by reacting lithocholic acid (Sigma) with methanol (Rensen, P. C. N.; van Leeuwen, S. H.; Sliedregt, L. A. J. M.; Van Berkel, T. J. C.; Biessen, E. A. L. *J. Med. Chem.*, 2004, 47(23), 5798-5808).

Magic angle spinning (MAS) $^1H$ NMR experiments were performed on a Bruker Avance 600 NMR spectrometer (600 MHz) equipped with a 4-mm HRMAS $^1H$ probe with spin rate of ~6K Hz. Around 5 mg of beads was transferred into a Nano NMR tube and 40 μL of DMF-$d_7$ was then added. The spectra were recorded at room temperature and with a presaturation at 3.65 ppm. $^1H$ and $^{13}C$ NMR spectra of the PVA-PEG resins and small molecular weight products were recorded on a Bruker Avance 300 (or 400) spectrometer operating at 300 MHz (or 400 MHz) for protons and 75 MHz (or 100 MHz) for $^{13}C$. FTIR spectra of the PVA and PVA-PEG beads were recorded on a Bomen MB-100 FTIR spectrometer at room temperature using potassium bromide pellets made with ground polymer beads. The thermal properties of the polymer beads were analyzed on a differential scanning calorimeter (TA instrument DSC2910). The morphology of the polymer beads was examined by electron microscopy by the use of a field emission scanning electron microscope (FE-SEM, from S-4700) after coating the sample with gold. Liquid chromatography/mass spectrometry (LC/MS) traces were obtained on a coupled GILSON LC-ThermoFinnigan MSQ instrument equipped with a Prevall Allteck C18 (5 micron 250×46 mm) column using a gradient consisting of a mixture of A (0.01% TFA in $H_2O$) and B (0.01% TFA in $CH_3CN$) over 20 min with 80% A/20% B, then over 5 min with 20% A/80% B, then over 5 min with 10% A/90% B and finally with 80% A/20% B; MS conditions: scan 100-500, cone voltage 30 kV, temperature 400° C., mode (polarity) positive. UV-visible data were obtained on a UV-visible spectrometer (Cary 300 Bio, Varian). The bead size was analyzed on a particle sizer Horiba LA 950 using water as a media to suspend the beads.

Preparation of PVA Beads

Crosslinked PVA beads were first prepared as previously reported (method A) ((a) Wan, Y.; Huang, W-Q.; Wang, Z.; Zhu, X. X. *Polym.* 2004, 45, 71-7; (b) Wang, Z.; Luo, J. T.; Zhu, X. X.; Jin S. J.; Tomaszewski, M. J. *J. Comb. Chem.* 2004, 6, 961-966) with epichlorohydrin as crosslinker (These two references are hereby incorporated by reference in their entirety. Subsequently, PVA beads having a higher degree of crosslinking were prepared by a novel method as described here. In the new method sodium hydroxide (4 g) was dissolved into a PVA (6 g) solution of DMSO and water and filtered into a 500 mL round bottom flask equipped with mechanical stirrer. Epichlorohydrin (7 mL) was added to the PVA solution with gentle mechanical stirring at 50° C. and above. Paraffin oil (preheated, 200 mL) was added to the viscous solution with increased mechanical stirring, then Span 80 (0.4 mL) was added to the reaction mixture. Beads were formed in the reverse suspension and solidified at 55° C. or above for 24 h. The PVA beads were filtered and rinsed with petroleum ether, THF and water, and transferred into a Soxhlet extractor. The beads were extracted successively with THF, acetone, and water, each for 24 h. The beads were transferred to a lyophilizer and freeze-dried for 48 h to provide PVA beads 1 (5.6 g, 93% yield) with the swollen mean bead size of 87 μm in water. The hydroxyl group loading of the beads (PVA 1) was analyzed to be 15 mmol/g by back titration of the excess of acetic acid after blocking OH groups PVA 1 with acetic anhydride in pyridine. The FTIR spectrum of the beads PVA 1 showed strong OH stretching band around 3400 $cm^{-1}$.

Attachment of PEG onto PVA a) Attachment of PEG onto PVA Activated as Sulfonate

To a suspension of PVA resin 1 (1 g, 17 mmol/g) (see Scheme 1) in DCM in the presence of $Et_3N$ (9.4 mL, 85 mmol), p-toluenesulfonyl chloride (16.2 g, 85 mmol) was added dropwise at 0° C. The ice bath was removed and the reaction mixture was stirred overnight at room temperature. The resin was filtered, washed with DCM, THF and diethyl ether (three times each) and dried under vacuum, yielding a light yellow p-toluenesulfonate resin. FTIR: 1600, 1352, 1174 $cm^{-1}$. Different chain lengths of linear PEG (5 eq.) were respectively treated with NaH (6 eq.) in THF cooled with an ice bath. The p-toluenesulfonate resin (1 eq.) was added into the PEG slurry, which was then warmed to room temperature and stirred for 48 h. The resin (PVA-PEG 2) was filtered and rinsed with ethanol, water, 0.1 N aq. HCl, water, ethanol, and dichloromethane and dried under vacuum. The appearance of an ether absorption in the FTIR spectrum at 1100 $cm^{-1}$ demonstrated the attachment of PEG chains onto the resin.

b) Attachment of PEG onto PVA Via Ether Bond Formation

Crosslinked PVA beads 1 (1 g) were treated with NaOH (1.36 g) in DMF (20) at 70° C. for 2 h (see Scheme 1). 2-(2-chloroethoxy)ethanol (6.85 g) was added to the reaction mixture, which was stirred at 70° C. for 24 h. The resin was filtered, washed with DMF, water, 0.1 N HCl, water, ethanol, DCM and diethyl ether and dried in vacuum to give 1.05 g of diethyleneglycol grafted PVA resin 3.

c) Attachment of PEG onto PVA Via a Diisocyanate Linker

3-Isocyanatementhyl-3,5,5-trimethyl-cyantate (IPDI) was used as an example to present a general procedure for an anchoring strategy (see Scheme 1). PVA resin 1 (1 g, 15 mmol/g) was swollen in DMF (30 mL) for 30 min. IPDI (2 eq., 15.4 ml) and DBTDL (dibutyltin dilaurate, 1 mol %, 0.2 ml) were added into the suspension mixture, which was stirred at 90° C. for 24 h. Small portions of resin were periodically withdrawn from the reaction system, rinsed and dried for FTIR analysis (2268, 1711 and 1529 $cm^{-1}$). Poly (ethyleneglycol) (10 eq.) with another portion of catalyst (DBTDL, 1 mol %, 0.2 ml) was added directly without isolation of the resin. The reaction was agitated at 90° C. for another 24 h. The resin 4 was successively rinsed with DMF, DCM, THF and diethyl ether and dried under vacuum. The FTIR spectrum showed strong urethane bands at 1711 and 1529 $cm^{-1}$.

d) High Pressure-High Temperature Process Polymerization

A suspension of PVA resin 1 (5 g) and KOH (1.1 eq.) in dioxane (150 ml) was placed into a pressure reactor and purged with nitrogen gas for 30 min at 100° C. (see Scheme 1). Ethylene oxide (50 ml) was condensed into the reactor, which was cooled with a dry ice/acetone bath. The reaction mixture was sealed, heated and maintained at 110° C. with stirring for 9 h. After the system was cooled to room temperature, the resin was filtered and washed with dioxane/water (1:1, ×3), 0.1 N HCl, water, ethanol and dichloromethane, and dried under vacuum. The grafting levels of resin 5 were determined by weight increase.

e) Anionic Polymerization of Ethylene Oxide onto the PVA Beads

The previously prepared PVA beads were employed in PEG grafting (see Scheme 2). PVA beads 1 (0.4 g) were placed into a 100 mL flask, equipped with a Dean-Stark trap, and 25 mL of dry DMSO was charged into the flask to swell the PVA resin. A calibrated amount of potassium naphthalene in THF (0.45 M, 6 mL, 0.45 eq.) was introduced into the flask dropwise via a double-tip needle. The mixture was stirred for 2 h to allow the green color from the naphthalene potassium to completely disappear. Ethylene oxide of a known volume was allowed to distill into the resin suspension. The polymerization mixture was heated and magnetically stirred at 40° C. for 48 h. The resin was filtered and rinsed with water and THF and subsequently extracted successively with THF and water using a Soxhlet extractor for 24 h per solvent. The beads were finally freeze-dried for 48 h to give copolymer resin 6. The resin was characterized with FTIR, NMR, DSC and SEC (see FIGS. 2 to 6) and stored below 5° C. under nitrogen.

Loading Determination a) Calculation of Theoretical Loading and the Number of Ethylene Oxide Units In principle, no net hydroxyl group loss occurs during the anionic polymerization. The theoretical loading of PVA-PEG resin may thus be calculated by multiplying the loading of the PVA beads ($L_0$) by a ratio of the bead weights before ($W_0$) and after ($W_1$) the anionic polymerization:

$$L_t = \frac{L_0 \times W_0}{W_1} \quad (1)$$

The theoretical hydroxyl group loading $L_t$ for the PVA-PEG was determined using titrated loading $L_0$ of hydroxyl group on the crosslinked PVA resin (17 and 15 mmol/g for the beads prepared by methods A and B, respectively). The number of ethylene oxide units attached on the PVA beads (n) can be calculated according to the weight increase and the amount of reactive species in the anionic polymerization:

$$n = \frac{W_1 W_0}{44(C_i!V_i)} \quad (2)$$

where $C_i$ and $V_i$ are the concentration and the volume of the potassium naphthalene (initiator) solution in THF, respectively, and 44 is the molecular weight of the ethylene oxide repeating unit.

b) Acetic Anhydride Back Titration

The loading of hydroxyl groups on the polymer beads was determined by titrating the excess acetic acid formed upon the acetylation of the hydroxyl groups on the resin after the addition of acetic anhydride (Siggia S. Instrumental methods of organic functional group analysis. New York: Wiley; 1972). About 100 mg of beads (PVA or PVA-PEG) were place into a 20 mL flask, heated with 0.5 mL of acetic anhydride and 5.0 mL of pyridine, stirred for 12 h at 60° C. then treated with 1 mL of water to hydrolyze the excess acetic anhydride into acetic acid. The mixture was completely transferred into an Erlenmeyer flask for the titration in the presence of resin. An excess aqueous solution of 0.4481 N NaOH (25 mL) was added to react with the acetic acid, then the excess of NaOH was titrated with a 0.1918 N HCl aqueous solution using phenolphthalein as an indicator. A blank titration was performed in the same way to avoid systematic errors.

c) Fmoc-Fluorescence Measurement (Atherton, E.; Sheppard, R. C. *Solid Phase Peptide Synthesis: a Pratical Approach*, IRL Press, Oxford, 1989)

Swollen PVA-PEG resin 6 (20 mg) was esterified with N-(Fmoc)glycine (~500 mol % relative to the titration loading of the resin) by stirring overnight at room temperature in 0.5 mL of DMF in the presence of DIC (~500 mol % relative to the titration loading of the resin) and 2.5 mg of DMAP (~10 mol % relative to the titration loading of the resin). The resin was successively rinsed with 15 mL of DMF, 25 mL of DCM and 10 mL of diethyl ether, and dried to a constant weight. A 5 mg aliquot of the coupled resin was treated with 1 mL of piperidine solution in DMF (20:80) for one hour, and diluted to 50 mL with ethanol. The loading of the Fmoc-glycine was determined by UV measurement at 301 nm of the liberated dibenzofulvene by piperidine/DMF. The loading of OH group ($L_{OH}$) was calculated from the Fmoc loading as following:

$$L_{OH} = \frac{L_{Fmoc}}{1!L_{Fmoc}(297!18)/1000} \quad (3)$$

where $L_{OH}$ is the loading of OH groups, that were acylated with Fmoc-glycine, $L_{Fmoc}$ is the loading of PVA-PEG supported Fmoc-glycine determined by UV spectrophotometry of liberated dibenzofulvene; 297 is the molecular weight of Fmoc-glycine; 18 is the molecular weight of the released $H_2O$ during the acylation.

Swelling

A glass capillary was used to transfer solvent to the beads (roughly 3 mg), which were weighed on a poly(tetrafluoroethylene) slice to avoid excess solvent adhering onto the matrix. The beads absorbed solvent from the capillary until equilibrium was reached between the solvent in the capillary and in the swollen bead. This procedure was repeated several times over a period of 10 minutes to allow the full swelling of the beads. The beads saturated with solvent were then weighed using a microbalance, and the weight gain was converted into the volume of solvent retained per gram of polymer.

Modification of PVA-PEG Resins

Preparation of PVA-PEG Aldehyde Resin 7

A stoppered plastic tube-shaped reactor fitted with a Teflon filter was charged with TEMPO (0.45 mmol, 70 mg) in 2 mL of DCM and 1.25 mL of bleach (0.4 M), buffered with $KHCO_3$ at pH 9.1, treated with aqueous KBr (0.5 M, 0.08 mL), and shaken at room temperature for 30 min. The phases were separated and the deep red DCM phase was transferred into another plastic tube-shaped reactor containing PVA-PEG_12 resin (50 mg, 3.0 mmol/g) and the mixture was shaken for 2 h (see Scheme 3). The resin was filtered and washed with DCM, THF and diethyl ether, then dried under vacuum. A strong absorption was observed at 1610 cm$^{-1}$ in the FTIR spectrum of the oxidized PVA-PEG beads. The aldehyde loading was ascertained to be 0.66 mmol/g by a rapid fluorescence determination (Yan, B.; Li, W. B. *J. Org. Chem.* 1997, 62, 9354-9357) of the excess dansylhydrazine remaining after the reaction of the aldehyde resin with approximate 2-fold excess dansylhydrazine.

Preparation of PVA-PEG Carboxylic Acid Resin 8

PVA-PEG__5 resin 6 (0.1 g, 4.0 mmol/g) was agitated with 3 mL of bleach (0.4 M, 3 eq.) and 0.12 mL of KBr (0.5 M, 10 mol %) at pH 9.1 (buffered with $NaH_2CO_3$) (see Scheme 3). A TEMPO (6.3 mg, 0.04 mmol) solution in acetonitrile was added to the mixture, which was agitated overnight at room temperature. The resin was filtered and washed with water, 0.1 M HCl, water, THF and diethyl ether, and dried under vacuum: FTIR: 1747 $cm^{-1}$. The carboxylic acid loading of resin 8 was measured to be 2.3 mmol/g by nitrogen elemental analysis after the conversion of carboxylic acid group into the corresponding carboxylic azide (Okaniwa, M.; Takeuchi, K.; Asai, M.; Ueda, M. *Macromolecules*, 2002, 35, 6224-6231) by a treatment with diphenyl phosphorylazide in THF overnight. FTIR spectrum of acyl azide resin 9 showed a strong band at 2155 $cm^{-1}$ of azide adsorption. The acyl azide resin was converted into isocyanate resin 10 via a Curtius rearrangement by heating to 140° C. for 30 min. FTIR: 2255 $cm^{-1}$ of isocyanate band.

Attachment of Wang Linker to PVA-PEG Resin

Methanesulfonate PVA-PEG Resin 11

To a suspension of PVA-PEG__5 B resin 6 (0.5 g, 6.2 mmol/g for PVA-PEG__5 and 1.55 g, 2.0 mmol/g for PVA-PEG__20, respectively) and $Et_3N$ (3.3 mL, ~1000 mmol %) in DCM, methanesulfonyl chloride (3.48 g, ~1000 mol %) was added dropwise at 0° C. (see Scheme 4). The ice bath was removed and the reaction mixture was stirred overnight at room temperature. The resin was filtered, washed with DCM, THF and diethyl ether three times each, respectively, and dried under vacuum, to yield a light yellow methanesulfonate resin 11 (669 mg). FTIR: 1352, 1174 $cm^{-1}$.

Azido PVA-PEG Resin 12

A suspension of methanesulfonate resin 11 (~3 mmol) and $NaN_3$ (2.0 g, ~1000 mol %) in DMSO (40 mL) was heated and stirred overnight at 70° C., filtered and washed with DMF, DCM, THF and diethyl ether, for 3 times each, respectively, and dried under vacuum to yield yellow azido resin 12 (see Scheme 4). FTIR spectrum showed a strong adsorption at 2106 $cm^{-1}$ of the $N_3$. Azide loadings of resin 12 were determined to be 2.42 and 1.25 mmol/g by nitrogen elemental analysis for the PEG units of 5 and 20, respectively.

Preparation of 4-prop-2-ynyloxy-benzyl Alcohol 14

To a solution of 4-hydroxyl-benzyl alcohol 13 (2.5 g, 20 mmol) in acetonitrile (50 mL), $K_2CO_3$ (3.96 g, 200 mol %) was added at room temperature (see Scheme 4). After stirring for 1 h, the mixture was treated dropwise with an 80 wt % solution of propargyl bromide in toluene (3.27 g, 110 mol %) and the reaction mixture was heated to 50° C. for 48 h, cooled, filtered and concentrated under vacuum. The residue was purified by flash chromatography using an eluent of 100% to 30% hexane in AcOEt. Evaporation of the collected fractions gave propargyl ether 14 as a yellow liquid (3.12 g, 95.5%): $^1H$ NMR ($CDCl_3$) δ (ppm): 7.28 (d, 2H, Ph-H), 6.96 (d, 2H, Ph-H), 4.69 (d, 2H, $PhCH_2$), 4.57 (s, 2H, $CCH_2O$), 2.54 (t, 1H, OH), 2.39 (s, 1H, CH); $^{13}C$ NMR ($CD_3OD$) δ (ppm): 157.4, 134.53, 128.97, 115.34, 78.97, 76.04, 65.10, 56.24. Anal. Calcd for $C_{10}H_{10}O_2$: C, 74.07; H, 6.17. Found: C, 73.64; H, 6.03.

Preparation of Wang Linker Resin 15

Azido-PVA-PEG resin 12 (200 mg, 2.42 mmol/g for PVA-PEG__5 and 400 mg, 1.25 mmol/g for PVA-PEG__20, respectively) was agitated with 4-prop-2-ynyloxy-benzyl alcohol 7 (405 mg, ~500 mol %), CuI (9.6 mg, 10 mol %), DIPEA (0.5 mL, 525 mol %) and $Ph_3P$ (14 mg, 10 mol %) in DMF (3 mL) at room temperature for 24 h (see Scheme 4). The suspension was filtered and the resin was rinsed successively with pyridine (3×20 mL), DCM (3×20 mL), THF (3×20 mL) and diethyl ether (3×20 mL) and dried under vacuum to yield a brown Wang linker resin 15. The Wang linker loadings were determined by nitrogen elemental analysis to be 1.63 and 1.08 mmol/g, respectively for resins 15 with PEG units of 5 and 20. The loading of hydroxyl groups were also analyzed by Fmoc-fluorescence measurement after an acylation of resin with Fmoc-glycine to be 1.74 and 1.08 mmol/g, respectively for resin 15 with PEG units of 5 and 20. FTIR spectrum of Wang linker derivatized resin 15: 1614, 1598, 1514, 1465 $cm^{-1}$ and on-bead HR/MAS $^1H$ NMR in DMF-$d_7$ δ (ppm): 8.43 (s, 1H), 7.50 (d, 2H, J=6.5 Hz), 7.22 (d, 2H, J=6.0 Hz), 5.38 (s, 2H), 5.17 (bs, 1H), 4.81 (s, 2H), 4.74 (s, 2H), 4.10 (s, 2H), 3.68-3.80 (m, PEG-H), 1.28-1.92 (m, PVA-H)

Peptide Synthesis

General Procedure for Peptide Synthesis

Swollen PVA-PEG resin 6 (105 mg for PVA-PEG__20 resin and 35 mg for PVA-PEG__5 resin) in 1.5 mL of DMF was treated with N-(Fmoc)glycine (309 mg, ~500 mol %), DIC (168 μL, ~500 mol %) and DMAP (2.5 mg, ~10 mol %), stirred overnight at room temperature, filtered and successively rinsed with 15 mL of DMF, 25 mL of DCM, and 10 mL of diethyl ether. Loading was measured as described above in the Fmoc-fluorescence measurement. The swollen acylated resin was stirred for 2 h with 3 mL of acetic anhydride/pyridine:solution (40:60) to acetylate the residual alcohol groups. The resin was successively washed with 15 mL of DMF and 25 mL of DCM. The loading of the Fmoc-glycine was determined by UV measurement at 301 nm of the liberated dibenzofulvene by piperidine/DMF (Atherton, E.; Sheppard, R. C. *Solid phase peptide synthesis: a pratical approach*, IRL Press, Oxford, 1989). Fmoc cleavage was carried out with 3 mL of piperidine/DMF solution (20:80) for 1 h. The deprotection was monitored by a positive Kaiser test (Kaiser, E., Colescott, R. L.; Bossinger, C. D.; Cook, P. I. *Anal. Biochem*, 1970, 34, 595).

During the peptide elongation, the deprotected resin was treated with N-(Fmoc)-amino acid (~250 mol %), HOBt (250 mol %) and DIC (250 mol %) in DMF (1.5 mL). The mixture was shaken overnight at room temperature and the resin was filtered and washed successively with 15 mL of DMF, 50 mL of DCM, and 10 mL of diethyl ether. The coupling was monitored by the Kaiser test. Fmoc cleavage was performed as described above.

Synthesis of Z-Gln-Gly-OMe 16

Z-Gln-Gly was synthesized on PVA-PEG__5 (1.39 mmol/g) and PVA-PEG__20 resins (0.98 mmol/g) following the methods described above. In the coupling step, Z-Gln was employed as the Fmoc amino acid. The cleavage of peptides from the PVA-PEG resins was performed in a 2.0 M solution of ammonia in methanol for one hour at 0° C. After resin filtration and methanol wash, the filtrate and washings were combined and evaporated. Z-Gln-Gly-OMe 16 (see Scheme 5) was isolated by methanol/ether precipitation in 75% yield (14.6 mg) and 98% purity (LC-MS analysis) for PVA-PEG__5 resin; in 84% yield (28.8 mg) and 96% purity (LC-MS analysis) for PVA-PEG__20 resin, respectively. A white solid 16 was obtained. $^1H$ NMR (300 MHz, $CD_3OD$) δ (ppm): 7.33 (m, 5H, CH aromatic benzyl), 5.08 (s, 2H, $CH_2$ benzyl), 4.18 (m, 1H, CH Gln), 3.93 (m, 2H, $CH_2$ Gly), 3.70 (s, 3H, methyl ester), 2.34 (m, 2H, $CH_2$γGln), 2.08 (m, 1H, $CH_2$, Gln), 1.93 (m, 1H, $CH_2$βGln). $^{13}C$ NMR (75 MHz, $CD_3OD$) δ (ppm): 177.9, 174.9, 171.7, 158.4, 138.1, 129.5, 129.1, 128.9, 67.8, 55.9, 52.6, 41.8, 32.4, 29.1. LCMS: $t_R$ 12.95 min, m/z 352.0 $[M+H]^+$.

Synthesis of Pro-Asn-Pro-Gln-Leu-Pro-Phe-OMe 17

Pro-Asn-Pro-Gln-Leu-Pro-Phe sequence was synthesized on PVA-PEG_5 (1.2 mmol/g) and PVA-PEG_20 (0.64 mmol/g) resins following the above methods. The cleavage of peptides from the PVA-PEG resins using a 2.0 M solution in methanol of ammonia was performed at 0° C. for 1 h. After resin filtration and methanol wash, the filtrate and washings were combined and evaporated. Heptapeptides methyl ester 17 (see Scheme 5) were obtained in 53% yield (10.1 mg from 59 mg of resin) and in 75% purity for PVA-PEG_5 resin; in 18% isolated yield (12.9 mg from 46 mg of resin) and 50% purity (LC-MS analysis) for PVA-PEG_20 resin, respectively. LCMS: $t_R$ 12.96 min, m/z 826.4 $[M+H]^+$.

Synthesis of Z-Gln-Gly-$NH_2$ 18

Dipeptide Z-Gln-Gly residue was also cleaved from the PVA-PEG_5 resin using a saturated methanol solution of ammonia at room temperature for overnight. After resin filtration and methanol wash, the filtrate and washings were combined and evaporated. The amido-peptide (Z-Gln-Gly-$NH_2$) 18 (see Scheme 5) was isolated by acetone trituration in 98% yield (14 mg from 35 mg of resin with a loading of 1.1 mmol/g) and in 92% purity (LC-MS analysis). A white solid was obtained. $^1$H NMR (300 MHz, DMSO) δ (ppm): 8.12 (t, 1H, J=5.4 Hz, NH Gly), 7.56 (d, 1H, J=7.4 Hz, NH Gln), 7.36 (m, 7H, CH aromatic benzyl and $NH_2$), 7.10 (s, 1H, $NH_2$ Gln), 6.78 (s, 1H, $NH_2$ Gln), 5.02 (s, 2H, $CH_2$ benzyl), 3.96 (m, 1H, CH Gln), 3.63 (d, 2H, J=5.5 Hz, $CH_2$ Gly), 2.10 (m, 2H, $CH_2$γGln), 1.87 (m, 1H, $CH_2$βGln), 1.74 (m, 1H, $CH_2$βGln). $^{13}$C NMR (75 MHz, $CD_3$OD) δ (ppm): 162.1, 161.3, 160.4, 146.8, 129.1, 121.3, 120.8, 120.7, 63.5, 53.3, 41.7, 32.1, 28.4. LCMS: $t_R$ 3.19 min, m/z 337.0 $[M+H]^+$. MS m/z: 337.15 $[M+H]^+$.

Synthesis of Pro-Asn-Pro-Gln-Leu-Pro-Phe-$NH_2$ 19

Pro-Asn-Pro-Gln-Leu-Pro-Phe residue was also cleaved from PVA-PEG_5 resin using a saturated methanol solution of ammonia at room temperature for overnight. After resin filtration and methanol wash, the filtrate and washings were combined and evaporated. The amido-heptapeptide (Pro-Asn-Pro-Gln-Leu-Pro-Phe-$NH_2$) 19 (see Scheme 5) was isolated by precipitation from acetone/diethyl ether at −20° C. in 99% yield (20 mg from 35 mg of resin with a loading of 0.65 mmol/g) and 70% purity by LC-MS analysis. LCMS: $t_R$ 3.95 min, m/z 811.3 $[M+H]^+$. MS m/z: 811.45 $[M+H]^+$.

Synthesis of Z-Gln-Gly 20

Z-Gln-Gly was synthesized on Wang linker derivatized PVA-PEG_5 resin (loading 0.64 mmol/g) and PVA-PEG_20 resin (loading 0.43 mmol/g) following the methods described above. The cleavage of dipeptide from the Wang-linker resins 15 was performed in a solution of trifluoroacetic acid (TFA)/dichloromethane (DCM) 50:50 (v/v) for one hour at room temperature. After resin filtration and dichloromethane wash, the filtrate and washings were combined and evaporated. The peptide was analyzed without further purification. Z-Gln-Gly 20 (see Scheme 5) was obtained in 100% yield (3.9 mg from 25 mg of resin) and 90% purity (LC-MS analysis) for PVA-PEG_5 Wang linker resin, and in 65% (3.1 mg from 25 mg of resin) and 91% purity (LC-MS analysis) for PVA-PEG_20 Wang linker resin, respectively. A white solid was obtained. $^1$H NMR (300 MHz, $CD_3$OD) δ (ppm): 7.33 (m, 5H, CH aromatic benzyl), 5.08 (s, 2H, $CH_2$ benzyl), 4.18 (m, 1H, CH Gln), 3.93 (m, 2H, $CH_2$ Gly), 2.34 (m, 2H, $CH_2$γGln), 2.08 (m, 1H, $CH_2$βGln), 1.93 (m, 1H, $CH_2$βGln). $^{13}$C NMR (75 MHz, $CD_3$OD) δ (ppm): 178.1, 177.6, 175.1, 160.3, 141.2, 129.7, 128.2, 128.1, 54.8, 44.9, 32.8, 30.0. LCMS: $t_R$ 3.60 min, m/z 338.0 $[M+H]^+$.

Preparation of Peptide Alcohols

Fmoc-L-Leu and Fmoc-D-Leu were coupled onto PVA-PEG_5, respectively, following the protocol described above (loading: 1.5 mmol Fmoc/g). After removal of the Fmoc group with 20% piperidine/DMF (monitored by Kaiser test), Boc-L-Phe was coupled onto the Leu resins following the peptide elongation procedure described above. Dipeptide resins 21 (see Scheme 6) were treated with ethanolamine (5 eq.) in acetonitrile/DCM (1:1 v/v) at 50° C., stirred overnight, filtered and washed with THF. The filtrate and washings were combined and evaporated under vacuum. The residue was dissolved in ethyl acetate and washed with water, 0.1 N HCl and water, and dried with anhydrous $Na_2SO_4$. Peptide alcohols were isolated as white powders by precipitation from ethyl acetate/hexane, respectively, in 93 and 96% yield and 90 and 95% purity as assessed by LC-UV at 214 nm, m.p.: 163-164 and 181° C., respectively, for (L,L)-22 and (L,D)-22. The diastereomeric ratio of the peptide alcohols was measured by $^1$H NMR spectroscopy by integration of methyl peaks on leucine (0.82 and 0.93 ppm for L and D-isomers, respectively) of >99.5% diastereomeric purity. N-Boc-L-phenylalaninyl-L-leucinylglycinol [(L,L)-22]: $^1$H NMR (400 MHz, $CDCl_3$) δ: 7.37-7.23 (m, 5H, CH aromatic benzyl), 6.78 (s, 1H, NH), 6.28 (d, 1H, NH), 4.97 (d, 1H, NH), 4.46 (m, 1H, CH Phe), 4.33 (m, 1H, CH Leu), 3.69 (m, 2H, $CH_2$O), 3.46 (m, 1H, βCH Phe), 3.33 (m, 1H, βCH Phe), 3.06 (m, 2H, $NCH_2$), 2.03 (b, 1H, OH), 1.69 (m, 1H, βCH Leu), 1.44 (s, 9H, $CH_3$ Boc), 1.34 (m, 1H, βCH Leu), 1.15 (s, 1H, CHγLeu), 0.82 (t, 6H, $CH_3$ Leu); $^{13}$C NMR (100 MHz, $CDCl_3$) δ: 173.1, 172.2, 156.3, 136.7, 129.7, 129.0, 127.6, 81.2, 62.1, 56.5, 52.3, 42.9, 42.1, 38.2, 28.6, 25.1, 23.4, 22.2; LC/MS: $t_R$ 7.64 min (0-40% B %, A=$H_2O$, B=ACN, flow=0.5 ml/min), m/z 444.2 $[M+Na]^+$. N-Boc-L-phenylalaninyl-D-leucinylglycinol [(L,D)-22]: $^1$H NMR (400 MHz, $CDCl_3$) δ: 7.37-7.20 (m, 5H, CH aromatic benzyl), 7.10 (s, 1H, NH), 6.14 (d, 1H, NH), 5.12 (d, 1H, NH), 4.37 (m, 1H, CH Phe), 4.20 (m, 1H, CH Leu), 3.70 (m, 2H, $CH_2$O), 3.37 (m, 2H, βCH Phe), 3.10 (m, 2H, $NCH_2$), 2.03 (b, 1H, OH), 1.69 (m, 1H, CHγLeu), 1.51 (m, 2H, $CH_2$βLeu), 1.44 (s, 9H, $CH_3$ Boc), 0.93 (d, 6H, $CH_3$ Leu); $^{13}$C NMR (100 MHz, $CDCl_3$) δ: 173.5, 172.5, 156.3, 136.7, 129.7, 129.0, 127.5, 80.9, 62.1, 56.9, 52.3, 42.9, 40.8, 38.6, 28.7, 24.7, 23.4, 22.0; LC/MS: $t_R$ 5.52 min (20-80% B %, A=$H_2O$, B=ACN, flow=0.5 ml/min), m/z 444.2 $[M+Na]^+$.

PVA-PEG Supported TEMPO Catalyst

Preparation of 4-prop-2-ynyloxy-TEMPO 24

To a solution of 4-hydroxy-TEMPO 23 (1 g, 5.8 mmol) and $BU_4NBr$ (93.5 mg, 5 mol %) in THF (20 mL), NaH (0.334 g, 50% in purity, 120 mol %) was added portion-wise at room temperature under inert $N_2$ atmosphere (see Scheme 7). After stirring for 1 h at room temperature, the mixture was treated dropwise with an 80 wt % solution of propargyl bromide in toluene (3.45 g, 400 mol %) and the reaction mixture was heated at reflux overnight, cooled, filtered and concentrated under vacuum. The residue was purified by flash chromatography (silica gel, 100%-90% hexane in AcOEt) to give propargyl ether 24 as an orange-red crystalline solid (1.03 g, 84%): mp=63-64° C.; FTIR: 3232, 2111, 1085 $cm^{-1}$. Anal. Calcd for $C_{12}H_{20}NO_2$: C, 68.57; H, 9.52; N, 6.67. Found: C, 68.73; H, 9.73; N, 6.50. LC/MS: $t_R$ 12.95 min, ESI, m/z 211.0 $[M+H]^+$.

TEMPO Resin 25

Following the procedure for preparing the Wang linker resin 15, TEMPO-propargyl ether 24 (see Scheme 7) was coupled onto the azido PVA-PEG resin 12 possessing 5 or 20 PEG units via [2+3]cycloaddition chemistry yielding a brown TEMPO resin 25. Nitrogen elemental analysis indicated a loading of 1.85 and 1.04 mmol/g for TEMPO resin 25 with PEG units of 5 and 20, respectively. FTIR: 1467 cm$^{-1}$ of nitroxyl moiety and 3120 cm$^{-1}$ of =CH stretching band.

General Procedure for Alcohol Oxidation

A stoppered plastic tube-shaped reactor fitted with a Teflon filter was charged with 1 mL of alcohol solution 26 (see Scheme 7) in DCM (0.4 M) and milligrams of PVA-PEG_5 TEMPO resin (1.85 mmol/g, 3 mol % for primary alcohol and 10 mol % for secondary alcohol). To the solution at room temperature, 1.25 mL of bleach (0.4 M) buffered with KHCO$_3$ at pH 9.1 and KBr (0.5 M, 0.08 mL) were added. The reaction was shaken at room temperature for 30 to 240 minutes and monitored by TLC. The solution was filtered and the phases were separated. The aqueous phase was washed with DCM (2×1 mL). The combined organic phase was dried over Na$_2$SO$_4$ and concentrated to give the aldehyde or ketone 27.

Reuse of TEMPO-PVA-PEG Resin 25

Benzyl alcohol was used in a recycle oxidation study of resin 25 (see Scheme 7). Into a stoppered plastic tube-shaped reactor fitted with a Teflon filter, 1 mL of benzyl alcohol solution in DCM (0.4 M) and 9 mg of PVA-PEG TEMPO resin (3 mol %, 1.3 mmol/g) was added together with 1.25 mL of bleach (0.4 M) buffered with KHCO$_3$ at pH 9.1 and KBr (0.5 M, 0.08 mL). The reaction was shaken vigorously at room temperature and was monitored by TLC every 5 min. After a complete oxidation cycle was observed by the disappearance of benzyl alcohol spot on TLC (R$_f$ 0.28, hexane/ethyl acetate 4:1) and the formation of a single darker benzaldehyde spot under UV lamp (R$_f$ 0.53, hexane/ethyl acetate 4:1), the solution was filtered and the phases were separated. The resin was washed with DCM (2×1 mL) and used again in the next oxidation cycle without any further treatment. Fresh portions of alcohol, bleach and KBr were charged into the reactor with the recycled TEMPO resin. The reaction mixture was shaken at room temperature until TLC indicated the complete oxidation and the resin was filtered, washed and retreated with fresh alcohol as described above.

Characterization of Aldehydes and Ketones 27

27a) Benzaldehyde: quantitive conversion by TLC; yield: 98%; R$_f$ 0.53 (hexane/ethyl acetate 4:1); $^1$H NMR (CDCl$_3$) δ (ppm) 10.06 (s, 1H), 7.92 (d, 2H, J=7.34 Hz), 7.66 (t, 1H, J=7.80 Hz), 7.57 (t, 2H, J=7.80 Hz). 27b) Cyclohexanone: quantitive conversion by TLC; yield: 20.4%; R$_f$ 0.4 (hexane/ethyl acetate 4:1); $^1$H NMR (CDCl$_3$) δ (ppm) 2.36 (t, 4H, J=6.77 Hz), 1.89 (m, 4H), 1.75 (m, 2H). 27c) Octanal: quantitive conversion by TLC; yield: 18%; R$_f$ 0.42 (hexane/ethyl acetate 4:1); $^1$H NMR (CDCl$_3$) δ (ppm) 9.79 (t, 1H, J=1.91 Hz), 2.44 (dt, 1H, J=1.92, 7.48 Hz), 2.35 (t, 1H, J=7.48 Hz), 1.65 (m, 2H), 1.29-1.33 (m, 10H), 0.90 (t, 3H, J=7.13 Hz). 27d) Octan-2-one: quantitive conversion by TLC; yield: 11.2%; R$_f$ 0.50 (hexane/ethyl acetate 4:1); $^1$H NMR (CDCl$_3$) δ (ppm) 2.43 (t, 2H, J=7.50 Hz), 2.15 (s, 3H), 1.58 (m, 2H), 1.27-1.32 (m, 6H), 0.90 (t, 3H, J=6.96). 27e) Dodecanal: quantitive conversion by TLC; yield: 62.5%; R$_f$ 0.69 (hexane/ethyl acetate 4:1); $^1$H NMR (CDCl$_3$) δ (ppm) 9.79 (t, 1H, J=1.91), 2.44 (dt, 1H, J=1.91, 7.49), 2.37 (t, 1H, J=7.49), 1.65 (m, 2H), 1.28-1.32 (m, 18H), 0.90 (t, 3H, J=7.13). 27f) δ-Valerolactone: quantitive conversion by TLC; yield: 54%; R$_f$ 0.29 (hexane/ethyl acetate 1:1); $^1$H NMR (CDCl$_3$) δ (ppm) 4.37 (t, 2H, J=5.40 Hz), 2.58 (t, 2H, J=7.00 Hz), 1.91 (m, 4H). 27 g) N-Boc glycinal: quantitive conversion by TLC; yield: 87%; R$_f$ 0.45 (ethyl acetate/methanol 9:1); $^1$H NMR (CDCl$_3$) δ (ppm): 9.68 (s, 1H), 5.21 (s, 1H), 4.1 (d, 2H, J=4.61), 1.48 (s, 9H). 27 h) N-Benzyl N-(Boc) glycinal: quantitive conversion by TLC; yield: 82%; R$_f$ 0.31 (hexane/ethyl acetate 1:1); $^1$H NMR (CDCl$_3$) δ (ppm): 9.51 (s, 0.48H), 9.44 (s, 0.52H), 7.23-7.37 (m, 5H), 4.57 (s, 1.1H), 4.52 (s, 0.9H), 3.95 (s, 0.93H), 3.80 (s, 1.07H), 1.52 (s, 3.86H), 1.49 (s, 5.14H). 27i) (2R)-2-[N-(Boc)Amino]-3-methyl-3-hydroxy-butanal: quantitive conversion by TLC; yield: 90%; R$_f$ 0.55 (hexane/ethyl acetate 1:2); [α]$^{20}_D$ 103° (c 1.0, CHCl$_3$); $^1$H NMR (CDCl$_3$) δ (ppm): 9.82 (s, 1H), 5.46 (s, 1H), 4.28 (d, 1H, J=5.83), 2.74 (s, 1H), 1.48 (s, 9H), 1.36 (s, 3H), 1.34 (s, 3H). 27j) 1-N-Cbz-3-pyrrolidinone: quantitive conversion by TLC; yield: 86%; R$_f$ 0.46 (hexane/ethyl acetate 1:1); $^1$H NMR (CDCl$_3$) δ (ppm): 7.34-7.39 (m, 5H), 5.19 (s, 2H), 3.87 (t, 2H, J=7.75 Hz), 3.83 (s, 2H), 2.62 (t, 2H, J=7.75 Hz); $^{13}$C NMR (CD$_3$OD) δ (ppm): 210.8, 155.3, 136.7, 129.0 (2C), 128.7, 128.5 (2C), 67.7, 52.8, 43.1, 37.2. 27k) 5-α-Cholestan-3-one: 96% conversion by $^1$H NMR; isolated yield: 80% after column chromatography: gradient of 5-10% EtOAc in hexanes; R$_f$ 0.56 (hexane/ethyl acetate 4:1); $^1$H NMR (CDCl$_3$): 0.70 (s, 3H), 0.88 (d, 3H), 0.89 (d, 3H), 0.93 (d, 3H), 1.03 (s, 3H), 1.04-2.4 (m, 31H); $^{13}$C NMR (CDCl$_3$) δ (ppm): 212.6, 56.7, 56.6, 54.2, 47.1, 45.2, 43.0, 40.3, 39.9, 39.0, 38.6, 36.6, 36.2, 36.1, 35.8, 32.1, 29.4, 28.5, 28.4, 24.6, 23.2, 23.0, 21.9, 19.0, 12.5, 11.8. 27l) Methyl 3-oxo-5-β-cholan-24-oate: 99% conversion by $^1$H NMR; Isolated yield: 87% after column chromatography: gradient of 0-5% ethyl acetate in hexane; R$_f$ 0.38 (hexane/ethyl acetate 4:1); $^1$H NMR (CDCl$_3$): 0.70 (s, 3H), 0.94 (d, 3H), 1.04 (s, 3H), 1.11-2.7 (m, 28H), 3.69 (s, 3H); $^{13}$C NMR (CDCl$_3$): 213.8, 175.2, 56.8, 56.4, 51.9, 44.8, 43.2, 42.8, 41.1, 40.4, 37.6, 37.2, 35.9, 35.3, 35.8, 31.5, 31.4, 28.6, 27.0, 26.1, 24.6, 23.0, 21.6, 18.7, 12.5.

PVA PEG-Supported Hydroxyproline: Application in the Asymmetric Aldol Reaction

Preparation of PVA Peg-Supported Hydroxyproline (2S,4R)—N-Boc-trans-4-hydroxy-L-proline 31

Sodium hydroxide (1N, 48 mL) and a solution of Boc$_2$O (8.236 g, 36.60 mmol) in dioxane (12 mL) were sequentially added to a 0° C. solution of (2S,4R)-hydroxy-L-proline (4 g, 30.50 mmol) in 2:1 dioxane/water (108 mL). The solution was warmed to room temperature, stirred for 7 h, concentrated to a volume of about 60 mL using a rotary evaporator. The reduced volume was washed with ethyl acetate (200 mL), acidified with 1N HCl to pH 3 and extracted with ethyl acetate (3×200 mL). The combined organic extractions were dried over Na$_2$SO$_4$ and evaporated under reduced pressure to yield 31 (6.5 g, 93%) as a white solid: mp 95° C.; R$_f$ 0.56 (CHCl$_3$/MeOH 1/1); $^1$H NMR (CDCl$_3$, 400 MHz): δ 1.35 (s, 9H), 2.06-2.41 (m, 2H), 3.47-3.68 (m, 2H), 4.35-4.57 (m, 2H); MS (ESI): m/z: calcd for C$_{10}$H$_{17}$NO$_5$Na: 254.0999. found: 254.1002.

(2S,4R)—N-Boc-trans-4-hydroxy-L-proline tert-Butyl Ester 32

A stirred solution of 31 (1 g, 4.33 mmol) in dry CH$_2$Cl$_2$ (13 mL) was treated portion-wise with O-tert-butyl-trichloroacetimidate (1.9 g, 8.66 mmol), stirred for 1 day, filtered, evaporated and resubmitted to the same conditions as above for 2 days. Filtration and evaporation, followed by chromatography (40% EtOAc in hexane) gave ester 32 (0.310 g, 25%) as a clear oil: R$_f$ 0.44 (EtOAc); $^1$H NMR (CDCl$_3$, 400 MHz, carbamate isomers) δ 1.41-1.51 [s, 18H], 2.01-2.13 (m, 1H), 2.21-2.35 (m, 1H), [3.45 (d, 11.1 Hz), 3.55 (d, 11.6 Hz) 1H], [3.61 (d, 4.5 Hz), 3.65 (d, 4.4 Hz) 1H], [4.28 (t, 7.7 Hz), 4.33 (t, 7.5 Hz) 1H], 4.48 (br, s, 1H); HRMS (ESI): m/z: calcd for C$_{14}$H$_{26}$NO$_5$: 288.1806. found: 288.1810.

(2S,4R)-tert-Butyl N-Boc-4-propargyloxyprolinate 33

A solution of alcohol 32 (0.235 g, 0.818 mmol) in dry DMF (3 mL) was added to a suspension of sodium hydride (0.056 g, 2.18 mmol, not prewashed) in dry DMF (3 mL) at −20° C. under argon. The mixture was stirred for 40 min, treated dropwise with propargyl bromide (0.3 mL, 2.74 mmol), stirred for 1 h at −20° C., allowed to warm to room temperature with stirring for 18 h, treated with MeOH (1 mL), and with CH$_2$Cl$_2$ (3×10 mL) and washed with brine (3 mL). The combined organic extracts were dried and concentrated in vacuo. Purification by silica gel column chromatography (20% EtOAc in hexane) gave 33 (0.2 g, 75%) as a yellow oil R$_f$ 0.42 (hexane/EtOAc: 8/2); $^1$H NMR (CDCl$_3$, 400 MHz) δ 1.41-1.51 (m, 18H), 2.01-2.12 (m, 1H), 2.28-2.41 (m, 1H), 3.5-3.52 (m, 1H), 3.58-3.69 (m, 1H), 4.11-4.17 (m, 2H), 4.29-4.35 (m, 2H); HRMS (ESI): m/z: calcd for C$_{17}$H$_{28}$NO$_5$: 326.1962. found: 326.1962.

Protected Proline Resin 34

PVA-PEG__20 Azide resin 12 (0.052 g, 1.44 mmol/g) was agitated with (2S,4R)— tert-butyl N-Boc-4-propargyloxyprolinate 33 (0.030 g, 0.092 mmol), DIPEA (0.172 mL, 0.980 mmol), and CuI (0.0018 g, 0.0009 mmol) in 1:1 DMF/THF (2 mL) at 35° C. for 24 h. The resin was collected by filtration and rinsed successively with water (3×5 mL), DMF (3×5 mL), THF (3×5 mL), 1:1 THF/MeOH (3×5 mL), MeOH (3×5 mL) and THF (3×5 mL), and dried under vacuum for 24 h to yield a brown resin 34. The degree of functionalization f (mmol of functional fragment/g of resin) was calculated from the results of elemental analysis with the formula f=0.714/nx% N where n is the number of nitrogen atoms in the functional unit and % N is the percent of nitrogen provided by the elemental analysis. Elemental analysis (%) N, 5.43; C, 54.06; H, 8.21. f 0.97 mmol/g; IR (KBr)=2920 (C—H), 1741 (C=O), 1701 (C=O), 1405 (tBu), 1391 (tBu) cm$^{-1}$ Proline Resin 35

Trifluoroacetic acid (2.3 mL) was added to a suspension of resin 34 (0.116 g, 0.97 mmol/g) in CH$_2$Cl$_2$ (2.3 mL). The mixture was agitated for 1 h. The deprotection was monitored by FT-IR. The resin was collected by filtration (when the IR-signals of tBu and carbonyl groups had completely disappeared) and rinsed successively with THF (with 2% of Et$_3$N, 3×5 mL), water (3×5 mL), THF (3×5 mL), 1:1 THF/MeOH (3×5 mL), MeOH (3×5 mL) and THF (3×5 mL), and dried under vacuum for 24 h to yield a brown solid 35: IR (KBr) 2920 (C—H), 1600 (C=O) cm$^{-1}$; elemental analysis (%) N, 6.17; C, 51.09; H, 8.04. f 1.1 mmol/g.

Asymmetric Aldol Reaction

4-Hydroxy-4-(4'-bromophenyl)butan-2-one 36

A stirred solution of catalyst 35 (0.01 g, 0.011 mmol) in dry DMF (0.785 mL) and acetone (0.392 mL, 2.72 mmol) was treated with 4-bromobenzaldehyde (0.0072 g, 0.04 mmol), stirred at room temperature for 68 h and Resin 35 was filtered off. The mixture was treated with Et$_2$O and washed twice with water Et$_2$O phase was dried and concentrated The product was analyzed by the $^1$H NMR spectroscopy of the crude $^1$H NMR spectroscopy of the crude showed a 70% conversion by measuring the CHOH peak of the aldol product at 5.12 ppm vs the CHO peak of the p-bromobenzaldehyde at 9.90 ppm $^1$H NMR (CDCl$_3$, 400 MHz): δ=2.20 (s, 3H), 2.82 (m, 2H), 5.12 (m, 1H), 3.58-3.69 (m, 1H), 4.11-4.17 (m, 1H), 4.29-4.35 (m, 2H), 7.24-47 (m, 4H). Moreover, examination of the aldol product by chiral HPLC using a Chiralpak AS Daicel (i-PrOH/hexane 15/85), UV 280 nm, flow rate 1.0 mL/min, t$_R$minor 8.950 min and t$_R$major 10.143 min showed the presence of one single peak at 8.950 min retention time.

Results and Discussions

Preparation and Characterization of PVA-PEG Resin
Preparation of PVA Beads

Epichlorohydrin (EP) has a low solubility in water, and is immiscible with PVA aqueous solution. According to the previously reported method for preparing PVA beads as described in ((a) Wan, Y.; Huang, W-Q.; Wang, Z.; Zhu, X. X. *Polym.* 2004, 45, 71-7; (b) Wang, Z.; Luo, J. T.; Zhu, X. X.; Jin S. J.; Tomaszewski, M. J. *J. Comb. Chem.* 2004, 6, 961-966), a pre-crosslinking step was performed before paraffin oil was added to the reaction mixture such that EP could react with the PVA solution to obtain a certain degree of crosslinking.

For example, dimethylsulfoxide was employed in the new method to help solvate EP into the aqueous PVA solution. Polymerization in this miscible aqueous-organic phase, which dispersed into paraffin oil, gave spherical beads in 93% yield with a mean size of 87 μm analyzed by particle sizer (suspension in water). By this new method, the pre-crosslinking step could be avoided and the PVA beads that were obtained exhibited better mechanical stability due to a higher degree of crosslinking.

Grafting PEG onto PVA Resin

A few different strategies were employed to graft PEG onto PVA resin, including ether bond formation by toluenesulfonate activated PEG or mono PEG chloride and coupling of PEG via a diisocyanate linkage as shown in Scheme 1.

Scheme 1. Various methods used to graft PEG onto PVA resin

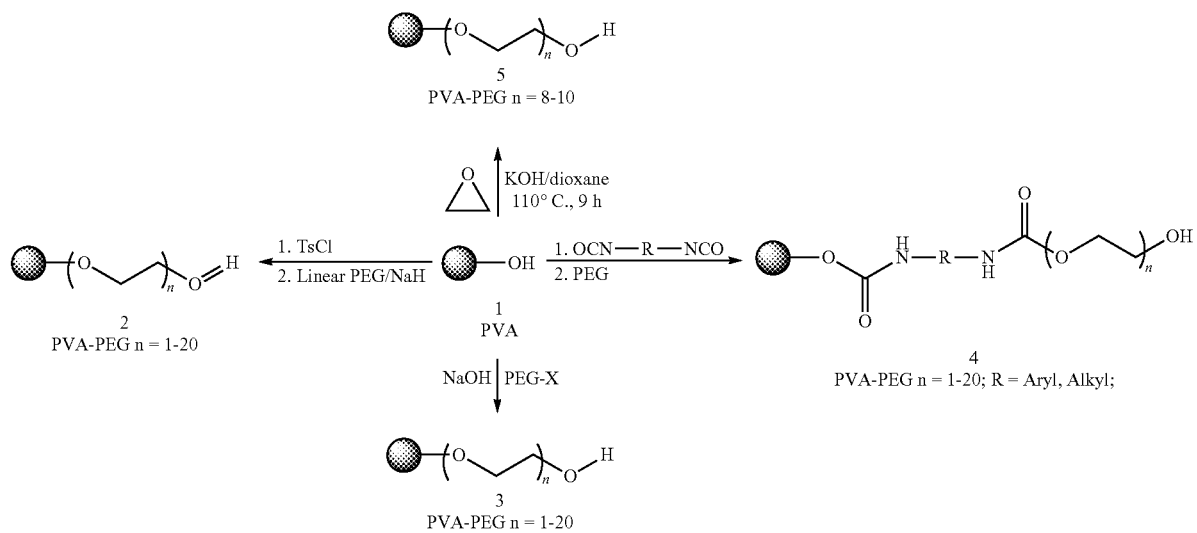

Williamson ether synthesis was used in a polymer-grafting reaction. Diisocyanate compounds were also employed to anchor PEG onto PVA resin. After coupling of isocyanate resin with poly(ethyleneglycol), the NCO band disappeared from the FTIR spectrum, and the hydroxyl (3420 cm$^{-1}$) and urethane (171.1, 1529 cm$^{-1}$) bands were enhanced. In the first step to prepare isocyanate resin, excess of IPDI was employed to minimize the crosslinking reaction. The loading of the OH group was estimated based on Nitrogen Elemental Analysis of urethane groups to be 2.79 mmol/g for the mono ethylene glycol attached PVA-IPDI-EG resin. The weight of resin increased from 1.0 g to 4.7 g after the ethylene glycol coupling. The resulting resin swelled well in organic solvent, such as DCM, ethyl acetate, THF and DMF.

Ring-opening polymerization of ethylene oxide onto crosslinked PVA beads was examined under high pressure at 110° C. in dioxane. The resulting PEG grafted PVA beads were shown to have a loading of 1.5-2 mmol/g by acetic anhydride titration.

Anionic Polymerization of Ethylene Oxide onto PVA Beads

The mechanism for such an anionic polymerization could be, without being found to such a theory, as shown in Scheme 2.

Potassium naphthalene, dimsyl ion and PVA supported potassium alkoxide, could all initiate the polymerization of ethylene oxide (EO).

Scheme 2. Anionic polymerization of ethylene oxide onto PVA beads.

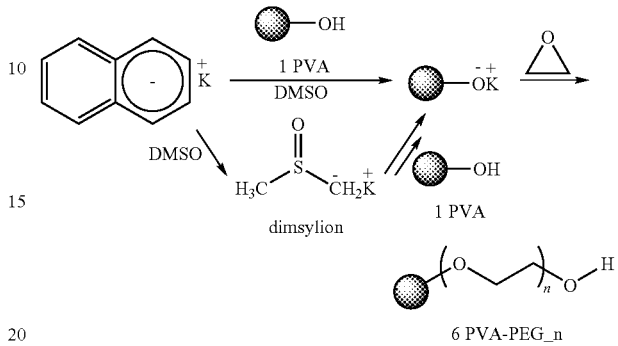

The anionic polymerization of EO onto PVA beads in DMSO was reproducible as illustrated by the successful attachment of PEG segments corresponding to 5 EO repeating units onto the PVA beads in three consecutive reactions (Table 1, entries 2, 3 and 4).

TABLE 1

Conditions for anionic polymerization of ethylene oxide and selected properties of PVA-PEG copolymer resin 6.

| Resins | Units (n) | EO (mL) | Mass gain (%) | $L_{calc'd}$[a] (mmol/g) —OH | $L_{titr'd}$[b] (mmol/g) —OH | $L_{Fmoc}$[c] (mmol/g) Fmoc-Gly | —OH |
|---|---|---|---|---|---|---|---|
| 1 PVA-PEG_2A | 2.2 | 1.8 | 71 | 9.9 | 9.2 | 2.1 | 4.8 |
| 2 PVA-PEG_5A | 4.3 | 3.0 | 140 | 7.3 | 6.5 | 1.9 | 4.0 |
| 3 PVA-PEG_5A | 5.0 | 3.0 | 150 | 6.8 | 6.2 | 1.8 | 3.7 |
| 4 PVA-PEG_5A | 5.6 | 3.0 | 165 | 6.2 | 5.8 | 1.7 | 3.2 |
| 5 PVA-PEG_8A | 7.4 | 3.2 | 242 | 5.0 | 4.5 | 1.6 | 2.8 |
| 6 PVA-PEG_12A | 12.1 | 4.0 | 360 | 3.7 | 3.5 | 1.4 | 2.4 |
| 7 PVA-PEG_15A | 15.2 | 5.0 | 460 | 3.0 | 2.3 | 1.2 | 1.9 |
| 8 PVA-PEG_20A | 19.9 | 6.0 | 598 | 2.4 | 2.1 | 1.0 | 1.4 |
| 9 PVA-PEG_5B[d] | 5.1 | 2.5 | 124 | 6.7 | 6.2 | 1.9 | 4.0 |
| 10 PVA-PEG_12B[d] | 12.5 | 4.0 | 350 | 3.6 | 3.4 | 1.6 | 2.8 |
| 11 PVA-PEG_20B[d] | 19.8 | 5.0 | 600 | 2.1 | 2.0 | 1.1 | 1.5 |

Starting with 0.4 g PVA beads and 2.7 mmol naphthalene potassium, ethylene oxide was polymerized at 40° C. for 48 h;

[a]theoretical loadings of hydroxyl group were calculated based on the mass gain onto the beads;

[b]loadings of hydroxyl group were ascertained by titrating the excess acetic acid formed upon the reaction of copolymer beads with acetic anhydride.

[c]loading was calculated by the Fmoc-UV method: PVA-PEG resins were acylated with Fmoc-glycine, and the Fmoc loading was determined by spectrophotometric measurement at 301 nm of the dibenzofulvene adducts formed after treatment of the resin with piperidine.

[d]PVA-PEG_nB resins were sythesized from PVA beads that were made by method B, and 2.2, 2.5 and 2.7 mmol naphthalene potassium were added starting from 0.4 g PVA resin, respectively for entries 9, 10 and 11.

By adding different amounts of ethylene oxide to the reaction, a series of PVA-PEG copolymer beads 6 were produced having different PEG chain lengths. Hydroxyl group loading in the copolymers was measured by acetic anhydride titration and corresponded closely to the calculated loading based on the weight increase of the beads after reaction.

Characterization of the PVA-PEG Beads 6

Loading of Hydroxyl Groups

Theoretically, linear PVA has one alcohol group per repeating unit, and the loading of linear PVA with 98% hydroxylation has a maximum theoretical value of 22 mmol/g. Crosslinking PVA diminishes the number and the accessibility of the secondary hydroxyl groups. The hydroxyl group loadings of PVA beads 1 crosslinked with epichlorohydrin by both the pre-gelation (method A) and DMSO-water (method B) processes were, respectively, titrated to be 17 mmol/g and 15 mmol/g. Polymerization of EO onto cross-linked PVA maintains the number of hydroxyl groups. Titrated loadings using $Ac_2O$ were found to be in close agreement with the calculated value based on the weight increase of the beads (Table 1). In order to evaluate the accessibility of the hydroxyl groups during peptide and organic synthesis, PVA-PEG resins 6 were acylated with N-Fmoc glycine. The Fmoc loading was then measured by spectrophotometric measurement at 300 nm of the dibenzofulvene adducts formed after treatment of the resin with piperidine. The hydroxyl group loadings were determined using this Fmoc method to be lower (1.5-4.8 mmol/g) than those measured by the $Ac_2O$ titration (2.0-9.2 mmol/g). The Fmoc method was assumed to reflect the accessibility of OH groups, because acylation with the sterically more hindered Fmoc-glycine was expected to occur on fewer hydroxyl groups than the smaller acetic anhydride. The PVA-PEG beads 6 exhibited typically higher loading than commercial PEGylated solid supports, such as Tenta Gel, Argo Gel, PEGA and SPOCC resin, which have loadings of less than 0.4 mmol/g. For example, copolymer with PEG chain lengths of 15 and 20 units had hydroxyl group loadings of around 2 mmol/g. Higher loadings (2 to 5 mmol/g) were obtained by decreasing the amount of EO in the feed during the polymerization.

Swelling of the PVA-PEG Beads

Contingent with the growth of the PEG chain length, the graft copolymer beads 6 became softer and sticker after lyophilization, yet they dispersed well in the solution. The swelling of the PVA-PEG beads 6 was studied using a solvent-mass absorption method with a capillary to transfer the solvent to the polymer. Beads saturated with solvent were incapable of reducing the volume in the capillary. They were then weighed and the volume of the absorbed solvent was calculated based on the solvent density.

The swelling behavior of PVA beads 1 prepared by methods A and B, Merrifield resin, Wang resin and Tenta Gel resin, all were studied in six common solvents (see FIG. 1): water, DMF, THF, DCM, acetonitrile and toluene. PVA beads 1 prepared from crosslinking in DMSO-water (method B) were observed to have lower swelling than PVA beads synthesized via the pre-crosslinking (method A). PVA beads (A and B) by themselves swelled well in water (about 7 mL/g and 10 mL/g) and DMF (about 8 mL/g and 12 mL/g), due to the high density of the hydroxyl groups. It should be noted that for Wang (OH) resin and Merrifield (Cl) resin, the swelling of these beads in water cannot be given by the solvent adsorption method, since water cannot soak the resin. PVA A(B) and PVA-PEG_nA(B) resins were prepared from methods A and B, respectively.

The copolymer beads 6 exhibited good swelling in aqueous and in organic solvents (see FIG. 1). Increased solubility in less polar organic solvents was proportional to the increase in PEG chain length. In contrast, the swelling of the copolymer in water and DMF peaked at 2 EO units (15 and 17 mL/g, respectively) and decreased to around 9 mL/g at longer PEG chain length (20 EO units). The copolymer beads that were made from densely crosslinked PVA beads (prepared by method B) swelled slightly less in water and organic solvents relative to copolymer beads with similar PEG chain length that were prepared by method A.

Relative to the PVA beads 1, the swelling of PVA-PEG beads 6 in organic solvents was significantly improved and usually increased with PEG chain length. For example, the low swelling of 1 mL/g for PVA beads in DCM was increased to 12 mL/g (8 mL/g for densely crosslinked PVA-PEG_20) on attachment of around 20 EO units. In THF and acetonitrile, swelling was increased from 2-3 mL/g (PVA beads) to about 6-8 mL/g at longer PEG chain lengths. In toluene, the swelling increased by a factor of two on going from 0 to 20 units of EO grafted polymer. In organic solvents, compared with Merrifield and Wang resin, PVA-PEG copolymer resin 6 had similar swelling properties except in toluene. The PVA-PEG resin exhibited consistently higher swelling than Tenta Gel resin in all solvents. The PVA-PEG resin may thus be useful for packing in columns for continuous flow peptide synthesis, because their consistently high swelling should result in slight volume changes in the pack material on applying different solvents during synthesis.

Stability of PVA-PEG Beads 6

After being magnetically stirred for 48 h during the anionic polymerization of EO onto the PVA beads, the resulting copolymer beads were observed under the microscope. The densely crosslinked PVA-PEG beads 6 (prepared by method B) exhibited a more consistent spherical form relative to material made by method A, indicative of higher mechanical stability. To examine chemical stability, PVA-PEG beads with 5 PEG chain units were exposed, respectively overnight, to 6 N NaOH and to 6 N HCl. The beads were observed to remain in spherical shape under the microscope, and their FTIR spectra were unchanged. After treatment, the PVA-PEG beads were acylated with Fomc-glycine and loadings were analyzed by UV spectrophotometry after Fmoc cleavage and found to be 1.71 and 1.85 mmol/g respectively for resins exposed to 6 N NaOH and to 6 N HCl, which compared favorably with the 1.83 mmol/g loading of original PVA-PEG resin 6.

FTIR Study of the PVA-PEG Beads

Infrared spectroscopy was employed to characterize beads before and after the anionic polymerization. In the IR spectrum of PVA beads, a strong absorption for the hydroxyl group was observed at about 3380 $cm^{-1}$ (see FIG. 2). Although no hydroxyl groups were consumed during synthesis, the copolymer beads 6 exhibited lower hydroxyl group absorption as the mass increased from grafting 2 to 20 PEG chain lengths. Concurrently, the ether band at 1106 $cm^{-1}$ and the methylene band at 2870 $cm^{-1}$ became stronger with increasing PEG chain length.

NMR Characterization of the PVA-PEG Beads

PVA-PEG resins 6 were initially characterized by liquid gel-phase proton NMR spectroscopy using $d_6$-DMSO to swell and suspend the resin in a 20 cm NMR tube. The $^1H$ NMR spectra showed that very distinct changes occurred to the PVA beads after the anionic polymerization (see FIG. 3). The chemical shifts of the diastereotopic hydroxyl resonances of the beaded PVA polymer in DMSO-$d_6$ were observed at 4.2 ppm, 4.4 ppm and 4.6 ppm respectively ((a) Moriani, T.; Fujiwara, Y. *Macromolecules* 1977, 10, 532-535; (b) Budhlall, B. M.; Landfester, K.; Sudol, E. D.; Dimonie, V. L.; Klein, A.; El-Asser, M. S. *Macromolecules* 2003, 36, 9477-9484) for the different stereochemical configurations of the PVA polymeric chains. In contrast, a signal for the hydroxyl groups of the PEG grafted PVA copolymer was observed at 4.5 ppm and the intensity decreased proportionally with increasing PEG length. The relative intensity of the proton signals at 1.4 ppm for the PVA backbone diminished sharply on the elongation of the PEG chains. At the same time, the line widths of the proton signals of the PEG methylene groups at 3.8 ppm became sharper due to the longer tethers providing more mobility.

MAS $^1$H NMR (Keifer, P. A. *Drug Discovery Today* 1997, 2, 468-478) (Grotli M.; Goffredsen C. H.; Rademann J.; Buchardt J.; Clark A. J.; Duus J. O.; Meldal M. *J. Comb. Chem.* 2000, 2, 108-119) spectroscopy with a $^1$H MAS nanoprobe with a spinning frequency of around 6 KHz was also used to on-bead analyze resin bound compounds. On-bead structure analysis of Wang linker resin 15 using HR-MAS $^1$H NMR spectrometry was performed (see FIG. 7) and two dimensional HMQC and TOCSY spectra were recorded to identify the structure. Resin 15 with 20 PEG units provided a better resolution and smaller line widths in DMF-d$_7$ than PVA-PEG_5 resin, and the splittings of aromatic proton doublets were observed to be 6.5 Hz at 7.50 and 7.22 ppm in the spectrum of PVA-PEG_20 Wang linker resin. Furthermore, PVA-PEG resin exhibits no signal in the lower field (above 3.8 ppm) which avoid overlaps with signals from supported structures may thus during on-bead HR-MAS $^1$H NMR analysis.

DSC Study of the PVA-PEG Beads 6

Differential Scanning Calorimeter (DSC) was used to study the thermal behavior of the PVA-PEG beads. The first DSC heating curves of the copolymers 6 with different length of PEG were recorded at a heating rate of 10° C./min after a cooling with liquid nitrogen from room temperature to –100° C. at a speed of –10° C./min. The pure PVA beads have a glass transition at about 50° C. (see FIG. 4). For the copolymers with short PEG chains, the glass transition temperature decreased from 50° C. to 20° C. to –25° C., and finally shifted to the glass transition of PEG (about –50° C.) at the PEG chain lengths ≧8. The absence of multiple T$_g$s suggests that grafting was homogeneous. The DSC curves for copolymers with PEG chain lengths of 15 and 20 exhibited melting peaks of the PEG chain at about 10° C. and 20° C., respectively, suggesting that the PEG chains were long enough to align themselves into a crystalline phase. The melting point of linear PEG has been reported to depend on PEG molecular weight: 400 to 500 g/mol and 600 g/mol PEG melted at 10° C. and 20-25° C. respectively. The grafted PEG also showed a similar relationship between melting points and molecular weight. Beads with PEG chain lengths of 15 and 20 were calculated to have PEG molecular weights of 660 and 880 g/mol, and exhibited melting points that were 10 and 20° C., respectively, lower than that of the corresponding linear PEG due to the inhibition of PEG-chain crystallization by the crosslinked PVA polymer matrix.

Morphology Study

Cross-linked PVA beads 1 have been shown to have porous structures by scanning electron microscopy (SEM) ((a) Wan, Y.; Huang, W-Q.; Wang, Z.; Zhu, X. X. *Polym.* 2004, 45, 71-7; (b) Wang, Z.; Luo, J. T.; Zhu, X. X.; Jin S. J.; Tomaszewski, M. J. *J. Comb. Chem.* 2004, 6, 961-966), and the pore size decreased with the degree of cross-linking. The SEM spectra of the cross-linked PEG derivatized PVA beads suggested that the pores were filled in by flexible PEG (see FIG. 5). Finally, PVA-PEG copolymer with 5 and 20 PEG units had a gel-like structure, and PVA-PEG_20 beads had a smoother surface than PVA-PEG_5. Optical microscopy showed that PVA beads and PVA-PEG beads were both spherically shaped with bead sizes varying from 10 to 50 μm in dry state.

Modification of PVA-PEG Resin 6

Densely crosslinked PVA beads, prepared from the new method, had better mechanical properties than PVA beads prepared by the reported method ((a) Wan, Y.; Huang, W-Q.; Wang, Z.; Zhu, X. X. *Polym.* 2004, 45, 71-7; (b) Wang, Z.; Luo, J. T.; Zhu, X. X.; Jin S. J.; Tomaszewski, M. J. *J. Comb. Chem.* 2004, 6, 961-966). Densely crosslinked PVA-PEG B beads also swelled better than most commercial resins in aqueous and organic media.

High-density functionality is desired for scavenger resin. Hydroxyl groups on the PVA-PEG resin 6 were in a high loading capacity and oxidized into aldehyde, carboxylic acid and further converted into isocyanate groups providing potential scavenger resins. The hydroxyl groups on the PVA-PEG B beads were extended by way of a benzyl alcohol in a Wang linker to meet the peptide chemistry on Wang resin.

PVA-PEG Aldehyde Scavenger 7 and Carboxylic Acid Resin 8

Oxidation of the PVA-PEG resin was examined to prepare aldehyde and carboxylic acid resin. The bleach/TEMPO/DCM procedure was employed to convert the hydroxyl groups on the PVA-PEG resin into aldehyde groups as shown in Scheme 3.

Scheme 3. Preparation of aldehyde, carboxylic acid and isocyanate resins 7, 8 and 10 from PVA-PEG resin 6.

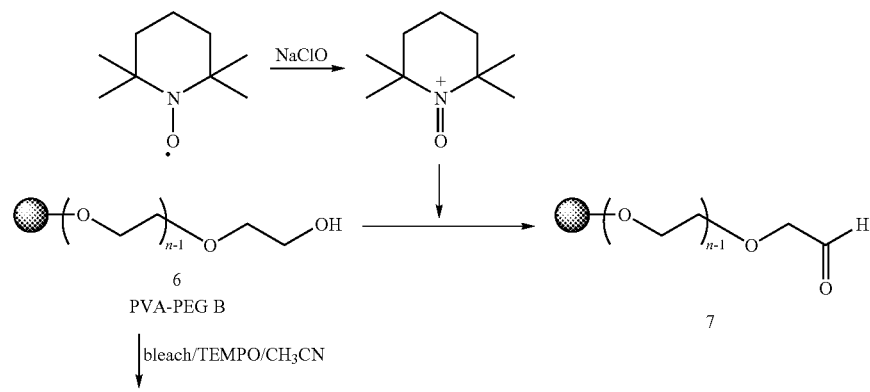

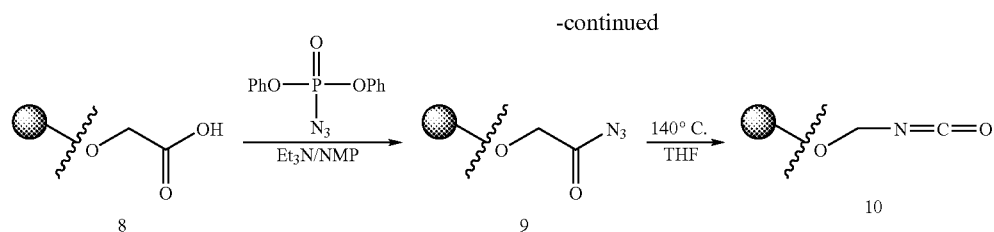

When excess bleach (≧2.5 eq.) and a long reaction time (overnight) were used to push conversion, over-oxidation of the OH groups occurred and the corresponding acid was observed by FTIR (1735 cm$^{-1}$) and no aldehyde groups were detected by a dansylhydrazine-flourescence titration. Although, aldehydes are easily oxidized by bleach into acids, the aldehyde resin could be produced by a two-step TEMPO oxidation process. First, TEMPO in DCM was oxidized with bleach. The phases were separated and the organic phase was in turn applied to oxidize PVA-PEG resin. After employing this oxidation process, no carboxylic acid was observed by FTIR and the aldehyde loading was ascertained to be 0.8 mmol/g using rapid fluorescence titration for resin 7.

To prepare carboxylic acid resin 8, acetonitrile was used to help solvate both TEMPO and PVA-PEG resin 6 in the aqueous bleach phase during the oxidation (Scheme 3). The resulting resin 8 exhibited a strong carbonyl band (1737 cm$^{-1}$) in the FTIR spectrum indicative of the formation of carboxylic acid. PVA-PEG carboxylic acid resin was reacted with diphenyl phosphoryl azide in 1-methyl-2-pyrrolidinone to yield the carbonyl azide resin 9. In the FTIR spectrum of 9, the carbonyl band shifted to 1718 cm$^{-1}$ and a characteristic azide band appeared at 2162 cm$^{-1}$. Nitrogen elemental analysis of resin 9 indicated an azide loading of 2.27 mmol/g. Curtius rearrangement by heating carbonyl azide resin 9 in THF to 140° C. was performed to prepare isocyanate resin 10. The shift of the —CON$_3$ band (2162 cm$^{-1}$) to a —NCO band (2266 cm$^{-1}$) in the FTIR spectrum was indicative of isocyanate formation.

Preparation of PVA-PEG Resin 15 Possessing a Wang Linker

Introducing Wang linker onto PVA-PEG resin is interesting to produce a new resin which can be applied in the known peptide chemistry, it also demonstrate the potential of the PVA-PEG resin to be modified into more diverse functions. Immobilization of Wang linker onto the PVA-PEG resin was initially accomplished using the Cu(I)-catalyzed [2+3] dipolar cycloaddation reaction between an organic azide and a terminal alkyne (see Scheme 4), (the so-called "click chemistry") ((a) Rostovtsev, V. V.; Green, L. G.; Fokin, V. V.; Sharpless, K. B. *Angew. Chem., Int. Ed.* 2002, 41, 2596; (b) Kolb, H. C.; Finn, M. G.; Sharpless, K. B. *Angew. Chem., Int. Ed.* 2001, 40, 2004).

Scheme 4. Preparation of PVA-PEG resin 15 possessing a Wang linker and dipeptides synthesis.

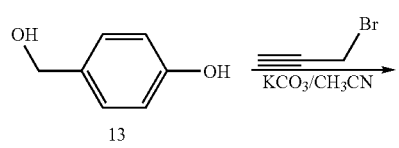

Figure 7:
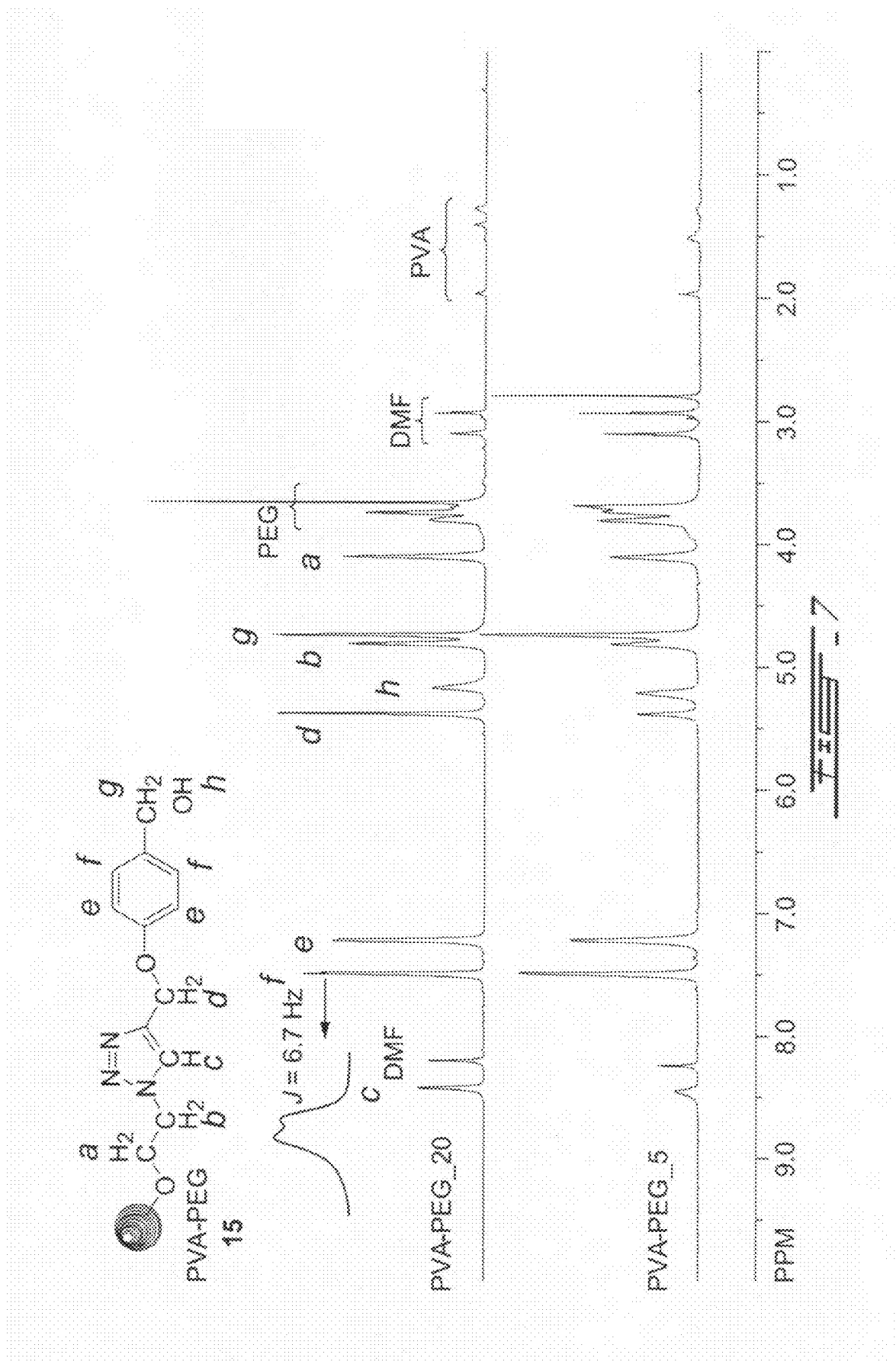
FIG. 7 shows the HR-MAS 1H NMR spectra of examples of PVA-PEG resins according to particular embodiments of the present invention.

PVA-PEG Wang linker resin 15 was thus prepared starting from PVA-PEG resins 6, possessing an average repeat of 5 and 20 units of PEG, respectively, by methanesulfonation with methanesulfonyl chloride in DCM at 0° C. In the FTIR spectrum of the methanesulfonate resin 11 (see FIG. 6), two strong sulfonyl stretch bands at 1352 and 1174 cm$^{-1}$ appeared, and the hydroxyl adsorption around 3400 cm$^{-1}$ decreased significantly in intensity relative to the starting alcohol resin. After exposure of methanesulfonate resin 11 to sodium azide, the FTIR spectrum indicated the complete disappearance of the sulfonyl bands and the appearance of a new strong azide adsorption at 2106 cm$^{-1}$. Nitrogen elemental analysis indicated azide loadings of 2.42 and 1.25 mmol/g for azido resin 12 with the PEG units of 5 and 20, respectively. 4-Prop-2-ynyloxy-benzyl alcohol 13 was prepared by alkylation of the phenoxide ion of p-hydroxy benzyl alcohol with propargyl bromide in 96% yield. Propargyl ether 14 was then reacted with azido PVA-PEG resin 12, with 5 and 20 PEG Units, in the presence of catalytic CuI to give the triazole linked PVA-PEG Wang resin 15. The loading of the benzyl alcohol group tethered by the triazole was determined by nitrogen elemental analysis to be 1.63 and 1.08 mmol/g, respectively for the resins possessing 5 and 20 PEG units. Similar loadings of hydroxyl groups were ascertained for resins 15 with 5 and 20 PEG units by using the assay featuring Fmoc-glycine coupling followed by UV detection of dibenzofulvene after the cleavage with piperidine (1.74 and 1.08 mmol/g, respectively). Three characteristic adsorptions for the aromatic ring were observed at 1598, 1514 and 1465 cm$^{-1}$ in the FTIR spectrum of PVA-PEG Wang resin 15. On-bead HR-MAS $^1$H NMR spectra were performed to confirm the structure of Wang linker using (FIG. 7). And PVA-PEG resin 15 possessing Wang linker was demonstrated effective in peptide synthesis (see Scheme 4).

Applications of PVA-PEG Resins

As an initial demonstration of the utility of PVA-PEG resin, 1) amide bond formation in solid phase peptide chemistry was studied; and 2) a novel catalytic resin for alcohol oxidation was prepared.

Peptide Synthesis on the PVA-PEG Resins

The transglutaminase substrate dipeptide Z-Gln-Gly (Gillet, S. M. F. G.; Chica, R. A.; Keillor, J. W.; Pelletier, J. N.; *Prot. Exp. & Purif.* 2004, 33, 256-264) and inhibitory heptapeptide Pro-Asn-Pro-Gln-Leu-Pro-Phe residues were synthesized on PVA-PEG resin 6 with repeats of 5 and 20 PEG units and the Wang linker derivatized PVA-PEG resin using the standard Fmoc chemistry. In both cases, the first amino acid was anchored onto the resin using DIC and DMAP in DMF, subsequent couplings were performed using the DIC and HOBt in DMF. The peptides were cleaved off from the resins in three different conditions.

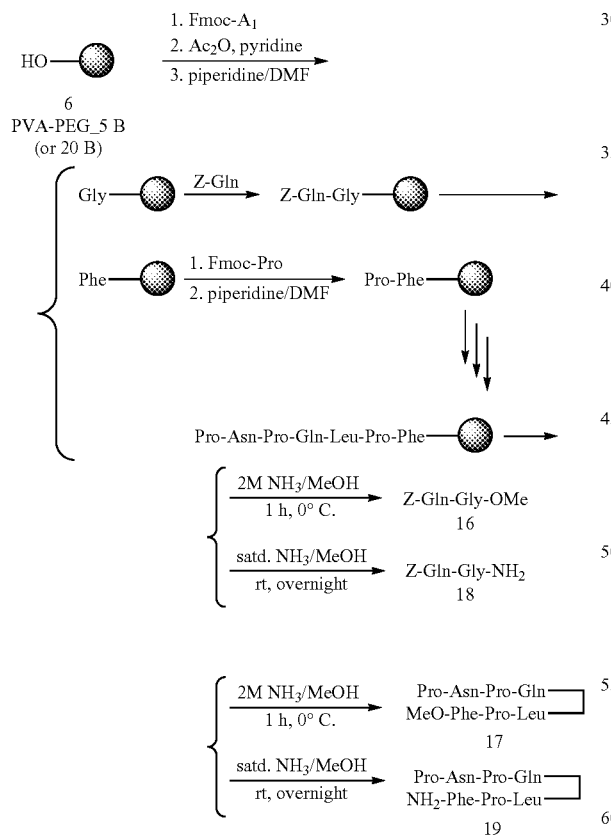

Scheme 5. Dipeptide and heptapeptide synthesis on PVA-PEG resin.

Firstly, dipeptides and heptapeptides were cleaved from PVA-PEG_5 and PVA-PEG_20 resins using a 2.0 M solution of ammonia in methanol at 0° C. for 1 h yielding peptide methyl ester. Z-Gln-Gly-OMe 16 (see Scheme 5) were isolated in 75%, 84% yields and 98%, 96% purity (analyzed by LC-MS) for PVA-PEG_5 resin and PVA-PEG-20 respectively. The heptapeptide methyl ester 17 was obtained in 53% and 18% isolated yields and 75% and 50% purities (analyzed by LC-MS) for PVA-PEG_5 resin and PVA-PEG_20 resin, respectively. Secondly, dipeptide and heptapeptide were cleaved from PVA-PEG_5 resin using a saturated solution of ammonia in methanol at room temperature overnight giving amido peptide Z-Gln-Gly-NH$_2$ 18 in 98% isolated yields and 92% purity (analyzed by LC-MS) and amido heptapeptides 19 by precipitation from acetone with diethyl ether in 99% isolated yield and 70% purity (analyzed by LC-MS). The second cleavage condition provided higher yields and purities than the first method performed at 0° C. Additionally, Z-Gln-Gly dipeptide residues were synthesized on Wang linker derivatized PVA-PEG resins and cleaved using a 50% solution of TFA in DCM (v/v) at room temperature for 1 h. The dipeptides Z-Gln-Gly were isolated in 100% and 65% yields and 90% and 91% purities (analyzed by LC-MS) for the resins possessing 5 and 20 PEG units, respectively.

Examining the synthesis of peptide alcohols, PVA-PEG supported Boc-Phe-Leu and Boc-Phe-(D)Leu were synthesized (Scheme 6) as described above and treated with a solution of β-amino ethanol (glycinol) in 1:1 DCM:acetonitrile at 50° C.

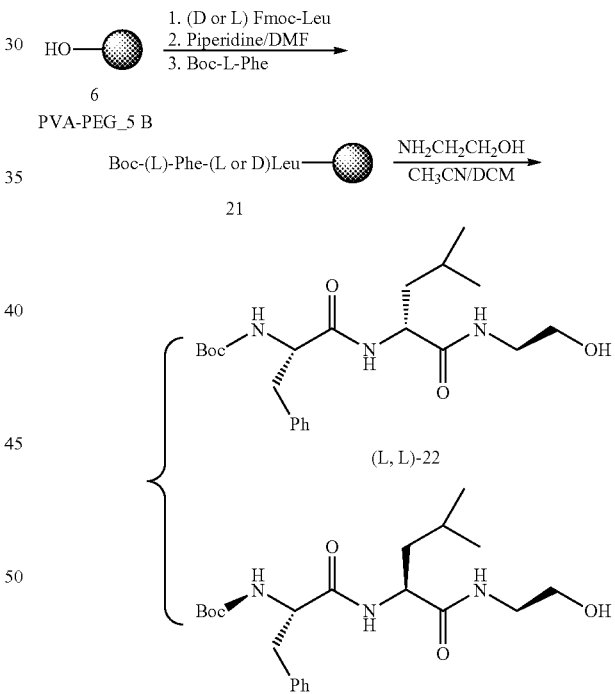

Scheme 6. Preparation of peptide alcohols 22.

Precipitation of the residue in ethyl acetate/hexane gave crude peptide alcohols (L,L)-22 and (L,L)-22 in 93% and 96% isolated yields with 90% and 95% purities as determined by LC/MS analysis. The diastereomeric purity of Boc-Phe-Leu-Gly alcohol was ascertained to be >99.5% by incremental additions of the L,D-isomer and observation of the methyl group signals at 0.82 (triplets) and 0.93 (doublets) ppm of leucine for L and D-isomers, respectively in the $^1$H NMR spectra. Strong base and high temperature during the cleavage were observed to decrease the diastereomeric purity of the peptide alcohol, such that Boc-Phe-Leu-Gly alcohol was isolated in 97.5% diastereomeric purity by cleavage at 80° C., and 81% diastereomeric purity when 0.1 N of NaOCH$_3$ at 80° C.

PVA-PEG Supported TEMPO Catalyst 25 for Alcohol Oxidation

Preparation of TEMPO Resin 25

The TEMPO/bleach/DCM protocol has been often employed as an inexpensive oxidation procedure; however, column chromatography has commonly been required to remove TEMPO from the product. Therefore, by linking the catalyst TEMPO onto one of the solid supports of the present invention, purification of aldehyde and ketone products can be conveniently performed after resin filtration. Covalent attachment of TEMPO catalysts to linear polymers have previously produced soluble polymer supported nitroxyl radicals that have served in homogeneous oxidation of alcohols; however, the low loading of linear polymers and the loss of activity on recycling the catalyst have been drawbacks to the use of these catalysts of the prior art. In addition, the removal of the linear polymer supported catalyst typically requires precipitation using copious amount of solvent. Amorphous and ordered mesoporous silica surfaces, microporous sol-gel silica supports, and crosslinked polystyrene all have been employed to immobilize TEMPO to provide catalysts that have been used in heterogeneous alcohol oxidations; however, these heterogeneous TEMPOs require typically the use of a monophasic organic media which necessitates a purification step to remove the terminal oxidant. A limited number of primary and secondary alcohols have been previously reported to be oxidized into aldehydes or ketones with favorable efficiency using these various supported TEMPO reagents. Novel solid supported TEMPO reagents as those presented in the present invention are thus still needed for the practical and environmentally friendly oxidation of diverse alcohols into pure aldehydes and ketones.

To demonstrate the generality of the dipolar cycloaddition for adding substituents onto PVA-PEG resin, the immobilization of TEMPO onto the PVA-PEG resin was accomplished using same procedure to attach Wang linker onto PVA-PEG resin via the Cu(I)-catalyzed [2+3] dipolar cycloaddition reaction as shown in Scheme 7.

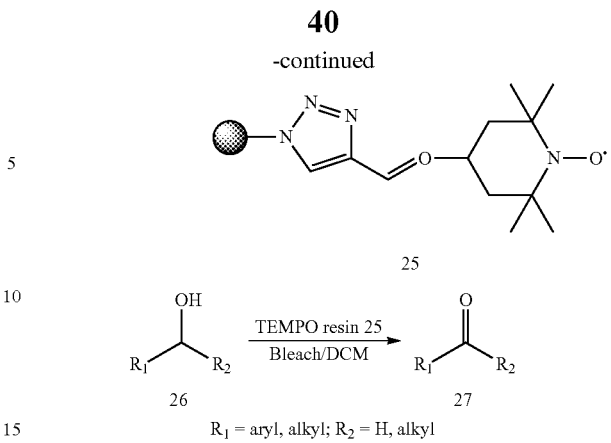

4-Prop-2-ynyloxy-TEMPO 24 was prepared in 84% yield from 4-hydroxyl TEMPO 23 and propargyl bromide using NaH as a base in THF. The [2+3]cycloaddation and anchoring of the TEMPO catalyst was performed using azido resin 12 and propargyl TEMPO ether 24 in the presence of CuI as catalyst in DMF at room temperature. The FTIR spectra of TEMPO resin 25 revealed characteristic stretching frequency for the N—O group of the nitroxyl moiety (1467 cm$^{-1}$) and =C—H on triazole ring (3120 cm$^{-1}$), as well as the complete disappearance of the absorbance for the azide at 2106 cm$^{-1}$. The loading of TEMPO were determined by nitrogen elemental analysis to be 1.8 and 1.04 mmol/g for the resin 25 with PEG units of 5 and 20, respectively.

Bleach/PVA-PEG TEMPO Oxidation of Alcohol

According to the proposed oxidation mechanism, but without being found to such a theory, (Adam, W.; Saha-Möller, C. R.; Ganeshpure, P. A. Chem. Rev. 2001, 101(11), 3499) (Scheme 8), nitroxyl radical 25 is converted to the active oxoamonium ion 28, which oxidizes the alcohol 26 to carbonyl product 27 via an intermediate complex 29 to afford hydroxylamine 30. Oxoamonium ion 28 is subsequently regenerated by sodium hypochlorite as primary oxidant, as shown in Scheme 8.

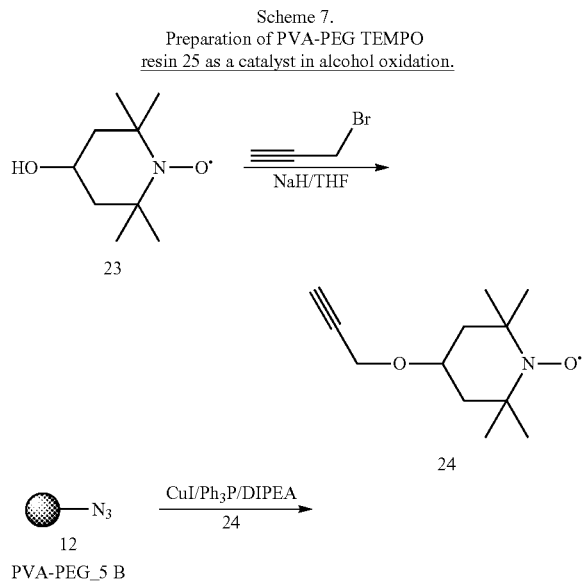

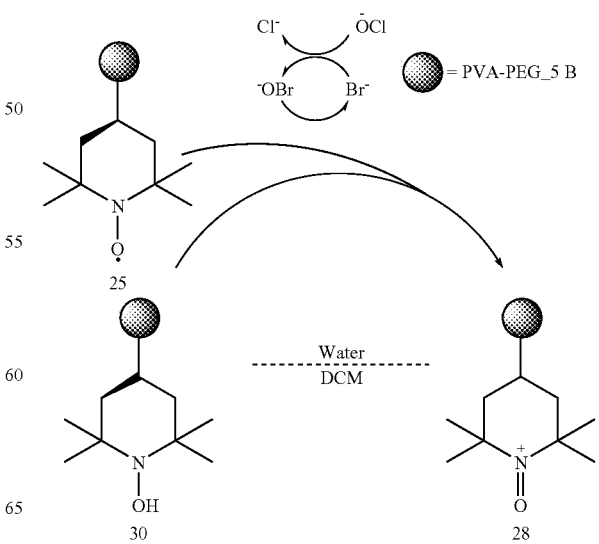

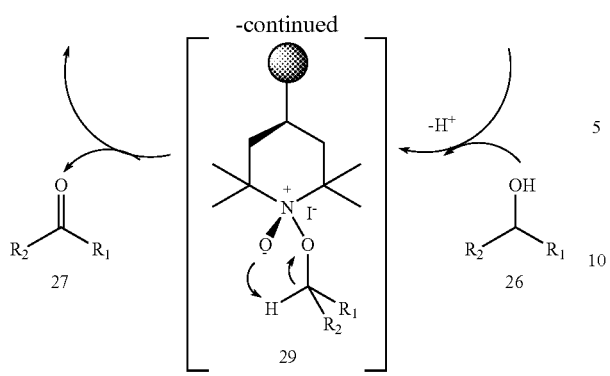

A distinct color change of the TEMPO resin was observed during the oxidation of alcohol. In bleach containing KBr to accelerate the oxidation, PVA-PEG TEMPO catalyst was yellow in color. On addition of alcohol, the resin changed color from light yellow to deep brown during the oxidation. After the oxidation was completed using excess sodium hypochlorite, the TEMPO resin, which was presumed to be in the oxidation state of an oxoamonium ion 28 (Scheme 8), returned to its original light yellow color. The FTIR spectrum of recovered resin showed bands at 1731 and 1541 $cm^{-1}$ indicative of the N=O stretches of the oxoamonium ion.

Similar to the parent resin, PVA-PEG TEMPO resin 25 swelled effectively in dichloromethane and water. The density of TEMPO resin 25 was observed to be between that of water and DCM, such that the resin floated at the interface of these two phases during the reaction. Such physical properties were considered to enhance catalytic activity by facilitating the transfer of the reaction intermediates between the two phases.

Recycling of TEMPO resin 25, after hypochlorite oxidation of alcohol under biphasic conditions, was examined by using 3300 mol % of benzyl alcohol and monitoring the oxidation by TLC every 5 min. After complete conversion of alcohol was observed, the resin 25 was filtered and employed in the next oxidation cycle. After five cycles, the oxidation was complete within 5 min as shown in Table 2.

TABLE 2

Recycle of TEMPO resin 25 in the oxidation of benzyl alcohol.

| | Cycle | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Time (min) | 5 | 5 | 5 | 5 | 5 | 10 | 10 | 10 | 10 | 15 | 15 | 18 |

Note: the completed oxidation time was indicated by observation of a spot to spot conversion on the TLC plate ($R_f$ BnOH: 0.28, hexane/ethyl acetate 4:1; $R_f$ PhCHO: 0.53, hexane/ethyl acetate 4:1).

Simply structured aromatic and aliphatic alcohols (entries 26a-26e) were observed to be quantitatively oxidized within 5 to 60 min as observed by spot to spot conversions on TLC. Pentane-1,5-diol 26f was oxidized into lactone 27f with 2.5 equivalent of bleach. The isolated yields of the volatile products (27b to 27f) were low due to product loss during the solvent evaporation. A series of N-Boc- and Cbz-amino alcohols (entries 26g-26j) were next subjected to the PVA-PEG-TEMPO/bleach/DCM oxidation as shown in Table 3.

TABLE 3

Oxidation of alcohols to aldehydes and ketones with PVA-PEG TEMPO resin 25

| Entry | Alcohol 26 | Aldehyde 27 (ketone) |
|---|---|---|
| a | benzyl alcohol | benzaldehyde |
| b | cyclohexanol | cyclohexanone |
| c | CH₃(CH₂)₅CH₂OH | CH₃(CH₂)₅CHO |
| d | 2-heptanol | 2-heptanone |
| e | CH₃(CH₂)₉CH₂OH | CH₃(CH₂)₉CHO |
| f | HO(CH₂)₅OH | δ-valerolactone |

TABLE 3-continued

| | Entry | Time (min) | Conv. | Yield (%)[c] | δ [ppm] —CHO |
|---|---|---|---|---|---|
| | a | 5 | 100%[a] | 98 | 10.06 |
| | b | 30 | 100%[a] | 20.4[d] | — |
| | c | 30 | 100%[a] | 18[d] | 9.79 |
| | d | 60 | 100%[a] | 11.2[d] | — |
| | e | 60 | 100%[a] | 62.5[d] | 9.78 |
| | f | 120 | 100%[a] | 54[d] | — |
| | g | 30 | 100%[a] | 87 | 9.68 |
| | h | 30 | 100%[a] | 82 | 9.51 |
| | | | | | 9.44 |
| | i | 30 | 100%[a] | 90 | 9.82 |
| | j | 30 | 100%[a] | 86 | — |
| | k | 240 | 96%[b] | 85 (80) | — |
| | l | 240 | >99%[b] | 90 (87) | — |

[a]Monitored by TLC.
[b]Determined by $^1$H NMR spectroscopy.
[c]Isolated yields (after column).
[d]Volatile compounds The corresponding amino aldehydes (27g-27i) and amino ketones (27j) were quantitatively isolated in 82-92% yield after resin filtration, phase separation, drying and evaporation of the organic phase. Steroid alcohols required longer reaction time for complete oxidation into the corresponding ketones. For example, oxidation of steroidal alcohols 26k and 26l were estimated by $^1$H NMR spectroscopy (monitoring the disappearance of protons on position $C_{1-3}$ at 3.61 and 3.55 ppm, respectively) have undergone >96% and >99% conversion after 6 h, and the corresponding steroidal ketones were, respectively, isolated in pure form in 80% and 87% yields after chromatography on silica gel to remove unreacted alcohols.

PVA PEG-Supported Hydroxyproline: Application in the Asymmetric Aldol Reaction

As previously indicated (2S,4R)—N-Boc-trans-4-Hydroxy-L-proline 31 was prepared from commercially available and inexpensive (4R)-hydroxy-L-proline according to a published procedure (Biel, M.; Deck, P.; Giannis, A.; Waldmann, H. *Chem. Eur. J.* 2006, 4121-4143). (2S,4R)-tert-Butyl N-Boc-4-propargyloxyprolinate 33 was then prepared by esterification to provide tert-butyl ester 32, (Surprenant, S.; Lubell, W. D. *J. Org. Chem.* 2006, 71 (2), 848-851), followed by O-alkylation with propargyl bromide (Scheme 9) (Font, D.; Jimeno, C.; Pericàs, M. A. *Org. Lett* 2006, 8, 4653-4655).

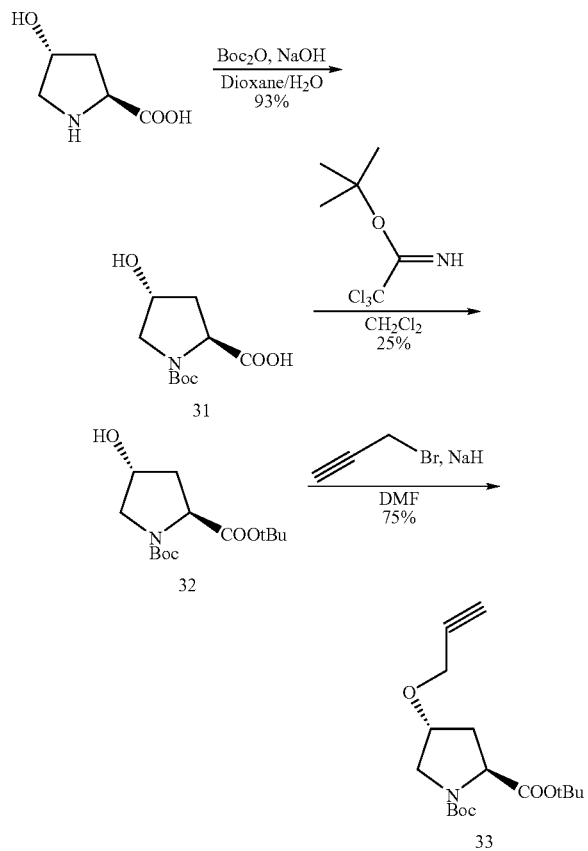

Supported hydroxyproline 35 was prepared by reacting O-propargyl hydroxyprolinate 33 and azide resin PVA-PEG$_{20}$-N$_3$ using a 1,3-dipolar cycloaddition, followed by removal of Boc and tert-butyl ester groups using 50% TFA in CH$_2$Cl$_2$ (Scheme 10).

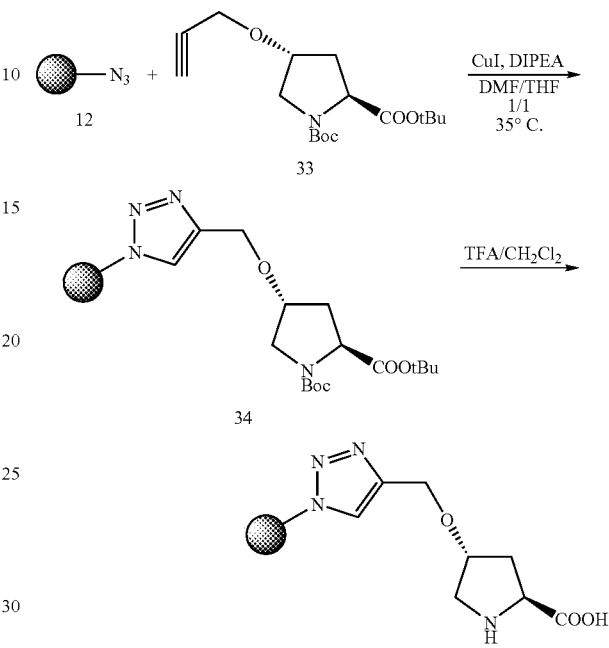

The resin was characterized by FT-IR spectroscopy and elemental analysis. For resins 34 and 35, the degree of functionalization f (mmol of functional fragment/g of resin) was calculated based on the results of the elemental analysis with the formula f=(0.714/n) % N nitrogen where n is the number of nitrogen atoms in the functional unit and % N is the percent of nitrogen provided by the elemental analysis By this method, PVA-PEG$_{20}$ supported hydroxyproline resin 35 had a loading of 1.1 mmol/g on the basis of nitrogen elemental analysis (% N found=6.17).

Asymmetric Aldol Reaction

The application of PVA-PEG-supported hydroxyproline as catalyst for the asymmetric aldol reaction, was tested in the reaction of acetone and p-bromobenzaldehyde at room temperature using 28 mol % of resin in DMF at room temperature (Scheme 11). After 68 h under these conditions, filtration of the resin and solvent evaporation, the crude product exhibited a conversion of ca 70% as observed in the $^1$H NMR spectrum by measuring the ratio of the respective peaks for the aldol product beta proton (5.12 ppm) and starting material aldehyde proton (9.9 ppm). Moreover, examination of the racemic aldol product by chiral HPLC, using a Chiralpak AS Daicel (i-PrOH/hexane 15/85), with UV detection at 280 nm, and a flow rate 1.0 mL/min, showed two peaks at 8.950 min and 10.143 min. On the other hand, HPLC analysis of material obtained from the enantioselective aldol reaction with resin 35 showed the presence of one predominant peak with a retention time at 8.950 min.

Scheme 11. Aldol reaction catalyzed by resin

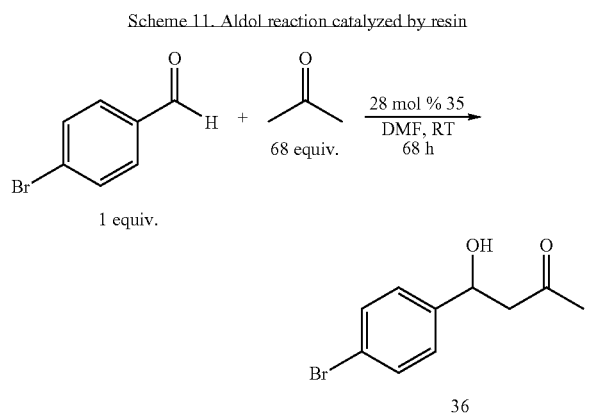

These results indicate that PVA-PEG proline resin 35 is an effective catalyst for the enantioselective aldol condensation reaction.

In brief, anionic polymerization was used to graft polyether including PEG onto a cross-linked poly(vinyl alcohol) core in a controlled fashion to prepare beads with tailored physical properties. Poly(vinyl alcohol)-graft-poly (ethylene glycol) (or poly(vinyl alcohol)-graft-polyether) beads were made having high functional group loading and good swelling in water and a range of organic solvents. Peptide chemistry was performed on such a new copolymer resin, and dipeptides and heptapeptides were successfully synthesized. Furthermore, attachment of TEMPO onto PVA-PEG crosslinked resin via a [2+3]cycloaddation has produced a new solid phase heterogeneous catalyst. In a biphasic bleach/DCM alcohol oxidation, PVA-PEG supported TEMPO catalyst provided effectively aldehydes and ketones which were conveniently purified by resin filtration. PVA-PEG TEMPO catalyst could be recycled for more than twelve subsequent oxidations without significant loss of catalyst efficiency. Hydroxyl groups on the PVA-PEG resin were also oxidized into aldehyde and carboxylic acid groups via TEMPO/bleach oxidation to provide potential scavenger resins. Moreover, an asymmetric aldol reaction was carried out using a PVA PEG-supported hydroxyproline.

The PVA-PEG beads were stable to strong acid (6 N HCl) and basic (6 N NaOH) conditions. The flexible PEG chains and pseudo symmetrical spherical polyether matrix may contribute to the observed enhanced resolution during on-bead NMR experiments of support-bound compound. It was thus proved that such PVA-PEG resins are versatile supports for both organic synthesis and aqueous chemistry, due to their high loading and compatible swelling properties in aqueous and organic solvents Such novel polymer supports for organic and peptide synthesis were developed based on beaded PVA-PEG copolymer. Anionic polymerization of ethylene oxide onto crosslinked PVA beads gave effectively the grafted copolymer, which was characterized by NMR and FTIR spectroscopy as well as DSC. The morphology of the beads was analyzed by high resolution scanning electron microscopy and found to be a typical gel-phase with a smooth surface. The swelling behavior of the PVA-PEG beads was observed to be higher than that of commercial resins in water, polar solvents and most nonpolar organic solvents. The resins can be uniform or polydispersed. The beads had relatively high functional group loading, which was adjusted by changing the length of the PEG chain and the crosslinked state of the PVA core. PVA-PEG with 20 PEG units was found to be suitable for the study of substrate on-bead by NMR spectroscopy. Diversely functionalized PVA-PEG resins were prepared including PVA-PEG aldehyde, carboxylic acid and isocyanate resins as well as PVA-PEG resin possessing a Wang linker. Peptide synthesis was successfully accomplished on grafted copolymer resins and the Wang linker derivatized PVA-PEG resins with different PEG lengths. Enantiopure peptide alcohols were also synthesized by nucleophilic displacement of carboxylates linked to PVA-PEG resin. Moreover, a novel crosslinked polymer supported TEMPO catalyst was synthesized and its utility was demonstrated in an effective three-phase catalytic oxidation system for making aldehydes and ketones possessing a diverse variety of functionality. After product separation, the resin-bound catalyst could be recycled.

The person skilled in the art would recognize that various modifications, adaptations, and variations may be brought to the previously presented specific examples without departing from the scope of the following claims.

The invention claimed is:
1. A compound of formula:

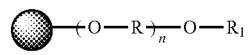

wherein

represents a poly(vinyl alcohol) polymer or a copolymer containing vinyl alcohol and/or vinyl acetate;
—(—O—R—)$_n$—O—R$_1$ represents a plurality of poly (ethylene glycol) or polyether chains that are attached to said poly(vinyl alcohol) polymer or a copolymer containing vinyl alcohol and/or vinyl acetate, each of said chains independently comprising n repeating units;
n having a value of about 1 to about 100;
R is an alkyl group chosen from $(CH_2)_m$, $(CH_2CHR_3)_m$, and $(CHR_3—CHR_4)_m$, where m=1 to 12; and
R$_1$ is a catalyst chosen from TEMPO or a derivative thereof, a suitably modified transition metal catalyst that is a Rh- or Ru-phosphine analog, an analog of an organic catalyst chosen from a secondary amine, a thiazolium or imidazolium salt, a proline analog, an analog of cyclo [(S)-phenylalaninyl-(S)-histidinyl], an analog of a cinchona alkaloid, and a derivative of poly(L-leucine), or a derivative of said catalyst which comprises a linking moiety disposed between said compound and said catalyst;
R$_3$ is OH, NR$_4$R$_5$, C$_1$-C$_{20}$ alkyl linear or branched, C$_3$-C$_{12}$ cycloalkyl, C$_1$-C$_{12}$ heterocyclyl, C$_2$-C$_{20}$ alkenyl, C$_2$-C$_{20}$ alkynyl, C$_6$-C$_{12}$ aryl, C$_6$-C$_{20}$ aralkyl, C$_6$-C$_{20}$ alkylaryl, C$_2$-C$_{20}$ alkylheterocyclyl, C$_1$-C$_{12}$ heteroaryl, or C$_2$-C$_{20}$ alkylheteroaryl; and
R$_4$ is a hydrogen atom, a C$_1$-C$_{20}$ alkyl linear or branched, C$_3$-C$_{12}$ cycloalkyl, C$_1$-C$_{12}$ heterocyclyl, C$_2$-C$_{20}$ alkenyl, C$_2$-C$_{20}$ alkynyl, C$_6$-C$_{12}$ aryl, C$_6$-C$_{20}$ aralkyl, C$_6$-C$_{20}$ alkylaryl, C$_1$-C$_{12}$ heteroaryl, C$_2$-C$_{20}$ alkylheterocyclyl, C$_2$-C$_{20}$ alkylheteroaryl, or a suitable protecting group for an amino group;
said alkyl, cycloalkyl, heterocyclyl, alkenyl, alkynyl, aryl, aralkyl, alkylaryl, heteroaryl, alkylheterocyclyl, and alkylheteroaryl are unsubstituted or substituted with at least one substituent, each of said substituent(s) being chosen from F, Cl, Br, I, OH, SH, $NH_2$, $NO_2$, CN, $CF_3$, —SH, —$OCH_2Ph$, —OPh, —$SCH_3$, —SPh, —$SCH_2Ph$, —COOH, —$COOR_2$, $C_1$-$C_{12}$ alkyl linear or branched, $C_6$-$C_{12}$ aryl, $C_2$-$C_{20}$ alkenyl, $C_1$-$C_{20}$ alkoxy, $C_1$-$C_{20}$ alkyl, $C_2$-$C_{20}$ alkynyl, $C_6$-$C_{20}$ aralkyl, $C_6$-$C_{12}$ aryl, $C_3$-$C_8$ cycloalkyl, $C_1$-$C_{20}$ aminoalkyl, $C_6$-$C_{12}$ aminoaryl, $C_1$-$C_{12}$ aminoheteroaryl, $C_1$-$C_{20}$ hydroxyalkyl, $C_6$-$C_{12}$ hydroxyaryl, $C_1$-$C_{12}$ hydroxyheteroaryl, $C_1$-$C_{12}$ heterocyclyl, $C_1$-$C_{12}$ heteroaryl, $C_2$-$C_{20}$ alkylheterocyclyl, and $C_2$-$C_{20}$ alkylheteroaryl.

2. The compound of claim 1, wherein $R_1$ is TEMPO or a derivative thereof.

3. The compound of claim 1, wherein $R_1$ is said analog of an organic catalyst.

4. The compound of claim 3, wherein said organic catalyst is a thiazolium salt, an imidazolium salt, proline, cyclo[(S)-phenylalaninyl-(S)-histidinyl], a cinchona alkaloid, or a poly (L-leucine).

5. The compound of claim 1, wherein R is $(CH_2)_m$.
6. The compound of claim 2, wherein R is $(CH_2)_m$.
7. The compound of claim 3, wherein R is $(CH_2)_m$.
8. The compound of claim 4, wherein R is $(CH_2)_m$.
9. A compound of formula:

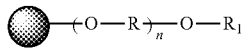

wherein

represents a poly(vinyl alcohol) polymer or a copolymer containing vinyl alcohol and/or vinyl acetate;

—(—O—R—)$_n$—O—$R_1$ represents a plurality of poly (ethylene glycol) or polyether chains that are attached to said poly(vinyl alcohol) polymer or a copolymer containing vinyl alcohol and/or vinyl acetate, each of said chains independently comprising n repeating units;

n having a value of about 1 to about 100;

R is an alkyl group chosen from $(CH_2)_m$, $(CH_2CHR_3)_m$ and $(CHR_3—CHR_4)_m$, where m=1 to 12;

$R_1$ is of formula -L-T, wherein L is a bond or a linker and T is an amino acid or a derivative thereof, a peptide or a derivative thereof, an oligonucleotide or a derivative thereof, a carbohydrate or a derivative thereof, a glycopeptide or a derivative thereof, a catalyst or a derivative thereof, or a catalytic reagent or a derivative thereof;

$R_3$ is OH, $NR_4R_5$, $C_1$-$C_{20}$ alkyl linear or branched, $C_3$-$C_{12}$ cycloalkyl, $C_1$-$C_{12}$ heterocyclyl, $C_2$-$C_{20}$ alkenyl, $C_2$-$C_{20}$ alkynyl, $C_6$-$C_{12}$ aryl, $C_6$-$C_{20}$ aralkyl, $C_6$-$C_{20}$ alkylaryl, $C_2$-$C_{20}$ alkylheterocyclyl, $C_1$-$C_{12}$ heteroaryl, or $C_2$-$C_{20}$ alkylheteroaryl;

$R_4$ is a hydrogen atom, a $C_1$-$C_{20}$ alkyl linear or branched, $C_3$-$C_{12}$ cycloalkyl, $C_1$-$C_{12}$ heterocyclyl, $C_2$-$C_{20}$ alkenyl, $C_2$-$C_{20}$ alkynyl, $C_6$-$C_{12}$ aryl, $C_6$-$C_{20}$ aralkyl, $C_6$-$C_{20}$ alkylaryl, $C_1$-$C_{12}$ heteroaryl, $C_2$-$C_{20}$ alkylheterocyclyl, $C_2$-$C_{20}$ alkylheteroaryl, or a suitable protecting group for an amino group;

said alkyl, cycloalkyl, heterocyclyl, alkenyl, alkynyl, aryl, aralkyl, alkylaryl, heteroaryl, alkylheterocyclyl, and alkylheteroaryl are unsubstituted or substituted with at least one substituent, each of said substituent(s) being chosen from F, Cl, Br, I, OH, SH, $NH_2$, $NO_2$, CN, $CF_3$, —SH, —$OCH_2Ph$, —OPh, —$SCH_3$, —SPh, —$SCH_2Ph$, —COOH, —$COOR_2$, $C_1$-$C_{12}$ alkyl linear or branched, $C_6$-$C_{12}$ aryl, $C_2$-$C_{20}$ alkenyl, $C_1$-$C_{20}$ alkoxy, $C_1$-$C_{20}$ alkyl, $C_2$-$C_{20}$ alkynyl, $C_6$-$C_{20}$ aralkyl, $C_6$-$C_{12}$ aryl, $C_3$-$C_8$ cycloalkyl, $C_1$-$C_{20}$ aminoalkyl, $C_6$-$C_{12}$ aminoaryl, $C_1$-$C_{12}$ aminoheteroaryl, $C_1$-$C_{20}$ hydroxyalkyl, $C_6$-$C_{12}$ hydroxyaryl, $C_1$-$C_{12}$ hydroxyheteroaryl, $C_1$-$C_{12}$ heterocyclyl, $C_1$-$C_{12}$ heteroaryl, $C_2$-$C_{20}$ alkylheterocyclyl, and $C_2$-$C_{20}$ alkylheteroaryl.

10. The compound of claim 9, wherein T is an amino acid or a derivative thereof.

11. The compound of claim 9, wherein T is a peptide or a derivative thereof.

12. The compound of claim 9, wherein T is catalyst or a derivative thereof.

13. The compound of claim 9, wherein T is catalytic reagent or a derivative thereof.

14. The compound of claim 9, wherein R is $(CH_2)_m$.
15. The compound of claim 10, wherein R is $(CH_2)_m$.
16. The compound of claim 11, wherein R is $(CH_2)_m$.
17. The compound of claim 13, wherein R is $(CH_2)_m$.
18. The compound of claim 9, wherein L is

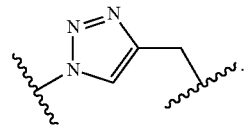

* * * * *